US006825320B1

(12) United States Patent
Shyjan

(10) Patent No.: US 6,825,320 B1
(45) Date of Patent: Nov. 30, 2004

(54) FOHY03 POLYPEPTIDES

(75) Inventor: Andrew W. Shyjan, Nahant, MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/862,442

(22) Filed: May 23, 1997

Related U.S. Application Data

(60) Division of application No. 08/623,679, filed on Mar. 29, 1996, now Pat. No. 5,674,739, which is a continuation-in-part of application No. 08/412,431, filed on Mar. 29, 1995, now Pat. No. 5,633,161.

(51) Int. Cl.[7] ...................... C07K 14/435; C07K 14/47; A61K 38/17; A61K 38/18; C07H 21/04

(52) U.S. Cl. ...................... 530/350; 530/399; 536/23.1; 536/23.5

(58) Field of Search ................................ 530/350, 399, 530/300; 536/23.1, 23.5, 23.3, 24.3, 24.31, 24.33, 24.5, 23.4; 424/99.1; 435/69.1; 514/2, 21

(56) References Cited

U.S. PATENT DOCUMENTS 5,262,321 A 11/1993 Livingston et al. ...... 435/240.2
5,457,049 A 10/1995 Giordano ............... 435/252.33
5,470,970 A 11/1995 Sager et al. ............... 536/23.5
5,487,985 A * 1/1996 McClelland et al. ....... 435/91.2
5,491,064 A 2/1996 Lichy et al. ................... 435/6
5,496,731 A 3/1996 Xu et al. ................. 435/320.1
5,565,340 A * 10/1996 Chenchik et al. .......... 435/91.2
5,633,161 A 5/1997 Shyjan ....................... 435/325
5,674,739 A 10/1997 Shyjan .................... 435/252.3
5,710,137 A 1/1998 Fisher ......................... 514/44
5,837,845 A 11/1998 Hosokawa et al. ...... 536/23.53

FOREIGN PATENT DOCUMENTS

WO WO 86/03226 6/1986
WO WO 92/15602 9/1992
WO WO 92/21781 12/1992
WO WO 93/22424 11/1993
WO WO 94/21115 9/1994
WO WO 95/05470 2/1995
WO WO 96/27603 9/1996

OTHER PUBLICATIONS

P. Bork, "Powers and pitfalls in sequence analysis", Genome Research, 2000, vol. 10, pp. 398–400.*

Mathews and Van Holde, Biochemistry (textbook), 2nd edition, pp. 165–171.*

B. Matthews, "Genetic and Structural analysis of the protein stability problem", in Perspectives in Biochemistry, vol. 1, pp. 6–9.*

Alberts et al, Ed., Molecular Biology of the Cell (textbook), 3rd edition, p. 465.*

Shantz and Pegg, "Translational regulation of ornithine decarboxylase and other enzymes", International J of Biochemistry and Cell Biology, vol. 31, pp. 107–122.*

McClean and Hill, "Evidence of post–translational regulation of p–glycoprotein", European J. of Cancer, vol. 29A, pp. 2243–2248.*

Fu et al, "Translational regulation of human p53 gene expression", EMBO, vol. 15, pp. 4392–4401.*

George et al. Current Methods in Sequence Comparison adn Analysis In Macromolecular Sequencing and Synthesis, Selected Methods and Applications pp. 127–149, 1988.*

Barton et al Protein Sequence Alignment and Database Scanning In Protein Structure prediction, A PracticalApproach, IRL Press at Oxford Univeristy pp. 31–63, 1996.*

Bowie et al, Science 247: 1306–1310, Mar. 16, 1990.*

Boeringer Mannheim Biochemicals, 1991 Catalog, Jan. 31, 1991.*

Zubay, G., Biochemistry, p. 912, Addison Wesley Publishing Co., Reading, Mass., Apr. 14, 1984.*

Shantz and Pegg, "Translational regulation of ornithine decarboxylase and other enzymes", International J of Biochemistry and Cell Biology, 1999, vol. 31, pp. 107–122.*

McClean and Hill, "Evidence of post–translational regulation of p–glycoprotein", European J. of Cancer, 1993, vol. 29A, pp. 2243–2248.*

Fu et al, "Translational regulation of human p53 gene expression", EMBO, 1996, vol. 15, pp. 4392–4401.*

Bowie et al., "Deciphering theMessage in Protein Sequences: Tolerance to Amino Acid Substitutions" Science 247:1306, 1990.

Burgess et al., "Possible Dissociation of the Heparin–binding and Mitogenic Activities of Heparin–binding (Acidic Fibroblast) . . . " J. Cell. Biol. 111:2129, 1990.

Fradet et al., "Cell Surface of Human Bladder Cancer Defined by Mouse Monoclonal Antibodies" Proc. Nat'l Acad. Sci. USA 81:224, 1984.

Harris et al., "Seminal Vesicle Secretion IV Gene: Allelic Difference Due to a Series of 20–base–pair direct Tandem Repeats within an Intron" Proc. Nat'l. Acad. Sci. USA, 80:6460, 1983.

(List continued on next page.)

*Primary Examiner*—Karen A. Canella
(74) *Attorney, Agent, or Firm*—Fish & Richardson P.C.

(57) ABSTRACT

The present invention relates to methods and compositions for the diagnosis, prevention, and treatment of tumor progression in cells involved in human tumors such as melanomas, breast, gastrointestinal, lung, and bone tumors, various types of skin cancers, and other neoplastic conditions such as leukemias and lymphomas. Genes are identified that are differentially expressed in benign (e.g., non-malignant) tumor cells relative to malignant tumor cells exhibiting a high metastatic potential. Genes are also identified via the ability of their gene products to interact with gene products involved in the progression to, and/or aggressiveness of, neoplastic tumor disease states. The genes and gene products identified can be used diagnostically or for therapeutic intervention.

16 Claims, 20 Drawing Sheets

OTHER PUBLICATIONS

Hillier et al., Accession No. N24756, Dec. 28, 1995.
Kahana et al., "Nucleotide Sequence of Murine Ornithine Decarboxylase mRNA" Proc. Nat'l Acad. Sci. USA 82:1673, 1985.
Lazar et al., "Transforming Growth Factor α: Mutation of Aspartic Acid 47 and Leucine 48 Results in Different Biological Activities" Mol. Cell. Biol. 8:1247, 1988.
Lewis et al., "The Sequence of the Kluyveromyces Lactis BiP Gene" Nucl. Acids Res. 18:6438, 1990.
Rieger et al., Glossary of Genetics and Cytogenetics, Classical and Molecular, Springe–Vertag, Berlin, 4$^{th}$ edition, 1976.
Schwartz et al., "A Superactive Insulin:[B10–Aspartic Acid] Insulin(Human)" Proc. Nat'l Acad. Sci. USA 84:6408, 1987.
Stratagene Catalog, p. 39, 1988.
Fidler, I.J., 1973, "Selection of Successive Tumor Lines for Metastasis," *Nature New Biol. 242*:148–149.
Fodde, R., et al., 1994, "A targeted chain–termination mutation in the mouse *Apc* gene results in multiple intestinal tumors," *Proc. Natl. Acad. Sci. USA 91*:8969–8973.
Folkman, J. and Klagsburn, M., 1987, "Angiogenic Factors," *Science 235*:442.
Hodgkinson, C.A., et al., 1993, "Mutations at the Mouse Microphthalmia Locus Are Associated with Defects in a Gene Encoding a Novel Basic–Helix–Loop–Helix–Zipper Protein," *Cell 74*:395–404.
Karmali, R.A., et al., 1993, "Prostaglandins in beast cancer: Relationship to disease stage and hormone status," *Br. J. Cancer 48*689–696.
Karmali, R.A., et al., 1987, "The Effects of Dietary ω–3 Fatty Acids on the DU–145 Transplantable Human Prostatic Tumor," *Anticancer Res. 7*:1173–1180.
Kozlowski, J.M., et al., 1984, "Metastatic Behavior of Human Tumor Cell Lines Grown in the Nude Mouse," *Cancer Research 44*:3522–3529.
Leder, A., et al., 1986, "Consequences of widespread deregulation of the C–MYC gene in transgenic mice: multiple neoplasms and normal development," *Cell 45*:485–495.
Leone, A., et al., 1991, "Reduced Tumor Incidence, Metastatic Potential, and Cytokine Responsiveness of nm23–Transfected Melanoma Cells," 65:25–35.
Liotta, L.A., et al., 1991, "Cancer metastasis and angiogenesis: an imbalance of positive and negative regulation," *Cell 64*:327.
Mintz, B., and Silvers, W.K., 1993, "Transgenic mouse model of malignant skin melanoma," *Proc. Natl. Acad. Sci. USA 90*:8817–8821.
Morikawa K., et al., 1988, "*In Vivo* Selection of Highly Metastatic Cells from Surgical Specimens of Different Primary Human Colon Carcinomas Implanted into Nude Mice," *Cancer Research 48*:1943–1948.
Qian, F., et al., 1994, "Expression of the integrin α4β1 on Melanoma Cells Can Inhibit the Invasive Stage of Metastasis Formation," *Cell 77*:335–347.
Rose, D.P., et al., 1993, "Effects of Dietary Omega–3 Fatty Acids on Human Breast Cancer Growth and Metastases in Nude Mice," *J. Natl. Cancer Inst. 85*:1743–1747.
Schrier, P.I., et al., 1983, Expression of Class 1 major histocompatibility antigens switched off by highly oncogenic adenovirus 12 in transformed rat cells, *Nature 305*:771.
Steeg, P.S., et al., 1988, "Evidence for a Novel Gene Associated With Low Tumor Metastatic Potential," *J. Natl. Cancer Inst. 80*:200–204.
Tanaka et al., "Construction of a Human Cytochrome c Gene and Its Functional Expression in *Saccnaromces cerevisiae", J. Biochem., 103*:954–961 (1988).
Van der Bruggen, P., et al., 1991, "A Gene Encoding an Antigen Recognized by Cytolytic T Lymphocytes on a Human Melanoma," *Science 254*:1643–1667.
Vogelstein, B., and Kinzler, K.W., 1993, "The Multistep Nature of Cancer," *Trends Genet. 9*:138–141.
Watts C.K., et al., 1994, "Antiestrogen regulation of cell cycle progression and cyclin D1 gene expression in MCF–7 human breast cancer cells," *Breast Cancer Res. Treat. 31*:95–105.
Wilson et al., "2.2 Mb of contiguous nucleotide sequence from chromosome III of C. elegans", *Nature, 368*:32–38 (1994).
Zou, Z., et al., 1994, "Maspin, A Serpin with Tumor–Suppressing Activity in Human Mammary Epithelial Cells," *Science 263*:526–529.
GenBank Accession No. N42635, Hillier et al., Jan. 25, 1996.
GenBank Accession No. N32151, Hillier et al., Jan. 10, 1996.
GenBank Accession No. N24756, Hillier et al., Dec. 28, 1995.
GenBank Accession No. N24164, Hillier et al., Dec. 28, 1995.
GenBank Accession No. H98055, Hillier et al., Dec. 12, 1995.
GenBank Accession No. N22835, Hillier et al., Dec. 28, 1995.
Wang et al., "Identification and Molecular Cloning of Tactile" J. of Immun. 148(8):2600–2608, 1992.
Duncan et al., "Fomy030 expression in melanocytic proliferations." Melanoma Res. 7(1):S7, 1997.
Hillier et al., "AC No. N42635. Homosapiens cDNA 270851" EMBL. Sequence Database, Heidelberg, Germany, Jan. 28, 1996.
Hillier et al., "AC No. N42983. Homosapiens cDNA clone 270601" EMBL Sequence Database, Heidelberg, Germany, Jan. 28, 1996.

* cited by examiner romy030

GGTGCTGGAGTACCTCATGGGCGGTGCCTACCGCTGCAACTACACTCGGAAAAGCTTCCGGACTCT
CTACAACAACTTGTTTGGCCCTAAGAGGGTAGAGCTCAGCAGACACACAGTGTCCTGTGCCTCCC
AGAGTAACATGTGGTTCCTTGATGTGCTTCCCCAAAAGCCCACCTGTGCAGAATG
(SEQ ID NO: 1)

FIG. 2

```
AAGGAGGCTAGGCTGCACCCTTCCCGCTTGCTCAGCAGCTGAGGCAGGGTCAGAAAGCATGGATAGAGAAGACATTTTGC    80
AAAAGGGAATGCATCTTTGTAATTCCCAGTACAAAAGACCCTAACAGATGTTGCTGTGGTCAGCTCACTAACCAGCACAT   160
CCCCCCTTTGCCGAGTGGGGCTCCCAGCACAACAGGAGAGGACACCAAGCAGGCAGACACGCAGTCCGGGAAATGGTCTG   240
TCAGCAAACACACCCAGAGCTACCCAACAGACTCCTATGGGATTCTTGAATTCCAGGGTGGGGTTACTCCAATAAAGCC   320

ATG TAC ATC CGA GTC TCC TAC GAC ACC AAG CCA GAT TCC CTG CTC CAC CTC ATG GTG AAG   380
 M   Y   I   R   V   S   Y   D   T   K   P   D   S   L   L   H   L   M   V   K     20

GAC TGG CAG CTG GAG CTC CCG AAG CTC TTG ATA TCT GTG CAC GGA GGC CTC CAA AGC TTC   440
 D   W   Q   L   E   L   P   K   L   L   I   S   V   H   G   G   L   Q   S   F     40

GAG ATG CAG TCC AAA CTG AAG CAG GTG TTT GGG AAA GGT CTG ATC AAG GCT GCC ATG ACC   500
 E   M   Q   S   K   L   K   Q   V   F   G   K   G   L   I   K   A   A   M   T     60

ACG GGG GCG TGG ATC TTC ACC GGG GGT GTG AGC ACT GGT GTC GTC AGC CAT GTG GGG GAT   560
 T   G   A   W   I   F   T   G   G   V   S   T   G   V   V   S   H   V   G   D     80

GCC TTG AAA GAC CAC TCC TCC AAG TCC AGA GGC CGG CTC TGT GCT ATA GGA ATT GCT CCC   620
 A   L   K   D   H   S   S   K   S   R   G   R   L   C   A   I   G   I   A   P    100

TGG GGC ATG GTG GAG AAC AAG GAA GAC CTG ATT GGA AAA GAT GTA ACA AGA GTC TAT CAG   680
 W   G   M   V   E   N   K   E   D   L   I   G   K   D   V   T   R   V   Y   Q    120

ACC ATG TCC AAC CCT CTG AGC AAG CTC TCT GTG CTC AAC AAT TCC CAC ACT CAC TTC ATC   740
 T   M   S   N   P   L   S   K   L   S   V   L   N   N   S   H   T   H   F   I    140

TTG GCT GAC AAC GGC ACC CTG GGC AAG TAT GGT GCT GAG GTG AAG CTT CGA AGA CAG CTG   800
 L   A   D   N   G   T   L   G   K   Y   G   A   E   V   K   L   R   R   Q   L    160

GAA AAA CAC ATC TCC CTG CAG AAG ATC AAC ACA AGG CTG GGC CAG GGT GTA CCT GTC GTG   860
 E   K   H   I   S   L   Q   K   I   N   T   R   L   G   Q   G   V   P   V   V    180

GGC CTA GTG GTA GAA GGT GGT CCT AAC GTG GTT TCT ATC GTC CTG GAG TAT CTC AAA GAA   920
 G   L   V   V   E   G   G   P   N   V   V   S   I   V   L   E   Y   L   K   E    200
```

FIG. 3A

GAC CCT CCT GTC CCT GTG GTG GTT TGC GAT GGC AGT GGA CGT GCC TCT GAC ATT TTG TCC 980
D P P V P V V V C D G S G R A S D I L S 220

TTC GCA CAC AAA TAC TGC GAC GAA GGA GGA GTC ATA AAC GAG TCC CTG CGG GAC CAG CTT 1040
F A H K Y C D E G G V I N E S L R D Q L 240

CTA GTT ACC ATT CAG AAA ACA TTT AAT TAC AGC AAG TCC CAG TCG TAT CAG CTG TTT GCA 1100
L V T I Q K T F N Y S K S Q S Y Q L F A 260

ATT ATC ATG GAG TGC ATG AAG AAG AAA GAA CTC GTC ACT GTG TTT CGG ATG GGT TCC GAG 1160
I I M E C M K K K E L V T V F R M G S E 280

GGT CAG CAA GAT GTC GAG ATG GCA ATT TTA ACT GCC TTG CTC AAA GGA ACC AAC GCA TCA 1220
G Q Q D V E M A I L T A L L K G T N A S 300

GCT CCA GAT CAG CTG AGC TTG GCC CTG GCT TGG AAC CGG GTC GAC ATA GCG CGA AGC CAG 1280
A P D Q L S L A L A W N R V D I A R S Q 320

ATC TTC GTC TTT GGC CCA CAC TGG CCG CCA CTG GGA AGC CTG GCC CCT CCT GTG GAC ACC 1340
I F V F G P H W P P L G S L A P P V D T 340

AAA GCC GCA GAG AAG GAA AAG AAG CCA CCC ACA GCC ACC ACC AAG GGG AGA GGA AAA GGA 1400
K A A E K E K K P P T A T T K G R G K G 360

AAA GGC AAG AAG AAA GGC AAA GTG AAA GAG GAA GTG GAG GAA GAG ACG GAC CCC CGG AAG 1460
K G K K K G K V K E E V E E E T D P R K 380

FIG. 3B

```
CTT GAG CTG CTC AAC TGG GTG AAT GCC CTG GAG CAA GCC ATG CTG GAT GCT CTT GTC CTA   1520
L   E   L   L   N   W   V   N   A   L   E   Q   A   M   L   D   A   L   V   L      400

GAT CGG GTG GAC TTT GTA AAG CTC CTG ATT GAA AAC GGA GTG AAC ATG CAG CAT TTC CTC   1580
D   R   V   D   F   V   K   L   L   I   E   N   G   V   N   M   Q   H   F   L      420

ACC ATC CCG AGG CTG GAG GAG CTA TAC AAC ACC AGA CTG GGC CCA CCA AAC ACC CTT CAT   1640
T   I   P   R   L   E   E   L   Y   N   T   R   L   G   P   P   N   T   L   H      440

CTG CTG GTG CGG GAT GTA AAG AAG AGC AAC CTT CCA CCT GAT TAC CAC ATC AGC CTC ATT   1700
L   L   V   R   D   V   K   K   S   N   L   P   P   D   Y   H   I   S   L   I      460

GAT ATA GGA CTG GTG CTG GAG TAC CTC ATG GGC GGT GCC TAC CGC TGC AAC TAC ACT CGG   1760
D   I   G   L   V   L   E   Y   L   M   G   G   A   Y   R   C   N   Y   T   R      480

AAA AGC TTC CGG ACT CTC TAC AAC AAC TTG TTT GGC CCT AAG AGG GTA GAG CTC AGC AGA   1820
K   S   F   R   T   L   Y   N   N   L   F   G   P   K   R   V   E   L   S   R      500

CAC ACA GTG TCC TGT GCC TCC CAG AGT AAC ATG TGG TTC CTT GAT GTG CTT CCC CAA AAG   1880
H   T   V   S   C   A   S   Q   S   N   M   W   F   L   D   V   L   P   Q   K      520

CCC ACC TGT GCA GAA TGC AAC TCT TCA CCT CAC CTG TCC CAA ACT GAC ATC ACC CCA CCT   1940
P   T   C   A   E   C   N   S   S   P   H   L   S   Q   T   D   I   T   P   P      540

CTG CCC TGA CACCCAGTGCAGGGCCTCCTAGCTTTCACATGCAGCCATTCACATCGCCTCTCAAGACTGGGCCAGGC  2018
L   P   *                                                              (SEQ ID NO: 3)

AGTGCAACCTGTCAAGCATGTCTGTCCTCCCCTCCTTCCTACAATAGCCCCCCCTCTGGGCCCCATGCCTCTGCTCTCTC  2098
AGCCCGTTCTCCTCCCCACTGATCACTGGCGCTCCTGTTGTCTTCCAAGGCAAGGAACAAGGAAAAGCATCTTTTTGCCC  2178
ACAAAAGTTTAGGGCTCCCCGCTGTTCAACCATAGCCAACCTCACTGTACATCGGAGTCATCCAGGCCAGCTGCCACACA  2258
CAAGCCTTCCCCACCCTATCCCAATAGACCCTATTCCTCCATCAAAATCAAAGCTAACTCCTGGCCTGCCACATTGCTTC  2338
TTCTTGCTCCAGCCTGTTAAACCTCCAATAAATGTCAGATCTGTGGGAAGCCTTCCTCACTCTCACTCCACAGTTTGTAC  2418
AGAGAGCGAGAGCCTCGTTTGGTTCTACTTACAAGGAAGGCTTTGTGTCTGTCTGTCCTTCCCAACTGACTTCTGTTGAC  2498
AGAAGCAGTTTCCACATGAAAGCGTTGACTCACCTGGATGTTGTCATTAATTAATAGTGATACAAAATATTGACACTTCT  2578
TTTCCTGCTTCTTTGTTATGCAGCCGAAAGCACTTAAGCTTCTGGGAATGGAAGTAAGTAGGACATGTTTGTGGCAGTTT  2658
ATTTACTATATATACCTTTGTCATTCTGTGGAAGCAAAAATTGCAATGTTTTCCATGAATAAAGCTCGTGCC         2730
                                                                       (SEQ ID NO: 2)
```

FIG. 3C

ACTCATTATAGGGNTCGAGCGGCCGCCCGGGCAGGTTTGAGCTGTGCCCTCTCCATTCCACTGCTGTGGCAGGGTCAGA
AATCTTGGATAGAGAAAACCTTTTGCAAACGGGAATGTATCTTTGTAATTCCTAGCACGAAAGACTCTAACAGGTGTTG
CTGTGGCCAGTTCACCAACCAGCATATCCCCCCTCTGCCAAGTGCAACACCCAGCAAAAATGAAGAGGAAAGCAAACAG
GTGGAGACTCAGCCTGAGAAATGGTCTGTTGCAAGCACACCCAGAGCTACCCAACAGATTCCTATGGAGTTCTTGAATT
CCAGGGTGGCGGATATTCCAATAAAGCC

```
M   Y   I   R   V   S   Y   D   T   K   P   D   S   L   L   H   L   M   V   K      20
ATG TAT ATC CGT GTA TCC TAT GAC ACC AAG CCA GAC TCA CTG CTC CAT CTC ATG GTG AAA    60

D   W   Q   L   E   L   P   K   L   L   I   S   V   H   G   G   L   Q   N   F      40
GAT TGG CAG CTG GAA CTC CCC AAG CTC TTA ATA TCT GTG CAT GGA GGC CTC CAG AAC TTT   120

E   M   Q   P   K   L   K   Q   V   F   G   K   G   L   I   K   A   A   M   T      60
GAG ATG CAG CCC AAG CTG AAA CAA GTC TTT GGG AAA GGC CTG ATC AAG GCT GCT ATG ACC   180

T   G   A   W   I   F   T   G   G   V   S   T   G   V   I   S   H   V   G   D      80
ACC GGG GCC TGG ATC TTC ACC GGG GGT GTC AGC ACA GGT GTT ATC AGC CAC GTA GGG GAT   240

A   L   K   D   H   S   S   K   S   R   G   R   V   C   A   I   G   I   A   P     100
GCC TTG AAA GAC CAC TCC TCC AAG TCC AGA GGC CGG GTT TGT GCT ATA GGA ATT GCT CCA   300

W   G   I   V   E   N   K   E   D   L   V   G   K   D   V   T   R   V   Y   Q     120
TGG GGC ATC GTG GAG AAT AAG GAA GAC CTG GTT GGA AAG GAT GTA ACA AGA GTG TAC CAG   360

T   M   S   N   P   L   S   K   L   S   V   L   N   N   S   H   T   H   F   I     140
ACC ATG TCC AAC CCT CTA AGT AAG CTC TCT GTG CTC AAC AAC TCC CAC ACC CAC TTC ATC   420

L   A   D   N   G   T   L   G   K   Y   G   A   E   V   K   L   R   R   L   L     160
CTG GCT GAC AAT GGC ACC CTG GGC AAG TAT GGC GCC GAG GTG AAG CTG CGA AGG CTG CTG   480

E   K   H   I   S   L   Q   K   I   N   T   R   L   G   Q   G   V   P   L   V     180
GAA AAG CAC ATC TCC CTC CAG AAG ATC AAC ACA AGA CTG GGG CAG GGC GTG CCC CTC GTG   540

G   L   V   V   E   G   G   P   N   V   V   S   I   V   L   E   Y   L   Q   E     200
GGT CTC GTG GTG GAG GGG GGC CCT AAC GTG GTG TCC ATC GTC TTG GAA TAC CTG CAA GAA   600
```

FIG. 5A

```
 E   P   P   I   P   V   V   I   C   D   G   S   G   R   A   S   D   I   L   S    220
GAG CCT CCC ATC CCT GTG GTG ATT TGT GAT GGC AGC GGA CGT GCC TCG GAC ATC CTG TCC   660

 F   A   H   K   Y   C   E   E   G   G   I   I   N   E   S   L   R   E   Q   L    240
TTT GCG CAC AAG TAC TGT GAA GAA GGC GGA ATA ATA AAT GAG TCC CTC AGG GAG CAG CTT   720

 L   V   T   I   Q   K   T   F   N   Y   N   K   A   Q   S   H   Q   L   F   A    260
CTA GTT ACC ATT CAG AAA ACA TTT AAT TAT AAT AAG GCA CAA TCA CAT CAG CTG TTT GCA   780

 I   I   M   E   C   M   K   K   K   E   L   V   T   V   F   R   M   G   S   E    280
ATT ATA ATG GAG TGC ATG AAG AAG AAA GAA CTC GTC ACT GTG TTC AGA ATG GGT TCT GAG   840

 G   Q   Q   D   I   E   M   A   I   L   T   A   L   L   K   G   T   N   V   S    300
GGC CAG CAG GAC ATC GAG ATG GCA ATT TTA ACT GCC CTG CTG AAA GGA ACA AAC GTA TCT   900

 A   P   D   Q   L   S   L   A   L   A   W   N   R   V   D   I   A   R   S   Q    320
GCT CCA GAT CAG CTG AGC TTG GCA CTG GCT TGG AAC CGC GTG GAC ATA GCA CGA AGC CAG   960

 I   F   V   F   G   P   H   W   T   P   L   G   S   L   A   P   P   T   D   S    340
ATC TTT GTC TTT GGG CCC CAC TGG ACG CCC CTG GGA AGC CTG GCA CCC CCG ACG GAC AGC  1020

 K   A   T   E   K   E   K   K   P   P   M   A   T   T   K   G   G   R   G   K    360
AAA GCC ACG GAG AAG GAG AAG AAG CCA CCC ATG GCC ACC ACC AAG GGA GGA AGA GGA AAA  1080

 G   K   G   K   K   K   G   K   V   K   E   E   V   E   E   E   T   D   P   R    380
GGG AAA GGC AAG AAG AAA GGG AAA GTG AAA GAG GAA GTG GAG GAA GAA ACT GAC CCC CGG  1140

 K   I   E   L   L   N   W   V   N   A   L   E   Q   A   M   L   D   A   L   V    400
```

```
AAG ATA GAG CTG CTG AAC TGG GTG AAT GCT TTG GAG CAA GCG ATG CTA GAT GCT TTA GTC   1200

 L   D   R   V   D   F   V   K   L   L   I   E   N   G   V   N   M   Q   H   F    420
TTA GAT CGT GTC GAC TTT GTG AAG CTC CTG ATT GAA AAC GGA GTG AAC ATG CAA CAC TTT   1260

 L   T   I   P   R   L   E   E   L   Y   N   T   R   L   G   P   P   N   T   L    440
CTG ACC ATT CCG AGG CTG GAG GAG CTT TAT AAC ACA AGA CTG GGT CCA CCA AAC ACA CTT   1320

 H   L   L   V   R   D   V   K   K   S   N   L   P   P   D   Y   H   I   S   L    460
CAT CTG CTG GTG AGG GAT GTG AAA AAG AGC AAC CTT CCG CCT GAT TAC CAC ATC AGC CTC   1380

 I   D   I   G   L   V   L   E   Y   L   M   G   G   A   Y   R   C   N   Y   T    480
ATA GAC ATC GGG CTC GTG CTG GAG TAC CTC ATG GGA GGA GCC TAC CGC TGC AAC TAC ACT   1440

 R   K   N   F   R   T   L   Y   N   N   L   F   G   P   K   R   P   K   A   L    500
CGG AAA AAC TTT CGG ACC CTT TAC AAC AAC TTG TTT GGA CCA AAG AGG CCT AAA GCT CTT   1500

 K   L   L   G   M   E   D   D   E   P   P   A   K   G   K   K   K   K   K   K    520
AAA CTT CTG GGA ATG GAA GAT GAT GAG CCT CCA GCT AAA GGG AAG AAA AAA AAA AAA AAG   1560

 K   K   E   E   E   I   D   I   D   V   D   D   P   A   V   S   R   F   Q   Y    540
AAA AAG GAG GAA GAG ATC GAC ATT GAT GTG GAC GAC CCT GCC GTG AGT CGG TTC CAG TAT   1620

 P   F   H   E   L   M   V   W   A   V   L   M   K   R   Q   K   M   A   V   F    560
CCC TTC CAC GAG CTG ATG GTG TGG GCA GTG CTG ATG AAA CGC CAG AAA ATG GCA GTG TTC   1680

 L   W   Q   R   G   E   E   S   M   A   K   A   L   V   A   C   K   L   Y   K    580
CTC TGG CAG CGA GGG GAA GAG AGC ATG GCC AAG GCC CTG GTG GCC TGC AAG CTC TAC AAG   1740

 A   M   A   H   E   S   S   E   S   D   L   V   D   D   I   S   Q   D   L   D    600
GCC ATG GCC CAC GAG TCC TCC GAG AGT GAT CTG GTG GAT GAC ATC TCC CAG GAC TTG GAT   1800

 N   N   S   K   D   F   G   Q   L   A   L   E   L   L   D   Q   S   Y   K   H    620
AAC AAT TCC AAA GAC TTC GGC CAG CTT GCT TTG GAG TTA TTA GAC CAG TCC TAT AAG CAT   1860
```

GAC GAG CAG ATC GCT ATG AAA CTC CTG ACC TAC GAG CTG AAA AAC TGG AGC AAC TCG ACC 1920

C L K L A V A A K H R D F I A H T C S Q 660

TGC CTC AAA CTG GCC GTG GCA GCC AAA CAC CGG GAC TTC ATT GCT CAC ACC TGC AGC CAG 1980

M L L T D M W M G R L R M R K N P G L K 680

ATG CTG CTG ACC GAT ATG TGG ATG GGA AGA CTG CGG ATG CGG AAG AAC CCC GGC CTG AAG 2040

V I M G I L L P P T I L F L E F R T Y D 700

GTT ATC ATG GGG ATT CTT CTA CCC CCC ACC ATC TTG TTT TTG GAA TTT CGC ACA TAT GAT 2100

D F S Y Q T S K E N E D G K E K E E E N 720

GAT TTC TCG TAT CAA ACA TCC AAG GAA AAC GAG GAT GGC AAA GAA AAA GAA GAG GAA AAT 2160

T D A N A D A G S R K G D E E N E H K K 740

ACG GAT GCA AAT GCA GAT GCT GGC TCA AGA AAG GGG GAT GAG GAG AAC GAG CAT AAA AAA 2220

Q R I I P I G T K I C K F Y N A P I V K 760

CAA AGA ATT ATC CCC ATC GGA ACA AAA ATC TGT AAA TTC TAT AAC GCG CCC ATT GTC AAG 2280

F W F Y T I S Y L G Y L L L F N Y V I L 780

TTC TGG TTT TAC ACA ATA TCA TAC TTG GGC TAC CTG CTG CTG TTT AAC TAC GTC ATC CTG 2340

V R M D G W P S L Q E W I V I S Y I V S 800

GTG CGG ATG GAT GGC TGG CCG TCC CTC CAG GAG TGG ATC GTC ATC TCC TAC ATC GTG AGC 2400

L A L E K I R E I L M S E P G K L S Q K 820

CTG GCG TTA GAG AAG ATA CGA GAG ATC CTC ATG TCA GAA CCA GGC AAA CTC AGC CAG AAA 2460

FIG. 5D

```
 I   K   V   W   L   Q   E   Y   W   N   I   T   D   L   V   A   I   S   T   F     840
ATC AAA GTT TGG CTT CAG GAG TAC TGG AAC ATC ACA GAT CTC GTG GCC ATT TCC ACA TTC   2520

 M   I   G   A   M   A   T   R   S   V   M   M   I   G   K   M   M   I   D   M     860
ATG ATT GGA GCA ATG GCC ACG AGA TCT GTG ATG ATG ATT GGA AAG ATG ATG ATC GAC ATG   2580

 L   Y   F   V   V   I   M   L   V   V   L   M   S   F   G   V   A   R   Q   A     880
CTG TAC TTT GTG GTC ATC ATG CTG GTC GTG CTC ATG AGT TTC GGA GTA GCC CGT CAA GCC   2640

 I   L   H   P   E   E   K   P   S   W   K   L   A   R   N   I   F   Y   M   P     900
ATT CTG CAT CCA GAG GAG AAG CCC TCT TGG AAA CTG GCC CGA AAC ATC TTC TAC ATG CCC   2700

 Y   W   M   I   Y   G   E   V   F   A   D   Q   I   D   L   Y   A   M   E   I     920
TAC TGG ATG ATC TAT GGA GAG GTG TTT GCA GAC CAG ATA GAC CTC TAC GCC ATG GAA ATT   2760

 N   P   P   C   G   E   N   L   Y   D   E   E   G   K   R   L   P   P   C   I     940
AAT CCT CCT TGT GGT GAG AAC CTA TAT GAT GAG GAG GGC AAG CGG CTT CCT CCC TGT ATC   2820

 P   G   A   W   L   T   P   A   L   M   A   C   Y   L   L   V   A   N   I   L     960
CCC GGC GCC TGG CTC ACT CCA GCA CTC ATG GCG TGC TAT CTA CTG GTC GCC AAC ATC CTG   2880

 L   V   N   L   L   I   A   V   F   N   N   T   F   F   E   V   K   S   I   S     980
CTG GTG AAC CTG CTG ATT GCT GTG TTC AAC AAT ACC TTC TTT GAA GTA AAA TCA ATA TCC   2940

 N   Q   V   W   K   F   Q   R   Y   Q   L   I   M   T   F   H   D   R   P   V    1000
AAC CAG GTG TGG AAG TTC CAG CGA TAT CAG CTG ATT ATG ACA TTT CAT GAC AGG CCA GTC   3000

 L   P   P   P   M   I   I   L   S   H   I   Y   I   I   I   M   R   L   S   G    1020
CTG CCC CCA CCG ATG ATC ATT TTA AGC CAC ATC TAC ATC ATC ATT ATG CGT CTC AGC GGC   3060

 R   C   R   K   K   R   E   G   D   Q   E   E   R   D   R   G   L   K   L   F    1040
CGC TGC AGG AAA AAG AGA GAA GGG GAC CAA GAG GAA CGG GAT CGT GGA TTG AAG CTC TTC   3120
```

FIG. 5E

```
 L   S   D   E   E   L   K   R   L   H   E   F   E   E   Q   C   V   Q   E   H    1060
CTT AGC GAC GAG GAG CTA AAG AGG CTG CAT GAG TTC GAG GAG CAG TGC GTG CAG GAG CAC   3180

 F   R   E   K   E   D   E   Q   Q   S   S   S   D   E   R   I   R   V   T   S    1080
TTC CGG GAG AAG GAG GAT GAG CAG CAG TCG TCC AGC GAC GAG CGC ATC CGG GTC ACT TCT   3240

 E   R   V   E   N   M   S   M   R   L   E   E   I   N   E   R   E   T   F   M    1100
GAA AGA GTT GAA AAT ATG TCA ATG AGG TTG GAA GAA ATC AAT GAA AGA GAA ACT TTT ATG   3300

 K   T   S   L   Q   T   V   D   L   R   L   A   Q   L   E   E   L   S   N   R    1120
AAA ACT TCC CTG CAG ACT GTT GAC CTT CGA CTT GCT CAG CTA GAA GAA TTA TCT AAC AGA   3360

 M   V   N   A   L   E   N   L   A   G   I   D   R   S   D   L   I   Q   A   R    1140
ATG GTG AAT GCT CTT GAA AAT CTT GCG GGA ATC GAC AGG TCT GAC CTG ATC CAG GCA CGG   3420

 S   R   A   S   S   E   C   E   A   T   Y   L   L   R   Q   S   S   I   N   S    1160
TCC CGG GCT TCT TCT GAA TGT GAG GCA ACG TAT CTT CTC CGG CAA AGC AGC ATC AAT AGC   3480

 A   D   G   Y   S   L   Y   R   Y   H   F   N   G   E   E   L   L   F   E   D    1180
GCT GAT GGC TAC AGC TTG TAT CGA TAT CAT TTT AAC GGA GAA GAG TTA TTA TTT GAG GAT   3540

 T   S   L   S   T   S   P   G   T   G   V   R   K   K   T   C   S   F   R   I    1200
ACA TCT CTC TCC ACG TCA CCA GGG ACA GGA GTC AGG AAA AAA ACC TGT TCC TTC CGT ATA   3600

 K   E   E   K   D   V   K   T   H   L   V   P   E   C   Q   N   S   L   H   L    1220
AAG GAA GAG AAG GAC GTG AAA ACG CAC CTA GTC CCA GAA TGT CAG AAC AGT CTT CAC CTT   3660

 S   L   G   T   S   T   S   A   T   P   D   G   S   H   L   A   V   D   D   L    1240
TCA CTG GGC ACA AGC ACA TCA GCA ACC CCA GAT GGC AGT CAC CTT GCA GTA GAT GAC TTA   3720
```

FIG. 5F

```
 K   N   A   E   E   S   K   L   G   P   D   I   G   I   S   K   E   D   D   E     1260
AAG AAC GCT GAA GAG TCA AAA TTA GGT CCA GAT ATT GGG ATT TCA AAG GAA GAT GAT GAA    3780

 R   Q   T   D   S   K   K   E   E   T   I   S   P   S   L   N   K   T   D   V     1280
AGA CAG ACA GAC TCT AAA AAA GAA GAA ACT ATT TCC CCA AGT TTA AAT AAA ACA GAT GTG    3840

 I   H   G   Q   D   K   S   D   V   Q   N   T   Q   L   T   V   E   T   T   N     1300
ATA CAT GGA CAG GAC AAA TCA GAT GTT CAA AAC ACT CAG CTA ACA GTG GAA ACG ACA AAT    3900

 I   E   G   T   I   S   Y   P   L   E   E   T   K   I   T   R   Y   F   P   D     1320
ATA GAA GGC ACT ATT TCC TAT CCC CTG GAA GAA ACC AAA ATT ACA CGC TAT TTC CCC GAT    3960

 E   T   I   N   A   C   K   T   M   K   S   R   S   F   V   Y   S   R   G   R     1340
GAA ACG ATC AAT GCT TGT AAA ACA ATG AAG TCC AGA AGC TTC GTC TAT TCC CGG GGA AGA    4020

 K   L   V   G   G   V   N   Q   D   V   E   Y   S   S   I   T   D   Q   Q   L     1360
AAG CTG GTC GGT GGG GTT AAC CAG GAT GTA GAG TAC AGT TCA ATC ACG GAC CAG CAA TTG    4080

 T   T   E   W   Q   C   Q   V   Q   K   I   T   R   S   H   S   T   D   I   P     1380
ACG ACG GAA TGG CAA TGC CAA GTT CAA AAG ATC ACG CGC TCT CAT AGC ACA GAT ATT CCT    4140

 Y   I   V   S   E   A   A   V   Q   A   E   Q   K   E   Q   F   A   D   M   Q     1400
TAC ATT GTG TCG GAA GCT GCA GTG CAA GCT GAG CAA AAA GAG CAG TTT GCA GAT ATG CAA    4200

 D   E   H   H   V   A   E   A   I   P   R   I   P   R   L   S   L   T   I   T     1420
GAT GAA CAC CAT GTC GCT GAA GCA ATT CCT CGA ATC CCT CGC TTG TCC CTA ACC ATT ACT    4260

 D   R   N   G   M   E   N   L   L   S   V   K   P   D   Q   T   L   G   F   P     1440
GAC AGA AAT GGG ATG GAA AAC TTA CTG TCT GTG AAG CCA GAT CAA ACT TTG GGA TTC CCA    4320

 S   L   R   S   K   S   L   H   G   H   P   R   N   V   K   S   I   Q   G   K     1460
TCT CTC AGG TCA AAA AGT TTA CAT GGA CAT CCT AGG AAT GTG AAA TCC ATT CAG GGA AAG    4380

 L   D   R   S   G   H   A   S   S   V   S   S   L   V   I   V   S   G   M   T     1480
TTA GAC AGA TCT GGA CAT GCC AGT AGT GTA AGC AGC TTA GTA ATT GTG TCT GGA ATG ACA    4440

 A   E   E   K   K   V   K   K   E   K   A   S   T   E   T   E   C  (SEQ ID NO: 7)  1497
GCA GAA GAA AAA AAG GTT AAG AAA GAG AAA GCT TCC ACA GAA ACT GAA TGC TAG TCTGTT     4991

TTGTTTCTTTAATTTTTTTTTTTAACAGTCAGAACCACTAATGGGTGTCATCTTGGCCATCCTAAACATCCATCCAAT

TTCCTAAAAACATTTTCCCT   (SEQ ID NO: 6)
```

FIG. 5G

```
ACTCATTATAGGGNTCGAGCGGCCGCCCGGGCAGGTTTGAGCTGTGCCCTCTCCATTCCACTGCTGTGGCAGGGTCAGA
AATCTTGGATAGAGAAAACCTTTTGCAAACGGGAATGTATCTTTGTAATTCCTAGCACGAAAGACTCTAACAGGTGTTG
CTGTGGCCAGTTCACCAACCAGCATATCCCCCCTCTGCCAAGTGCAACACCCAGCAAAAATGAAGAGGAAAGCAAACAG
GTGGAGACTCAGCCTGAGAAATGGTCTGTTGCAAGCACACCCAGAGCTACCCAACAGATTCCTATGGAGTTCTTGAATT
CCAGGGTGGCGGATATTCCAATAAAGCC

 M   Y   I   R   V   S   Y   D   T   K   P   D   S   L   L   H   L   M   V   K     20
ATG TAT ATC CGT GTA TCC TAT GAC ACC AAG CCA GAC TCA CTG CTC CAT CTC ATG GTG AAA    60

 D   W   Q   L   E   L   P   K   L   L   I   S   V   H   G   G   L   Q   N   F     40
GAT TGG CAG CTG GAA CTC CCC AAG CTC TTA ATA TCT GTG CAT GGA GGC CTC CAG AAC TTT   120

 E   M   Q   P   K   L   K   Q   V   F   G   K   G   L   I   K   A   A   M   T     60
GAG ATG CAG CCC AAG CTG AAA CAA GTC TTT GGG AAA GGC CTG ATC AAG GCT GCT ATG ACC   180

 T   G   A   W   I   F   T   G   G   V   S   T   G   V   I   S   H   V   G   D     80
ACC GGG GCC TGG ATC TTC ACC GGG GGT GTC AGC ACA GGT GTT ATC AGC CAC GTA GGG GAT   240

 A   L   K   D   H   S   S   K   S   R   G   R   V   C   A   I   G   I   A   P    100
GCC TTG AAA GAC CAC TCC TCC AAG TCC AGA GGC CGG GTT TGT GCT ATA GGA ATT GCT CCA   300

 W   G   I   V   E   N   K   E   D   L   V   G   K   D   V   T   R   V   Y   Q    120
TGG GGC ATC GTG GAG AAT AAG GAA GAC CTG GTT GGA AAG GAT GTA ACA AGA GTG TAC CAG   360

 T   M   S   N   P   L   S   K   L   S   V   L   N   N   S   H   T   H   F   I    140
ACC ATG TCC AAC CCT CTA AGT AAG CTC TCT GTG CTC AAC AAC TCC CAC ACC CAC TTC ATC   420

 L   A   D   N   G   T   L   G   K   Y   G   A   E   V   K   L   R   R   L   L    160
CTG GCT GAC AAT GGC ACC CTG GGC AAG TAT GGC GCC GAG GTG AAG CTG CGA AGG CTG CTG   480

 E   K   H   I   S   L   Q   K   I   N   T   R   L   G   Q   G   V   P   L   V    180
GAA AAG CAC ATC TCC CTC CAG AAG ATC AAC ACA AGA CTG GGG CAG GGC GTG CCC CTC GTG   540

 G   L   V   V   E   G   G   P   N   V   V   S   I   V   L   E   Y   L   Q   E    200
GGT CTC GTG GTG GAG GGG GGC CCT AAC GTG GTG TCC ATC GTC TTG GAA TAC CTG CAA GAA   600
```

FIG. 6A

```
 E   P   P   I   P   V   V   I   C   D   G   S   G   R   A   S   D   I   L   S     220
GAG CCT CCC ATC CCT GTG GTG ATT TGT GAT GGC AGC GGA CGT GCC TCG GAC ATC CTG TCC    660

 F   A   H   K   Y   C   E   E   G   G   I   I   N   E   S   L   R   E   Q   L     240
TTT GCG CAC AAG TAC TGT GAA GAA GGC GGA ATA ATA AAT GAG TCC CTC AGG GAG CAG CTT    720

 L   V   T   I   Q   K   T   F   N   Y   N   K   A   Q   S   H   Q   L   F   A     260
CTA GTT ACC ATT CAG AAA ACA TTT AAT TAT AAT AAG GCA CAA TCA CAT CAG CTG TTT GCA    780

 I   I   M   E   C   M   K   K   K   E   L   V   T   V   F   R   M   G   S   E     280
ATT ATA ATG GAG TGC ATG AAG AAG AAA GAA CTC GTC ACT GTG TTC AGA ATG GGT TCT GAG    840

 G   Q   Q   D   I   E   M   A   I   L   T   A   L   L   K   G   T   N   V   S     300
GGC CAG CAG GAC ATC GAG ATG GCA ATT TTA ACT GCC CTG CTG AAA GGA ACA AAC GTA TCT    900

 A   P   D   Q   L   S   L   A   L   A   W   N   R   V   D   I   A   R   S   Q     320
GCT CCA GAT CAG CTG AGC TTG GCA CTG GCT TGG AAC CGC GTG GAC ATA GCA CGA AGC CAG    960

 I   F   V   F   G   P   H   W   T   P   L   G   S   L   A   P   P   T   D   S     340
ATC TTT GTC TTT GGG CCC CAC TGG ACG CCC CTG GGA AGC CTG GCA CCC CCG ACG GAC AGC   1020

 K   A   T   E   K   E   K   K   P   P   M   A   T   T   K   G   G   R   G   K     360
AAA GCC ACG GAG AAG GAG AAG AAG CCA CCC ATG GCC ACC ACC AAG GGA GGA AGA GGA AAA   1080

 G   K   G   K   K   K   G   K   V   K   E   E   V   E   E   E   T   D   P   R     380
GGG AAA GGC AAG AAG AAA GGG AAA GTG AAA GAG GAA GTG GAG GAA GAA ACT GAC CCC CGG   1140

 K   I   E   L   L   N   W   V   N   A   L   E   Q   A   M   L   D   A   L   V     400
```

```
AAG ATA GAG CTG CTG AAC TGG GTG AAT GCT TTG GAG CAA GCG ATG CTA GAT GCT TTA GTC    1200

 L   D   R   V   D   F   V   K   L   L   I   E   N   G   V   N   M   Q   H   F     420
TTA GAT CGT GTC GAC TTT GTG AAG CTC CTG ATT GAA AAC GGA GTG AAC ATG CAA CAC TTT    1260

 L   T   I   P   R   L   E   E   L   Y   N   T   R   L   G   P   P   N   T   L     440
CTG ACC ATT CCG AGG CTG GAG GAG CTT TAT AAC ACA AGA CTG GGT CCA CCA AAC ACA CTT    1320

 H   L   L   V   R   D   V   K   K   S   N   L   P   P   D   Y   H   I   S   L     460
CAT CTG CTG GTG AGG GAT GTG AAA AAG AGC AAC CTT CCG CCT GAT TAC CAC ATC AGC CTC    1380

 I   D   I   G   L   V   L   E   Y   L   M   G   G   A   Y   R   C   N   Y   T     480
ATA GAC ATC GGG CTC GTG CTG GAG TAC CTC ATG GGA GGA GCC TAC CGC TGC AAC TAC ACT    1440

 R   K   N   F   R   T   L   Y   N   N   L   F   G   P   K   R   P   K   A   L     500
CGG AAA AAC TTT CGG ACC CTT TAC AAC AAC TTG TTT GGA CCA AAG AGG CCT AAA GCT CTT    1500

 K   L   L   G   M   E   D   D   E   P   P   A   K   G   K   K   K   K   K   K     520
AAA CTT CTG GGA ATG GAA GAT GAT GAG CCT CCA GCT AAA GGG AAG AAA AAA AAA AAA AAG    1560

 K   K   E   E   E   I   D   I   D   V   D   D   P   A   V   S   R   F   Q   Y     540
AAA AAG GAG GAA GAG ATC GAC ATT GAT GTG GAC GAC CCT GCC GTG AGT CGG TTC CAG TAT    1620

 P   F   H   E   L   M   V   W   A   V   L   M   K   R   Q   K   M   A   V   F     560
CCC TTC CAC GAG CTG ATG GTG TGG GCA GTG CTG ATG AAA CGC CAG AAA ATG GCA GTG TTC    1680

 L   W   Q   R   G   E   E   S   M   A   K   A   L   V   A   C   K   L   Y   K     580
CTC TGG CAG CGA GGG GAA GAG AGC ATG GCC AAG GCC CTG GTG GCC TGC AAG CTC TAC AAG    1740

 A   M   A   H   E   S   S   E   S   D   L   V   D   D   I   S   Q   D   L   D     600
GCC ATG GCC CAC GAG TCC TCC GAG AGT GAT CTG GTG GAT GAC ATC TCC CAG GAC TTG GAT    1800

 N   N   S   K   D   F   G   Q   L   A   L   E   L   L   D   Q   S   Y   K   H     620
AAC AAT TCC AAA GAC TTC GGC CAG CTT GCT TTG GAG TTA TTA GAC CAG TCC TAT AAG CAT    1860
```

FIG. 6C

```
D   E   Q   I   A   M   K   L   L   T   Y   E   L   K   N   W   S   N   S   T     640
GAC GAG CAG ATC GCT ATG AAA CTC CTG ACC TAC GAG CTG AAA AAC TGG AGC AAC TCG ACC   1920

C   L   K   L   A   V   A   A   K   H   R   D   F   I   A   H   T   C   S   Q     660
TGC CTC AAA CTG GCC GTG GCA GCC AAA CAC CGG GAC TTC ATT GCT CAC ACC TGC AGC CAG   1980

M   L   L   T   D   M   W   M   G   R   L   R   M   R   K   N   P   G   L   K     680
ATG CTG CTG ACC GAT ATG TGG ATG GGA AGA CTG CGG ATG CGG AAG AAC CCC GGC CTG AAG   2040

V   I   M   G   I   L   L   P   P   T   I   L   F   L   E   F   R   T   Y   D     700
GTT ATC ATG GGG ATT CTT CTA CCC CCC ACC ATC TTG TTT TTG GAA TTT CGC ACA TAT GAT   2100

D   F   S   Y   Q   T   S   K   E   N   E   D   G   K   E   K   E   E   E   N     720
GAT TTC TCG TAT CAA ACA TCC AAG GAA AAC GAG GAT GGC AAA GAA AAA GAA GAG GAA AAT   2160

T   D   A   N   A   D   A   G   S   R   K   G   D   E   E   N   E   H   K   K     740
ACG GAT GCA AAT GCA GAT GCT GGC TCA AGA AAG GGG GAT GAG GAG AAC GAG CAT AAA AAA   2220

Q   R   I   I   P   I   G   T   K   I   C   K   F   Y   N   A   P   I   V   K     760
CAA AGA ATT ATC CCC ATC GGA ACA AAA ATC TGT AAA TTC TAT AAC GCG CCC ATT GTC AAG   2280

F   W   F   Y   T   I   S   Y   L   G   Y   L   L   L   F   N   Y   V   I   L     780
TTC TGG TTT TAC ACA ATA TCA TAC TTG GGC TAC CTG CTG CTG TTT AAC TAC GTC ATC CTG   2340

V   R   M   D   G   W   P   S   L   Q   E   W   I   V   I   S   Y   I   V   S     800
GTG CGG ATG GAT GGC TGG CCG TCC CTC CAG GAG TGG ATC GTC ATC TCC TAC ATC GTG AGC   2400

L   A   L   E   K   I   R   E   I   L   M   S   E   P   G   K   L   S   Q   K     820
CTG GCG TTA GAG AAG ATA CGA GAG ATC CTC ATG TCA GAA CCA GGC AAA CTC AGC CAG AAA   2460
```

FIG. 6D

```
 I   K   V   W   L   Q   E   Y   W   N   I   T   D   L   V   A   I   S   T   F     840
ATC AAA GTT TGG CTT CAG GAG TAC TGG AAC ATC ACA GAT CTC GTG GCC ATT TCC ACA TTC   2520

 M   I   G   A   I   L   R   L   Q   N   Q   P   Y   M   G   Y   G   R   V   I     860
ATG ATT GGA GCA ATT CTT CGC CTA CAG AAC CAG CCC TAC ATG GGC TAT GGC CGG GTG ATC   2580

 Y   C   V   D   I   I   F   W   Y   I   R   V   L   D   I   F   G   V   N   K     880
TAC TGT GTG GAT ATC ATC TTC TGG TAC ATC CGT GTC CTG GAC ATC TTT GGT GTC AAC AAG   2640

 Y   L   G   P   Y   V   M   M   I   G   K   M   M   I   D   M   L   Y   F   V     900
TAT CTG GGG CCA TAC GTG ATG ATG ATT GGA AAG ATG ATG ATC GAC ATG CTG TAC TTT GTG   2700

 V   I   M   L   V   V   L   M   S   F   G   V   A   R   Q   A   I   L   H   P     920
GTC ATC ATG CTG GTC GTG CTC ATG AGT TTC GGA GTA GCC CGT CAA GCC ATT CTG CAT CCA   2760

 E   E   K   P   S   W   K   L   A   R   N   I   F   Y   M   P   Y   W   M   I     940
GAG GAG AAG CCC TCT TGG AAA CTG GCC CGA AAC ATC TTC TAC ATG CCC TAC TGG ATG ATC   2820

 Y   G   E   V   F   A   D   Q   I   D   L   Y   A   M   E   I   N   P   P   C     960
TAT GGA GAG GTG TTT GCA GAC CAG ATA GAC CTC TAC GCC ATG GAA ATT AAT CCT CCT TGT   2880

 G   E   N   L   Y   D   E   E   G   K   R   L   P   P   C   I   P   G   A   W     980
GGT GAG AAC CTA TAT GAT GAG GAG GGC AAG CGG CTT CCT CCC TGT ATC CCC GGC GCC TGG   2940

 L   T   P   A   L   M   A   C   Y   L   L   V   A   N   I   L   L   V   N   L    1000
CTC ACT CCA GCA CTC ATG GCG TGC TAT CTA CTG GTC GCC AAC ATC CTG CTG GTG AAC CTG   3000

 L   I   A   V   F   N   N   T   F   F   E   V   K   S   I   S   N   Q   V   W    1020
CTG ATT GCT GTG TTC AAC AAT ACT TTC TTT GAA GTA AAA TCA ATA TCC AAC CAG GTG TGG   3060

 K   F   Q   R   Y   Q   L   I   M   T   F   H   D   R   P   V   L   P   P   P    1040
AAG TTC CAG CGA TAT CAG CTG ATT ATG ACA TTT CAT GAC AGG CCA GTC CTG CCC CCA CCG   3120
```

FIG. 6E

```
M   I   I   L   S   H   I   Y   I   I   I   M   R   L   S   G   R   C   R   K      1060
ATG ATC ATT TTA AGC CAC ATC TAC ATC ATC ATT ATG CGT CTC AGC GGC CGC TGC AGG AAA    3180

K   R   E   G   D   Q   E   E   R   D   R   G   L   K   L   F   L   S   D   E      1080
AAG AGA GAA GGG GAC CAA GAG GAA CGG GAT CGT GGA TTG AAG CTC TTC CTT AGC GAC GAG    3240

E   L   K   R   L   H   E   F   E   E   Q   C   V   Q   E   H   F   R   E   K      1100
GAG CTA AAG AGG CTG CAT GAG TTC GAG GAG CAG TGC GTG CAG GAG CAC TTC CGG GAG AAG    3300

E   D   E   Q   Q   S   S   S   D   E   R   I   R   V   T   S   E   R   V   E      1120
GAG GAT GAG CAG CAG TCG TCC AGC GAC GAG CGC ATC CGG GTC ACT TCT GAA AGA GTT GAA    3360

N   M   S   M   R   L   E   E   I   N   E   R   E   T   F   M   K   T   S   L      1140
AAT ATG TCA ATG AGG TTG GAA GAA ATC AAT GAA AGA GAA ACT TTT ATG AAA ACT TCC CTG    3420

Q   T   V   D   L   R   L   A   Q   L   E   E   L   S   N   R   M   V   N   A      1160
CAG ACT GTT GAC CTT CGA CTT GCT CAG CTA GAA GAA TTA TCT AAC AGA ATG GTG AAT GCT    3480

L   E   N   L   A   G   I   D   R   S   D   L   I   Q   A   R   S   R   A   S      1180
CTT GAA AAT CTT GCG GGA ATC GAC AGG TCT GAC CTG ATC CAG GCA CGG TCC CGG GCT TCT    3540

S   E   C   E   A   T   Y   L   L   R   Q   S   S   I   N   S   A   D   G   Y      1200
TCT GAA TGT GAG GCA ACG TAT CTT CTC CGG CAA AGC AGC ATC AAT AGC GCT GAT GGC TAC    3600

S   L   Y   R   Y   H   F   N   G   E   E   L   L   F   E   D   T   S   L   S      1220
AGC TTG TAT CGA TAT CAT TTT AAC GGA GAA GAG TTA TTA TTT GAG GAT ACA TCT CTC TCC    3660

T   S   P   G   T   G   V   R   K   K   T   C   S   F   R   I   K   E   E   K      1240
ACG TCA CCA GGG ACA GGA GTC AGG AAA AAA ACC TGT TCC TTC CGT ATA AAG GAA GAG AAG    3720
```

FIG. 6F

```
 D   V   K   T   H   L   V   P   E   C   Q   N   S   L   H   L   S   L   G   T      1260
GAC GTG AAA ACG CAC CTA GTC CCA GAA TGT CAG AAC AGT CTT CAC CTT TCA CTG GGC ACA     3780

 S   T   S   A   T   P   D   G   S   H   L   A   V   D   D   L   K   N   A   E      1280
AGC ACA TCA GCA ACC CCA GAT GGC AGT CAC CTT GCA GTA GAT GAC TTA AAG AAC GCT GAA     3840

 E   S   K   L   G   P   D   I   G   I   S   K   E   D   D   E   R   Q   T   D      1300
GAG TCA AAA TTA GGT CCA GAT ATT GGG ATT TCA AAG GAA GAT GAT GAA AGA CAG ACA GAC     3900

 S   K   K   E   E   T   I   S   P   S   L   N   K   T   D   V   I   H   G   Q      1320
TCT AAA AAA GAA GAA ACT ATT TCC CCA AGT TTA AAT AAA ACA GAT GTG ATA CAT GGA CAG     3960

 D   K   S   D   V   Q   N   T   Q   L   T   V   E   T   T   N   I   E   G   T      1340
GAC AAA TCA GAT GTT CAA AAC ACT CAG CTA ACA GTG GAA ACG ACA AAT ATA GAA GGC ACT     4020

 I   S   Y   P   L   E   E   T   K   I   T   R   Y   F   P   D   E   T   I   N      1360
ATT TCC TAT CCC CTG GAA GAA ACC AAA ATT ACA CGC TAT TTC CCC GAT GAA ACG ATC AAT     4080

 A   C   K   T   M   K   S   R   S   F   V   Y   S   R   G   R   K   L   V   G      1380
GCT TGT AAA ACA ATG AAG TCC AGA AGC TTC GTC TAT TCC CGG GGA AGA AAG CTG GTC GGT     4140

 G   V   N   Q   D   V   E   Y   S   S   I   T   D   Q   Q   L   T   T   E   W      1400
GGG GTT AAC CAG GAT GTA GAG TAC AGT TCA ATC ACG GAC CAG CAA TTG ACG ACG GAA TGG     4200

 Q   C   Q   V   Q   K   I   T   R   S   H   S   T   D   I   P   Y   I   V   S      1420
CAA TGC CAA GTT CAA AAG ATC ACG CGC TCT CAT AGC ACA GAT ATT CCT TAC ATT GTG TCG     4260

 E   A   A   V   Q   A   E   Q   K   E   Q   F   A   D   M   Q   D   E   H   H      1440
GAA GCT GCA GTG CAA GCT GAG CAA AAA GAG CAG TTT GCA GAT ATG CAA GAT GAA CAC CAT     4320
```

FIG. 6G

```
V   A   E   A   I   P   R   I   P   R   L   S   L   T   I   T   D   R   N   G      1460
GTC GCT GAA GCA ATT CCT CGA ATC CCT CGC TTG TCC CTA ACC ATT ACT GAC AGA AAT GGG    4380

M   E   N   L   L   S   V   K   P   D   Q   T   L   G   F   P   S   L   R   S      1480
ATG GAA AAC TTA CTG TCT GTG AAG CCA GAT CAA ACT TTG GGA TTC CCA TCT CTC AGG TCA    4440

K   S   L   H   G   H   P   R   N   V   K   S   I   Q   G   K   L   D   R   S      1500
AAA AGT TTA CAT GGA CAT CCT AGG AAT GTG AAA TCC ATT CAG GGA AAG TTA GAC AGA TCT    4500

G   H   A   S   S   V   S   S   L   V   I   V   S   G   M   T   A   E   E   K      1520
GGA CAT GCC AGT AGT GTA AGC AGC TTA GTA ATT GTG TCT GGA ATG ACA GCA GAA GAA AAA    4560

K   V   K   K   E   K   A   S   T   E   T   E   C   *   (SEQ ID NO: 9)             1533
AAG GTT AAG AAA GAG AAA GCT TCC ACA GAA ACT GAA TGC TAG TCTGTTTTGTTTCTTTAATTTTT    4599

TTTTTTAACAGTCAGAAACCCACTAATGGGTGTCATCTTGGCCCATCCTAAACACATMTCCAATTTCCTAAAAACATTT

TCCCT (SEQ ID NO: 8)
```

FIG. 6H

FOHY03 POLYPEPTIDES

This application is a divisional of U.S. Ser. No. 08/623,679, filed Mar. 29, 1996, now U.S. Pat. No. 5,674,739, which is a continuation-in-part of U.S. Ser. No. 08/412,431, filed Mar. 29, 1995, now U.S. Pat. No. 5,633,161.

1. INTRODUCTION

The present invention relates to methods and compositions for the diagnosis, prevention and treatment of tumor progression in mammals, for example, humans. The different types of tumors may include, but are not limited to, human melanomas, breast, gastrointestinal tumors such as esophageal, stomach, duodenal, colon, colorectal and rectal cancers, prostate, bladder, testicular, ovarian, uterine, cervical, brain, lung, bronchial, larynx, pharynx, liver, pancreatic, thyroid, bone, various types of skin cancers and neoplastic conditions such as leukemias and lymphomas. Specifically, genes which are differentially expressed in tumor cells relative to normal cells and/or relative to tumor cells at a different stage of tumor progression are identified. For example, genes are identified which are differentially expressed in benign (e.g., non-malignant) tumor cells relative to malignant tumor cells exhibiting a high metastatic potential. Genes are also identified via the ability of their gene products to interact with gene products involved in the progression to and/or aggressiveness of neoplastic tumor disease states. The genes identified can be used diagnostically or as targets for therapeutic intervention. In this regard, the present invention provides methods for the identification of compounds useful in the diagnosis, prevention and therapeutic treatment of tumor progression, including, for example, metastatic neoplastic-disorders. The present invention also provides methods for the identification of compounds useful in the diagnosis, prevention and therapeutic treatment of tumor progression, including, for example, pre-neoplastic and/or benign states. Additionally, methods are provided for the diagnostic evaluation and prognosis of conditions involving tumor progression, for the identification of subjects exhibiting a predisposition to such conditions, for monitoring patients undergoing clinical evaluation for the prevention and treatment of tumor progression disorders, and for monitoring the efficacy of compounds used in clinical trials.

2. BACKGROUND OF THE INVENTION

Cancer is the second leading cause of death in the United States, after heart disease (Boring, C.C. et al., 1993, CA Cancer J. Clin. 43:7), and develops in one in three Americans, and one of every four Americans dies of cancer. Cancer is characterized primarily by an increase in the number of abnormal, or neoplastic, cells derived from a given normal tissue which proliferate to form a tumor mass, the invasion of adjacent tissues by these neoplastic tumor cells, and the generation of malignant cells which spread via the blood or lymphatic system to regional lymph nodes and to distant sites. The latter progression to malignancy is referred to as metastasis.

Cancer can be viewed as a breakdown in the communication between tumor cells and their environment, including their normal neighboring cells. Signals, both growth-stimulatory and growth-inhibitory, are routinely exchanged between cells within a tissue. Normally, cells do not divide in the absence of stimulatory signals, and, likewise, will cease dividing in the presence of inhibitory signals. In a cancerous, or neoplastic, state, a cell acquires the ability to "override" these signals and to proliferate under conditions in which normal cells would not grow.

Tumor cells must acquire a number of distinct aberrant traits to proliferate. Reflecting this requirement is the fact that the genomes of certain well-studied tumors carry several different independently altered genes, including activated oncogenes and inactivated tumor suppressor genes. Each of these genetic changes appears to be responsible for imparting some of the traits that, in aggregate, represent the full neoplastic phenotype (Land, H. et al., 1983, Science 222:771; Ruley, H. E., 1983, Nature 3:602; Hunter, T., 1991, Cell 64:249).

In addition to unhindered cell proliferation, cells must acquire several traits for tumor progression to occur. For example, early on in tumor progression, cells must evade the host immune system. Further, as tumor mass increases, the tumor must acquire vasculature to supply nourishment and remove metabolic waste. Additionally, cells must acquire an ability to invade adjacent tissue, and, ultimately, cells often acquire the capacity to metastasize to distant sites.

The biochemical basis for immune recognition of tumor cells is unclear. It is possible that the tumorigenicity of cells can increase when the cells' display of Class I histocompatability antigens is reduced (Schrier, P. I. et al., 1983, Nature 305:771), in that these antigens, in conjunction with tumor-specific antigens are required for the tumor cells to be recognized by cytotoxic T lymphocytes (CTLs). Tumor cells which have lost one or more genes encoding tumor-specific antigens seem to escape recognition by the corresponding reactive CTLs (Van der Bruggen, P. et al., 1991, Science 254:1643).

Once a tumor reaches more than about 1 mm in diameter, it can no longer rely on passive diffusion for nutrition and removal of metabolic waste. At this point, the tumor mass must make intimate contact with the circulatory system. Thus, cells within more advanced tumors secrete angiogenic factors which promote neovascularization, i.e., the growth of blood vessels from surrounding tissue into the tumor mass (Folkman, J. and Klagsburn, M., 1987, Science 235:442; Liotta, L. A. et al., 1991, Cell 64:327). Among these angiogenic factors are the fibroblast growth factor (FGF) and endothelial cell growth factor (ECGF). Neovascularization can, in fact, be an essential precursor to metastasis. First, the process is required for a large increase in tumor cell number, which in turn, allows the appearance of rare metastatic variants. Further, neovascularization provides a direct portal entry into the circulatory system which can be used by metastasizing cells.

A variety of biochemical factors have been associated with different phases of metastases. Cell surface receptors for collagen, glycoproteins such as laminin, or proteoglycans, facilitate tumor cell attachment, an important step in invasion and metastases. Attachment then triggers the release of degradative enzymes which facilitate the penetration of tumor cells through tissue barriers. Once the tumor cell has entered the target tissue, specific growth factors are required for further proliferation.

It is apparent that the complex process of tumor progression must involve multiple gene products. It is therefore important to define the role of specific genes involved in tumor progression, to identify those gene products involved in the tumor progression process and to further identify those gene products which can serve as therapeutic targets for the diagnosis, prevention and treatment of metastases of various forms of cancers.

Some attempts have been made to study genes which are thought to elicit or augment tumor progression phenotypes.

Mutations may drive a wave of cellular multiplication associated with gradual increases in tumor size, disorganization and malignancy. For example, a mutation in the tumor suppressor gene which is a negative regulator of cellular proliferation, results in a loss of crucial control over tumor growth and progression. Differential expression of the following suppressor genes has been demonstrated in human cancers: the retinoblastoma gene, RB; the Wilms' tumor gene, WT1 (11p); the gene deleted in colon carcinoma, DCC (18q); the neurofibromatosis type 1 gene, NF1 (17q); and the gene involved in familial adenomatous polyposis coli, APC (5q) (Vogelstein, B. and Kinzler, K. W., 1993, Trends Genet. 9:138–141).

Insight into the complex events that lead from normal cellular growth to neoplasia, invasion and metastasis is crucial for the development of effective diagnostic and therapeutic strategies. The foregoing studies are aimed at defining the role of particular gene products presumed to be involved in tumor progression. However, such approaches cannot identify the full panoply of gene products that are involved in the cascade of steps in tumor progression. A great need, therefore, exists for the successful identification of those genes which are differentially expressed in cells involved in or predisposed to a tumor progression phenotype. Such differentially expressed gene and/or gene products can represent useful diagnostic markers and/or therapeutic targets for tumor progression disorders. With respect to diagnostic techniques, such genes and/or gene products could represent useful markers for the diagnosis, especially early diagnosis, given the correlation between early diagnosis and successful cancer treatment. With respect to therapeutic treatments, such differentially expressed genes and/or gene products could represent useful targets for therapeutic treatment of various forms of tumor progression disorders, including metastatic and non-metastatic neoplastic disorders, and for inhibiting the progression of pre-neoplastic lesions (e. g., hyperplastic lesions or other benign tumors) to malignant tumors.

Differentially expressed genes involved in tumor metastasis have been identified using murine melanoma cell lines of varying metastatic potentials, N-nitroso-methylurea-induced rat mammary carcinomas, mammary carcinoma cell lines, human breast tumors and spontaneous colonic and intestinal tumors in mice (Steeg, P. S., et al., 1988, J. Natl. Cancer Inst. 80:200–204; Qian, F., et al., 1994, Cell 77:335–347; Leone, A., et al., 1991, 65:25–35; Zou, Z., et al., 1994, Science 263:526–529; and Fodde, R., et al., 1994, Proc. Natl. Acad. Sci. USA 91:8969–8973).

3. SUMMARY OF THE INVENTION

The present invention relates to methods and compositions for diagnosis, prevention, and treatment of tumor progression. Specifically, murine and human genes are identified and described which are differentially expressed in tumor cells relative to normal cells and/or to tumor cells at a different stage of tumor progression. For example, genes are identified which are differentially expressed in benign (e.g., non-malignant) tumor cells relative to malignant, metastatic tumor cells. The modulation of the expression of the identified genes and/or the activity of the identified gene products can be utilized therapeutically to treat disorders involving tumor progression, including, for example, metastatic disorders. As such, methods and compositions are described for the identification of novel therapeutic compounds for the inhibition of tumor progression and the treatment of tumor progression disorders, including metastatic diseases.

Further, the identified genes and/or gene products can be used to identify cells exhibiting or predisposed to a disorder involving a tumor progression phenotype, thereby diagnosing individuals having, or at high risk for developing, such disorders. Additionally, the identified genes and/or gene products can be used to grade or stage identified tumor calls. Still further, the detection of the differential expression of identified genes can be used to devise treatments (for example, chemoprevention) before the benign cells attain a malignant state. Still further, the detection of differential expression of identified genes can be used to design a preventive intervention in pre-neoplastic cells in individuals at high risk.

"Tumor progression," as used herein, refers to any event which, first, promotes the transition of a normal, non-neoplastic cell to a cancerous, neoplastic one. Such events include ones which occur prior to the onset of neoplasia, and which predispose, or act as a step toward, the cell becoming neoplastic. These events can, for example, include ones which cause a normal cell to exhibit a pre-neoplastic phenotype. Second, such events also include ones which bring about the transition from a pre-neoplastic state to a neoplastic one. Such events can, for example, include ones which promote two hallmarks of the neoplastic state, namely unhindered cell proliferation and/or tumor cell invasion of adjacent tissue. Third, tumor progression can include events which promote the transition of a tumor cell to a metastatic state. Within each state, (e.g., pre-neoplastic, neoplastic and metastatic) the term "tumor progression" as used herein can also refer to the disorder severity or aggressiveness a cell exhibits relative to other cells within the same state.

Because multiple tumor progression events occur as a cell progresses from normal to neoplastic and metastatic states, certain cells will have undergone a different set of such tumor progression events. As such, such cells are referred to herein as belonging to different "tumor progression stages."

A "disorder involving tumor progression" or a "tumor progression disorder," as used herein, refers to the state of a cell or cells which have undergone or are in the process of undergoing a tumor progression event, as defined above.

"Differential expression," as used herein, refers to both quantitative, as well as qualitative, differences in the genes' temporal and/or cellular expression patterns among, for example, normal and neoplastic tumor cells, and/or among tumor cells which have undergone different tumor progression events. Differentially expressed genes can represent "fingerprint genes," and/or "target genes."

"Fingerprint gene," as used herein, refers to a differentially expressed gene whose expression pattern can be utilized as part of a prognostic or diagnostic marker for the evaluation of a disorder involving tumor progression, or which, alternatively, can be used in methods for identifying compounds useful for the treatment of such disorders. For example, the effect of the compound on the fingerprint gene expression normally displayed in connection with disorders involving tumor progression can be used to evaluate the efficacy of the compound as a treatment for such a disorder, or can, additionally, be used to monitor patients undergoing clinical evaluation for the treatment of the disorder.

"Fingerprint pattern," as used herein, refers to the pattern generated when the expression pattern of a series (which can range from two up to all the fingerprint genes which exist for a given state) of fingerprint genes is determined. A fingerprint pattern can be used in the same diagnostic, prognostic and compound identification methods as the expression of a single fingerprint gene.

"Target gene," as used herein, refers to a differentially expressed gene involved in tumor progression such that modulation of the level of target gene expression or of target gene product activity can act to prevent and/or ameliorate symptoms of the tumor progression. Compounds that modulate the expression of the target gene or the activity of the target gene product can be used in the treatment of neoplastic diseases, including, for example, disorders involving the progression to a metastatic state. Still further, compounds that modulate the expression of the target gene or activity of the target gene product can be used in treatments to prevent benign cells from attaining a malignant state. Still further, compounds that modulate the expression of the target gene or activity of the target gene product can be used to design a preventive intervention in pre-neoplastic cells in individuals at high risk.

Further, "pathway genes" are defined via the ability of their products to interact with other gene products involved in tumor progression disorders. Pathway genes can also exhibit target gene and/or fingerprint gene characteristics.

The present invention includes the products of such fingerprint, target, and pathway genes, as well as antibodies to such gene products. Furthermore, the engineering and use of cell-based and/or animal-based models of tumor progression disorders, including disorders involving metastasis, to which such gene products can contribute, are described.

The present invention also relates to methods for prognostic and diagnostic evaluation of tumor progression conditions, and for the identification of subjects containing cells predisposed to such conditions. Furthermore, the invention provides methods for evaluating the efficacy of therapies for disorders involving tumor progression, and for monitoring the progress of patients participating in clinical trials for the treatment of such diseases.

The tumor progression disorders described herein can include disorders involved in the progression of such human cancers as, for example, human melanomas, breast, gastrointestinal, such as esophageal, stomach, colon, bowel, colorectal and rectal cancers, prostate, bladder, testicular, ovarian, uterine, cervical, brain, lung, bronchial, larynx, pharynx, liver, pancreatic, thyroid, bone, leukemias, lymphomas, and various types of skin cancers.

The invention also provides methods for the identification of compounds that modulate the expression of genes or the activity of gene products involved in tumor progression, including the progression of metastatic neoplastic diseases, as well as methods for the treatment of such diseases. Such methods can, for example, involve the administration of such compounds to individuals exhibiting symptoms or markers of tumor progression, such as markers for metastatic neoplastic diseases.

This invention is based, in part on systematic search strategies involving in vivo and in vitro paradigms of tumor progression, including the progression to metastatic disease, coupled with sensitive and high throughput gene expression assays, to identify genes differentially expressed in tumor cells relative to normal cells and/or relative to tumor cells at a different tumor progression stage. In contrast to approaches that merely evaluate the expression of a given gene product presumed to play a role in one or another of the various stages of tumor progression, such as, for example the progression to a metastatic disease process, the search strategies and assays used herein permit the identification of all genes, whether known or novel, which are differentially expressed in tumor cells relative to normal cells or relative to tumor cells at a different stage of tumor progression.

This comprehensive approach and evaluation permits the discovery of novel genes and gene products, as well as the identification of an array of genes and gene products (whether novel or known) involved in novel pathways that play a major role in the disease pathology. Thus, the present invention makes possible the identification and characterization of targets useful for prognosis, diagnosis, monitoring, rational drug design, and/or other therapeutic intervention of tumor progression disorders, including disorders involving metastasis.

The Example presented in Section 6, below, demonstrates the successful use of tumor progression search strategies of the invention to identify genes which are differentially expressed within tumor cells relative to tumor cells at a different stage of tumor progression. Specifically, the Example identifies a gene which is differentially expressed in metastatic cell populations relative to benign, non-malignant tumor cells.

This gene, referred to herein as the 030 gene (fomy030 in the mouse and fohy030 in humans), is a novel gene which is expressed at a many-fold higher level in non-metastatic tumor cells relative to its expression in metastatic tumor cells. The gene appears in mice and has the cDNA sequence shown in FIG. 3A and 3B (SEQ ID NO:2). A homologous gene, referred to herein as the fohy030 gene, appears in humans and has the cDNA sequence shown in FIG. 5 (SEQ ID NO:6). An alternative splice form of the human cDNA has the sequence shown in FIG. 6 (SEQ ID NO:8). Unless stated expressly otherwise, any general reference to the 030 gene hereinafter refers to both the murine (fomy030) and human (fohy030) homologs of this gene.

The identification of the 030 gene and the characterization of its expression in particular stages of metastatic spread provides, therefore, newly identified targets for the diagnosis, prevention, and treatment of tumor progression disorders, including metastatic neoplastic diseases.

Its expression pattern indicates that the 030 gene product acts to inhibit tumor progression. For example, a reduction in the level of 030 gene expression correlates with an increase in a cell's metastatic potential i.e., a reduction of 030 gene product in tumor cells can induce or predispose a cell to progress to a metastatic state.

Hence, any method which can bring about an increase in the amount of 030 gene product can inhibit or slow the progression to metastasis. In fact, it is possible that the 030 gene product exhibits general tumor inhibition properties.

A cDNA clone of the murine homolog, designated fomy030, is described herein in FIGS. 3A and 3B (SEQ ID NO:2) (nucleotide sequence and amino acid sequence), and was derived from fomy030 mRNA. However, as used herein, fomy030 cDNA refers to any DNA sequence that encodes the amino acid sequence depicted in FIGS. 3A and 3B (SEQ ID NO:3).

A cDNA clone of the human homolog, designated fohy030, is shown in FIG. 5 (SEQ ID NO:6) (nucleotide sequence and amino acid sequence). An alternative splice form of fohy030 is shown in FIG. 6 (SEQ ID NO:8). Both were obtained using the entire mouse fohy030 cDNA as a probe. However, as used herein, fohy030 cDNA refers to any DNA sequence that encodes the amino acid sequences depicted in FIG. 5 (SEQ ID NO:7) and FIG. 6 (SEQ ID NO:9).

3.1. DEFINITIONS

"Tumor progression," as used herein, refers to any event which, first, promotes the transition of a normal, non-neoplastic cell to a cancerous, neoplastic one. Such events include ones which occur prior to the onset of neoplasia, and which predispose, or act as a step toward, the cell becoming neoplastic. These events can, for example, include ones which cause a normal cell to exhibit a pre-neoplastic phenotype. Second, such events also include ones which bring about the transition from a pre-neoplastic state to a neoplastic one. Such events can, for example, include ones which promote unhindered cell proliferation and/or tumor cell invasion of adjacent tissue, which are viewed as hallmarks of the neoplastic state. Third, tumor progression can include events which promote the transition of a tumor cell to a metastatic state. Within each state, (e.g., pre-neoplastic, neoplastic and metastatic) the term "tumor progression" as used herein can also refer to the disorder severity or aggressiveness a cell exhibits.

Because multiple tumor progression events occur as a cell progresses from a normal to neoplastic and metastatic states, certain cells will have undergone a different set of such tumor progression events. As such, such cells are referred to herein as belonging to different "tumor progression stages."

A "disorder involving tumor progression" or a "tumor progression disorder," as used herein, refers to the state of a cell or cells which have undergone or are in the process of undergoing a tumor progression event, as defined above.

"Differential expression," as used herein, refers to both quantitative, as well as qualitative differences in the genes' temporal and/or cellular expression patterns among, for example, normal and neoplastic tumor cells, and/or among tumor cells which have undergone different tumor progression events. Differentially expressed genes can represent "fingerprint genes," and/or "target genes."

"Fingerprint gene," as used herein, refers to a differentially expressed gene whose expression pattern can be utilized as part of a prognostic or diagnostic marker for the evaluation of tumor progression, or which, alternatively, can be used in methods for identifying compounds useful for the treatment of tumor progression. For example, the effect of the compound on the fingerprint gene expression normally displayed in connection with tumor progression can be used to evaluate the efficacy of the compound as a treatment for tumor progression, or can, additionally, be used to monitor patients undergoing clinical evaluation for the treatment of tumor progression.

"Fingerprint pattern," as used herein, refers to the pattern generated when the expression pattern of a series (which can range from two up to all the fingerprint genes which exist for a given state) of fingerprint genes is determined. A fingerprint pattern can be used in the same diagnostic, prognostic and compound identification methods as the expression of a single fingerprint gene.

"Target gene," as used her in, refers to a differentially expressed gene involved in tumor progression such that modulation of the level of target gene expression or of target gene product activity can act to prevent and/or ameliorate symptoms of the tumor progression. Compounds that modulate target gene expression or activity of the target gene product can be used in the treatment of tumor progression and tumor progression disorders, including, for example, disorders involving the progression to a metastatic state.

Further, "pathway genes" are defined via the ability of their products to interact with other gene products involved in tumor progression. Pathway genes can also exhibit target gene and/or fingerprint gene characteristics.

4. DESCRIPTION OF THE FIGURES

FIG. 1 is a Northern blot confirming differential regulation of the 030 gene. Total RNA (12 μg/lane) obtained from F1 (lanes 1 and 3) and F10 (lanes 2 and 4) melanoma cell cultures was hybridized with a cDNA probe prepared by random priming of reamplified romy030 band. (See materials and methods below in Section 6.1.). The romy030 probe identifies an RNA band of approximately 3 kb, corresponding to a fomy030 mRNA.

FIG. 2 is a nucleotide sequence of romy030 band (SEQ ID NO:1).

FIGS. 3A–3C are representations of the nucleotide and derived amino acid sequences of cDNA clone fomy030 (SEQ ID NOs:2 [nucleotide sequence] and 3 [amino acid sequence]) derived from fomy030 mRNA.

FIGS. 5A–5G is a representation of the nucletide and deduced amino acid sequences of cDNA clone of fohy030 (SEQ ID NOs:6 [nucleotide sequence] and 7 [amino acid sequence]).

FIGS 6A–6H is a comparison of the nucletide and deduced amino acid sequences of another cDNA clone of fohy030 (SEQ ID NOs:8 [nucleotide sequence] and 9 [amino acid sequence]).

Figure 1:
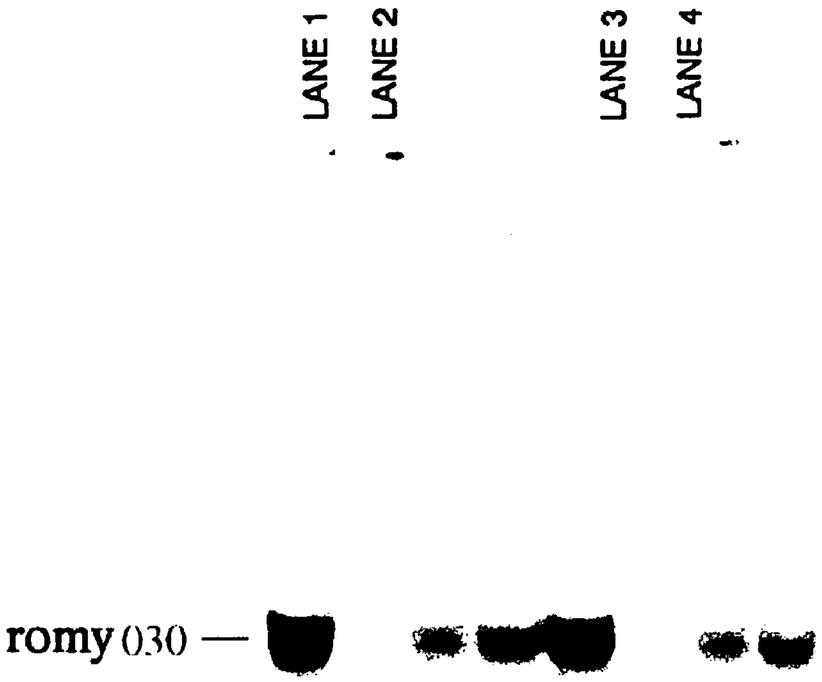

In FIGS. 3A–3C, the nucleotide sequence is numbered starting at the first nucleotide, whereas in FIGS. 5A–5G and 6A–6H, the nucleotide sequence is numbered starting at the ATG start codon.

5. DETAILED DESCRIPTION OF THE INVENTION

Methods and compositions for the prevention, treatment and diagnosis of tumor progression, including tumor progression involving metastatic disorders, in cells involved in human tumors. Such human tumors may include, for example, human melanomas, breast, gastrointestinal tumors such as esophageal, stomach, duodenal, colon, colorectal and rectal cancers, prostate, bladder, testicular, ovarian, uterine, cervical, brain, lung, bronchial, larynx, pharynx, liver, pancreatic, thyroid, bone, various types of skin cancers and other neoplastic conditions such as leukemias, lymphomas. The invention is based, in part, on the evaluation and expression and role of all genes that are differentially expressed in tumor cells relative to normal cells and/or relative to tumor cells at a different stage of tumor progression. This permits the definition of disease pathways and identification of targets in such pathways that are useful for diagnosis, prevention and treatment of tumor progression, including the tumor progression disorders involving metastatic neoplastic diseases.

Genes, termed "target genes" and/or "fingerprint genes" are described which are differentially expressed in tumor cells relative to their expression in normal cells or relative to their expression in tumor cells which are at a different stage of tumor progression. Additionally, genes, termed "pathway genes" are described whose gene products exhibit an ability to interact with gene products involved tumor progression, including tumor progression disorders involving metastatic neoplastic disorders. Pathway genes can additionally have fingerprint and/or target gene characteristics. Methods for the identification of such fingerprint, target, and pathway genes are also described.

Further, the gene products of such fingerprint, target, and pathway genes are described in Section 5.2.2, antibodies to such gene products are described in Section 5.2.3, as are cell- and animal-based models of tumor progression disorders to which such gene products can contribute, in Section 5.2.4.

Methods for the identification of compounds which modulate the expression of genes or the activity of gene products involved in tumor progression are described in Section 5.3. Methods for monitoring the efficacy of compounds during clinical trials are described in Section 5.3.5. Additionally described, below, are methods for treatment of tumor progression disorders, including metastatic diseases.

Also discussed, below, are methods for prognostic and diagnostic evaluation of tumor progression and disorders involving tumor progression, including metastatic disorders, and, further, for the identification of subjects exhibiting a predisposition to such disorders.

5.1. IDENTIFICATION OF DIFFERENTIALLY EXPRESSED GENES

Described herein are methods for the identification of differentially expressed genes which are involved in tumor progression. There exist a number of levels or stages at which the differential expression of such genes can be exhibited. For example, differential expression can occur in tumor cells relative to normal cells, or in tumor cells within different stages of tumor progression. For example, genes can be identified which are differentially expressed in pre-neoplastic versus neoplastic cells. Such genes can include, for example, ones which promote unhindered cell proliferation or tumor cell invasion of adjacent tissue, both of which are viewed as hallmarks of the neoplastic state. Further, differential expression can occur in benign (e.g., non-malignant) tumor cells versus metastatic, malignant tumor cells. Still further, differential expression can occur among cells within any one of these states (e.g., pre-neoplastic, neoplastic and metastatic), and can indicate, for example, a difference in tumor progression severity or aggressiveness of one cell relative to that of another cell within the same state.

Methods for the identification of such differentially expressed genes are described, below, in Section 5.1.1. Methods for the further characterization of such differentially expressed genes, and for their categorization as target and/or fingerprint genes, are presented, below, in Section 5.3.

"Differential expression" as used herein refers to both quantitative, as well as qualitative differences in the genes' temporal and/or tissue expression patterns. Thus, a differentially expressed gene can qualitatively have its expression activated or completely inactivated in, for example, normal versus tumor progression states, in cells within different tumor progression states or among cells within a single given tumor progression state. Such a qualitatively regulated gene will exhibit an expression pattern within a given state which is detectable by standard techniques in one such state, but is not detectable in both states being compared. "Detectable," as used herein, refers to an RNA expression level which is detectable via the standard techniques of differential display, RT (reverse transcriptase)-coupled PCR, Northern and/or RNase protection analyses.

Alternatively, a differentially expressed gene can exhibit an expression level which differs, i.e., is quantitatively increased or decreased in normal versus tumor progression states, in cells within different tumor progression states or among cells within a single given tumor progression state.

The degree to which expression differs need only be large enough to be visualized via standard characterization techniques, such as, for example, the differential display technique described below. Other standard, well-known characterization techniques by which expression differences can be visualized include, but are not limited to, quantitative RT (reverse transcriptase)-coupled PCR and Northern analyses and RNase protection techniques.

Differentially expressed genes can be further described as target genes and/or fingerprint genes. "Fingerprint gene," as used herein, refers to a differentially expressed gene whose expression pattern can be utilized as part of a prognostic or diagnostic marker in tumor progression evaluation, or which, alternatively, may be used in methods for identifying compounds useful for the prevention or treatment of tumor progression and tumor progression disorders, including metastatic disorders. A fingerprint gene can also have the characteristics of a target gene or a pathway gene (see below, in Section 5.2).

"Fingerprint pattern," as used herein, refers to the pattern generated when the expression pattern of a series (which can range from two up to all the fingerprint genes which exist for a given state) of fingerprint genes is determined. A fingerprint pattern can be used in the same diagnostic, prognostic and compound identification methods as the expression of a single fingerprint gene.

"Target gene," as used herein, refers to a differentially expressed gene involved in tumor progression in a manner by which modulation of the level of target gene expression or of target gene product activity can act to prevent and/or ameliorate symptoms of disorders involving tumor progression. Tumor progression disorders include, for example, disorders involved in human tumors, including, but not limited to human melanomas, breast, gastrointestinal, a such as esophageal, stomach, colon, bowel, colorectal and rectal cancers, prostate, bladder, testicular, ovarian, uterine, cervical, brain, lung, bronchial, larynx, pharynx, liver, pancreatic, thyroid, bone, leukemias, lymphomas and various types of skin cancers. A target gene can also have the characteristics of a fingerprint gene and/or a pathway gene (as described, below, in Section 5.2).

5.1.1 METHODS FOR THE IDENTIFICATION OF DIFFERENTIALLY EXPRESSED GENES

A variety of methods can be utilized for the identification of genes which are involved in tumor progression. Described in Section 5.1.1.1 are experimental paradigms which can be utilized for the generation of samples which can be used for the identification of such genes. Material generated in paradigm categories can be characterized for the presence of differentially expressed gene sequences as discussed, below, in Section 5.1.1.2.

5.1.1.1 PARADIGMS FOR THE IDENTIFICATION OF DIFFERENTIALLY EXPRESSED GENES

Paradigms which represent models of tumor progression states are described herein. These paradigms can be utilized for the identification of genes which are differentially expressed in normal cells versus cells in tumor progression states, in cells within different tumor progression states or among cells within a single given tumor progression state.

The paradigms described herein include at least two groups of cells of a given cell type, preferably genetically matched cells (e.g., cells derived from variants of the same cell line, or cells derived from a single individual or biological sample), whose expression patterns are compared and analyzed for differential expression. Methods for the analysis of paradigm material are described, below, in Section 5.1.1.2.

Once a particular gene has been identified through the use of one paradigm, its expression pattern can be further characterized, for example, by studying its expression in a different paradigm. A gene can, for example, be regulated one way, i.e., can exhibit one differential gene expression pattern, in a given paradigm, but can be regulated differently in another paradigm. The use, therefore, of multiple paradigms can be helpful in distinguishing the roles and relative importance of particular genes in tumor progression.

In one embodiment of such a paradigm, referred to herein as the "in vitro" paradigm, cell lines can be used to identify genes which are differentially expressed in tumor progression states. Differentially expressed genes are detected, as described herein, by comparing the pattern of gene expression between the experimental and control conditions. In such a paradigm, genetically matched tumor cell lines (e.g., variants of the same cell line) are generally utilized. For example, the gene expression pattern of two variant cell lines can compared, wherein one variant exhibits characteristics of one tumor progression state while the other variant exhibits characteristics of another tumor progression state. Alternatively, two variant cell lines, both of which exhibit characteristics of the same tumor progression state, but which exhibit differing degrees of tumor progression disorder severity or aggressiveness. Further, genetically matched cell lines can be utilized, one of which exhibits characteristics of a tumor progression state, while the other exhibits a normal cellular phenotype.

The variant cell lines utilized herein can exhibit such tumor progression characteristics as, for example, a high or low metastatic potential, which refers to the likelihood that a cell will give rise to a distant site tumor mass. Alternatively, one or more such variant cell lines can exhibit pre-neoplastic characteristics or can exhibit characteristics generally associated with one or more neoplastic cell phenotypes, such as, for example, cell proliferation or invasion phenotypes.

In accordance with this aspect of the invention, the cell line variants are cultured under appropriate conditions, the cells are harvested, and RNA is isolated and analyzed for differentially expressed genes, as described in detail in Section 5.1.1.2, below.

Examples of cell lines that can be used as part of such in vitro paradigms include but are not limited to variants of melanoma cell lines, such as, for example, the murine melanoma B16 F1 cell line which exhibits a low metastatic potential and the melanoma B16 F10 cell line which exhibits a high metastatic potential (Fidler, I. J., 1973, Nature New Biol 242:148–149); human colon cell lines, such as, for example KM12c (tumor cell line with low metastatic potential) and the KM20L4 (tumor cell line with high metastatic potential; Morikawa K., et al., 1988, Cancer Research 48:1943–1948); prostatic tumor cell lines, such as, for example, DU 145 (non metastatic tumor cell line) and PC-3-M (high metastatic potential tumor cell line; Karmali, R. A. et al., 1987, Anticancer Res. 7:1173–1180, and Koziowski, J. M. et al., 1984, Cancer Research 44:3522–3529); and breast carcinoma tumor cell lines, such as, for example, MCF-7 (non metastatic tumor cell line) and MDA-MB-435 (high metastatic potential tumor cell line; Watts C. K. et al., 1994, Breast Cancer Res. Treat. 31:95–105 and Rose, D. P. et al., 1993, J. Natl. Cancer Inst. 85:1743–1747).

As presented in the Example presented in Section 6, below, this paradigm has been successfully utilized to identify a gene, referred to herein as the 030 gene, which is differentially expressed in cells exhibiting a high metastatic potential relative to cells exhibiting a low metastatic potential. Specifically, the 030 gene is expressed at a many-fold higher level in low metastatic potential cells relative to cells exhibiting a high metastatic potential.

In a second paradigm, referred to herein as the in vivo paradigm, animal models of tumor progression disorders can be utilized to discover differentially expressed gene sequences. The in vivo nature of such tumor progression models can prove to be especially predictive of the analogous responses in living patients.

A variety of tumor progression animal models can be used for as part of the in vivo paradigms. For example, animal models of tumor progression may be generated by passaging tumor cells in animals (e.g., mice), leading to the appearance of tumors within these animals.

Additional animal models, some of which may exhibit differing tumor progression characteristics, may be generated from the original animal models described above. For example, the tumors which result in the original animals can be removed and grown in vitro. Cells from these in vitro cultures can then be passaged in animals and tumors resulting from this passage can then be isolated. RNA from pre-passage cells, and cells isolated after one or more rounds of passage can then be isolated and analyzed for differential expression. The differential expression can be compared to the metastatic potential expression of such cells. These cells can now represent cells from different tumor progression states, or cells within a given tumor progression state exhibiting differing degrees of severity or aggressiveness. Such passaging techniques can utilizing any of the variant cell lines described, above, for the in vitro paradigms.

Additionally, animal models for tumor progression which can be utilized for such an in vivo paradigm include any of the animal models described, below, in Section 5.7.1. Other models include transgenic mouse model for melanoma (Mintz, B. and Silvers, W. K., 1993, Proc. Natl. Acad. Sci. USA 90:8817–8812), transgenic mice which carry specific adenomatous polyposis coli (APC) gene mutations (Fodde, R., et al., 1994, Proc. Natl. Acad. Sci. USA 91:8969–8973) and the transgenic mouse in which the mammary tumor virus LTR/c-myc gene is anomalously expressed (Leder, A., et al., 1986, Cells 45:485–495).

A third paradigm, referred to herein as the "specimen paradigm," utilizes samples from surgical and biopsy specimens. Such specimens can represent normal tissue, primary, secondary or metastasized tumors obtained from patients having undergone surgical treatment for disorders involving tumor progression such as, for example, melanomas, colon carcinomas, lung carcinomas, prostatic cancers and breast cancers.

Surgical specimens can be procured under standard conditions involving freezing and storing in liquid nitrogen (see, for example, Karmali, R. A., et al., 1983, Br. J. cancer 48:689–696.) RNA from specimen cells is isolated by, for example, differential centrifugation of homogenized tissue, and analyzed for differential expression relative to other specimen cells, preferably cells obtained from the same patient.

In paradigms designed to identify genes which are involved in tumor progression, compounds known to have an ameliorative effect on the tumor progression symptoms can also be used in paradigms to detect differentially expressed genes. Such compounds can include known therapeutics, as well as compounds that are not useful as therapeutics due to their harmful side effects. For example, tumor cells that are cultured as explained in this Section, above, can be exposed to one of these compounds and analyzed for differential gene expression with respect to untreated tumor cells, according to the methods described below in Section 5.1.1.2. In principle, however, according to the paradigm, any cell type involved in tumor progression and disorders thereof can be treated by these compounds at any stage of the tumor progression process.

Cells involved in tumor progression can also be compared to unrelated cells (e.g., fibroblasts) which have been treat d with the compound, such that any generic effects on gene expression that might not be related to the disease or its treatment may be identified. Such generic effects might be manifest, for example, by changes in gene expression that are common to the test cells and the unrelated cells upon treatment with the compound.

By these methods, the genes and gene products upon which these compounds act can be identified and used in the assays described below to identify novel therapeutic compounds for inhibition of tumor progression and the treatment of tumor progression disorders, including metastatic diseases.

5.1.1.2. ANALYSIS OF PARADIGM MATERIAL

In order to identify differentially expressed genes, RNA, either total or mRNA, can be isolated from cells utilized in paradigms such as those described earlier in Section 5.1.1.1. Any RNA isolation technique which does not select against the isolation of mRNA can be utilized for the purification of such RNA samples. See, for example, Ausubel, F. M. et al., eds., 1987–1993, *Current Protocols in Molecular Biology,* John Wiley & Sons, Inc. New York, which is incorporated herein by reference in its entirety. Additionally, large numbers of tissue samples can readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes can be identified by utilizing a variety of methods which are well known to those of skill in the art. For example, differential screening (Tedder, T. F. et al., 1988, Proc. Natl. Acad. Sci. USA 85:208–212), subtractive hybridization (Hedrick, S. M. et al., 1984, Nature 308:149–153; Lee, S. W. et al., 1984, Proc. Natl. Acad. Sci. USA 88:2825), and, preferably, differential display (Liang, P. and Pardee, A. B., 1993, U.S. Pat. No. 5,262,311, which is incorporated herein by reference in its entirety), can be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe can correspond to a total cell cDNA probe of a call type or tissue derived from a control subject, while the second cDNA probe can correspond to a total cell cDNA probe of the same cell type derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, e.g, control and experimental tissue, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique describes a procedure, utilizing the well-known polymerase chain reaction (PCR; the experimental embodiment set forth in Mullis, K. B., 1987, U.S. Pat. No. 4,683,202) which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction can include, but are not limited to, oligo dT-containing primers, preferably of the 3' primer type of oligonucleotide described below. Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts can be identified those which have been produced from differentially expressed genes.

The 3' oligonucleotide primer of the primer pairs can contain an oligo dT stretch of 10–13 dT nucleotides at its 5' end, preferably 11, which hybridizes to the poly(A) tail of mRNA or to the complement of a cDNA reverse transcribed from an mRNA poly(A) tail. Second, in order to increase the specificity of the 3' primer, the primer can contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The 5' primer can contain a nucleotide sequence expected, statistically, to have the ability to hybridize to cDNA sequences derived from the tissues of interest. The nucleotide sequence can be an arbitrary one, and the length of the 5' oligonucleotide primer can range from about 9 to about 15 nucleotides, with about 13 nucleotides being preferred.

Additionally, arbitrary primer sequences cause the lengths of the amplified partial cDNAs produced to be variable, thus allowing different clones to be separated by using standard denaturing sequencing gel electrophoresis.

PCR reaction conditions should be chosen which optimize amplified product yield and specificity, and, additionally, produce amplified products of lengths which can be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified via bulk techniques such as, for example, those described above, the differential expression of such putatively differentially expressed genes should be corroborated. Corroboration can be accomplished via, for example, such well-known techniques as Northern analysis, quantitative RT-coupled PCR or RNase protection.

Upon corroboration, the differentially expressed genes can be further characterized, and can be identified as target and/or fingerprint genes, as discussed, below, in Section 5.1.4.

Also, amplified sequences of differentially expressed genes obtained through differential display can be used to isolate the full length clones of the corresponding gene. The full-length coding portion of the gene can readily be isolated, without undue experimentation, by molecular biological techniques well known in the art. For example, the isolated differentially expressed amplified fragment can be labeled and used to screen a cDNA library. Alternatively, the labeled fragment can be used to screen a genomic library.

PCR technology can also be utilized to isolate full-length cDNA sequences. As described in this section above, the isolated amplified gene fragments (of about at least 10 nucleotides, preferrably longer, of about 15 nucleotides) obtained through differential display have their 5' terminal end at some random point within the gene and have 3' terminal ends at a position corresponding to the 3' end of the transcribed portion of the gene. Once nucleotide sequence information from an amplified fragment is obtained, the remainder of the gene (i.e., the 5' end of the gene, when utilizing differential display) can be obtained using, for example, RT PCR.

In one embodiment of such a procedure for the identification and cloning of full length gene sequences, RNA can be isolated, following standard procedures, from an appropriate tissue or cellular source.

A reverse transcription reaction can then be performed on the RNA using an oligonucleotide primer complementary to the mRNA that corresponds to the amplified cloned fragment, for the priming of first strand synthesis. Because the primer is anti-parallel to the mRNA, extension will proceed toward the 5' end of the mRNA. The resulting RNA/DNA hybrid can then be "tailed" with guanines using a standard terminal transferase reaction, the hybrid can be digested with RNAase H, and second strand synthesis can then be primed with a poly-C primer. Using the two primers, the 5' portion of the gene is then amplified using PCR. Sequences obtained can then be isolated and recombined with previously isolated sequences to generate a full-length cDNA of the differentially expressed genes of the invention. For a review of cloning strategies and recombinant DNA techniques which can be used, see, e.g., Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

5.2. METHODS FOR THE IDENTIFICATION OF PATHWAY GENES

Methods are described herein for the identification of pathway genes. "Pathway gene," as used herein, refers to a gene whose gene product exhibits the ability to interact with gene products involved in tumor progression. A pathway gene can be differentially expressed and, therefore, can have the characteristics of a target and/or fingerprint gene.

Any method suitable for detecting protein-protein interactions can be employed for identifying pathway gene products by identifying interactions between gene products and gene products known to be involved in tumor progression and tumor progression disorders, including metastatic disorders. Such known gene products can be cellular or extracellular proteins. Those gene products which interact with such known gene products represent pathway gene products and the genes which encode them represent pathway genes.

Among the traditional methods which can be employed are co-immunoprocipitation, cross-linking and co-purification through gradients or chromatographic columns. Utilizing procedures such as these allows for the identification of pathway gene products. Once identified, a pathway gene product can be used, in conjunction with standard techniques, to identify its corresponding pathway gene. For example, at least a portion of the amino acid sequence of the pathway gene product can be ascertained using techniques well known to those of skill in the art, such as via the Edman degradation technique (see, e.g., Creighton, 1983, Proteins: Structures and Molecular Principles, W. H. Freeman & Co., N.Y., pp.34–49). The amino acid sequence obtained can be used as a guide for the generation of oligonucleotide mixtures that can be used to screen for pathway gene sequences. Screening can be accomplished, for example by standard hybridization or PCR techniques. Techniques for the generation of oligonucleotide mixtures and the screening are well known. (See, e.g., Ausubel, supra., and PCR Protocols: A Guide to Methods and Applications, 1990, Innis, M. et al., eds. Academic Press, Inc., New York).

Additionally, methods can be employed which result in the simultaneous identification of pathway genes which encode the protein interacting with a protein involved in tumor progression and tumor progression disorders, including metastatic diseases. These methods include, for example, probing expression libraries with labeled protein known or suggested to be involved in metastatic diseases using this protein in a manner similar to the well known technique of antibody probing of λgt11 libraries.

One method which detects protein interactions in vivo, the yeast two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins; the first hybrid protein consists of the DNA-binding domain of a transcription factor (e.g., activation protein) fused to a known protein, in this case, a protein known to be involved in tumor progression, and the second hybrid protein consists of the transcription factor's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose expression is regulated by the transcription factor's binding site. Either hybrid protein alone cannot activate transcription of the reporter gene. The DNA binding hybrid protein cannot activate transcription because it does not provide the activation domain function and the activation domain hybrid protein cannot activate transcription because it lacks the domain required for binding to its target site (e.g., it cannot localize to the transcription activator protein's binding site). Interaction between the DNA binding hybrid protein and the library encoded protein reconstitutes the functional transcription factor and results in expression of the reporter gene, which is detected by an assay for the reporter gene product.

The two-hybrid system or related methodology can be used to screen activation domain libraries for proteins that interact with a known "bait" gene product. By way of example, and not by way of limitation, gene products (e.g., 030 gene products) known to be involved in tumor progression and tumor progression disorders, such as metastatic diseases, can be used as the bait gene products. Total genomic or cDNA sequences are fused to the DNA encoding an activation domain. This library and a plasmid encoding a hybrid of the bait gene product fused to the DNA-binding domain are cotransformed into a yeast reporter strain, and the resulting transformants are screened for those that express the reporter gene. For example, and not by way of limitation, the bait gene can be cloned into a vector such that it is translationally fused to the DNA encoding the DNA-binding domain of the GAL4 protein. The colonies are purified and the (library) plasmids responsible for reporter gene expression are isolated. The inserts in the plasmids are sequenced to identify the proteins encoded by the cDNA or genomic DNA.

A cDNA library of a cell or tissue source which expresses proteins predicted to interact with the bait gene product can be made using methods routinely practiced in the art. According to the particular system described herein, the library is generated by inserting the cDNA fragments into a vector such that they are translationally fused to the activation domain of GAL4. This library can be co-transformed along with the bait gene-GAL4 fusion plasmid into a yeast strain which contains a lacZ gene whose expression is controlled by a promoter which contains a GAL4 activation sequence. A cDNA encoded protein, fused to GAL4 activation domain, that interacts with the bait gene product will reconstitute an active GAL4 transcription factor and thereby drive expression of the lacZ gene. Colonies which express lacZ can be detected by their blue color in the presence of X-gal. cDNA containing plasmids from such a blue colony can then be purified and used to produce and isolate the bait gene product interacting protein using techniques routinely practiced in the art.

Once a pathway gene has been identified and isolated, it can be further characterized as, for example, discussed below, in Section 5.3.

5.3. CHARACTERIZATION OF DIFFERENTIALLY EXPRESSED AND PATHWAY GENES

Differentially expressed genes, such as those identified via the methods discussed, above, in Section 5.1, and pathway genes, such as those identified via the methods discussed, above, in Section 5.2, above, as well as genes identified by alternative means, can be further characterized by utilizing, for example, methods such as those discussed herein. Such genes will be referred to herein as "identified genes."

Analyses such as those described herein, yield information regarding the biological function of the identified genes. An assessment or the biological function of the differentially expressed genes, in addition, will allow for their designation as target and/or fingerprint genes. Specifically, any of the differentially expressed genes whose further characterization indicates that a modulation of the gene's expression or a modulation of the gene product's activity can inhibit tumor progression will be designated "target genes," as defined, above, in Section 5.1. Such target genes and target gene products, along with those discussed below, will constitute the focus of the compound discovery strategies discussed, below, in Section 5.8. Further, such target genes, target gene products and/or modulating compounds can be used as part of the tumor progression disorder treatment methods described, below, in Section 5.9.

Any of the differentially expressed genes whose further characterization indicates that such modulations does not positively affect tumor progression, but whose expression pattern contributes to a gene expression "fingerprint" pattern correlative of, for example, tumor progression will be designated a "fingerprint gene." "Fingerprint patterns" will be more fully discussed, below, in Section 5.11.1. It should be noted that each of the target genes can also function as fingerprint genes, as can all or a portion of the pathway genes.

It should further be noted that the pathway genes can also be characterized according to techniques such as those described herein. Those pathway genes which yield information indicating that they are differentially expressed and that modulation of the gene's expression or a modulation of the gene product's activity can inhibit tumor progression or ameliorate tumor progression-associated symptoms will also be designated "target genes." Such target genes and target gene products, along with those discussed above, will constitute the focus of the compound discovery strategies discussed, below, in Section 5.8 and can be used as part of the treatment methods described in Section 5.9, below.

It should be additionally noted that the characterization of one or more of the pathway genes can reveal a lack of differential expression, but evidence that modulation of the gene's activity or expression can, nonetheless, ameliorate symptoms of tumor progression. In such cases, these genes and gene products would also be considered a focus of the compound discovery strategies of Section 5.8, below and can be used as part of the treatment methods described in Section 5.9, below.

In instances wherein a pathway gene's characterization indicates that modulation of gene expression or gene product activity cannot retard the tumor progression diseases of interest, but is differentially expressed and contributes to a gene expression fingerprint pattern correlative of, tumor progression states or disorders, such as metastatic diseases, such pathway genes can additionally be designated as fingerprint genes.

A variety of techniques can be utilized to further characterize the identified genes. First, the nucleotide sequence of the identified genes, which can be obtained by utilizing standard techniques well known to those of skill in the art, can be used to further characterize such genes. For example, the sequence of the identified genes can reveal homologies to one or more known sequence motifs which can yield information regarding the biological function of the identified gene product.

Second, an analysis of the tissue and/or cell type distribution of the mRNA produced by the identified genes can be conducted, utilizing standard techniques well known to those of skill in the art. Such techniques can include, for example, Northern analyses, RT-coupled PCR and RNass protection techniques. Such analyses provide information as to whether the identified genes are expressed in tissues expected to contribute to tumor progression. Such analyses can also provide quantitative information regarding steady state mRNA regulation, yielding data concerning which of the identified genes exhibits a high level of regulation in, preferably, tissues which can be expected to contribute to tumor progression. Additionally, standard in situ hybridization techniques can be utilized to provide information regarding which cells within a given tissue express the identified gene. Such an analysis can provide information regarding the biological function of an identified gene relative to given tumor progression in instances wherein only a subset of the cells within the tissue is thought to be relevant to the disorder.

Third, the sequences of the identified genes can be used, utilizing standard techniques, to place the genes onto genetic maps, e.g., mouse (Copeland, N. G. and Jenkins, N. A., 1991, Trends in Genetics 7:113–118) and human genetic maps (Cohen, D., et al., 1993, Nature 366:698–701). Such mapping information can yield information regarding the genes' importance to human disease by, for example, identifying genes which map within genetic regions to which known genetic tumor progression disorders map.

Fourth, the biological function of the identified genes can be more directly assessed by utilizing relevant in vivo and in vitro systems. In vivo systems can include, but are not limited to, animal systems which naturally exhibit symptoms of tumor progression, such as metastatic disease, or ones which have been engineered to exhibit such symptoms. For example, tumor progression animal models may be generated by injecting animals, such as mice, with tumor cells, some of which will give rise to tumors within the injected animals. Among the cells which may be utilized for such a purpose are cells listed, above, in Section 5.1.1.1, such as the B16 cell variants.

The role of identified gene products (e.g., 030 gene products) can be determined by transfecting cDNAs encoding these gene products into appropriate cell lines, such as, for example, a B16 cell line variant, and analyzing the effect on tumor progression characteristics. For example, the role/function of genes important in the progression of human colorectal cancers are assessed using the KM12c (low metastatic potential) and KM12L4 (highly metastatic) cells implanted into nude mice spleens and the number of hepatic tumors that develop are determined. The function of genes isolated using human colorectal tumors and their hepatic metastases are assessed by expressing the gene in the appropriate KM12 variant. Additionally, the role/function of genes important in the progression of prostatic and breast cancers are assessed using appropriate cell lines described above in Section 5.1.1.1. Importantly, the role/function of genes important in the progression of melanoma, colon, prostate and breast cancers in humans are assessed using biopsy specimens from patients having undergone surgical treatment, as described in Section 5.1.1.1. above.

Further, such systems can include, but are not limited to transgenic animal systems such as those described, above, in Section 5.7.1 below. In vitro systems can include, but are not limited to, cell-based systems comprising cell types known or suspected of contributing to tumor progression. Such cells can be wild type cells, or can be non-wild type cells containing modifications known to or suspected of, contributing to tumor progression. Such systems are discussed in detail, below, in Section 5.7.2. The procedure to identify and isolate the human homologue of the fomy030 gene is described, below, in Section 5.7.3.

In further characterizing the biological function of the identified genes, the expression of these genes can be modulated within the in vivo and/or in vitro systems, i.e., either over- or under-expressed, and the subsequent effect on the system then assayed. Alternatively, the activity of the product of the identified gene can be modulated by either increasing or decreasing the level of activity in the in vivo and/or in vitro system of interest, and its subsequent effect then assayed.

The information obtained through such characterizations can suggest relevant methods for the treatment of tumor progression and tumor progression disorders involving the gene of interest. Further, relevant methods for controlling the spread of tumor cells involving the gene of interest can be suggested by information obtained from such characterization. For example, treatment can include a modulation of gene expression and/or gene product activity. Characterization procedures such as those described herein can indicate where such modulation should involve an increase or a decrease in the expression or activity of the gene or gene product of interest. Such methods of treatment are discussed, below, in Section 5.9.

5.4. DIFFERENTIALLY EXPRESSED AND PATHWAY GENES

Differentially expressed genes, such as those identified in Section 5.1.1, above, and pathway genes, such as those identified in Section 5.2, above, are described herein.

The differentially expressed and pathway genes of the invention are listed below, in Table 1. The nucleotide sequence for the differentially expressed fomy030 gene is shown in FIGS. 2 and 3A and 3C. Specifically, FIG. 2 depicts the nucleotide sequence (SEQ ID NO:1) of the amplified cDNA band initially identified via differential display analysis, which is referred to herein as romy030. FIGS. 3A and 3C depict the nucleotide sequence (SEQ ID NO:2) of a fomy030 cDNA clone which was isolated using a romy030 probe. The deduced amino acid sequence also is shown in FIGS. 3A and 3C (SEQ ID NO:3). FIGS. 5A–5G shows the nucleotide (SEQ ID NO:6) and deduced amino acid sequences (SEQ ID NO:7) of a fohy030 cDNA clone which was isolated using the entire mouse fomy030 cDNA as a probe. FIGS. 6A–6H shows an alternative splice form of fohy030 (SEQ ID NOs:8 and 9).

Table 1 summarizes information regarding the further characterization of the differentially expressed fomy030 gene of the invention. Table 2 lists *E. coli* clones, deposited with the Agricultural Research Service Culture Collection (NRRL), which contain sequences found within the genes of Table 1.

In Table 1, the paradigm used initially to detect the differentially expressed gene is described under the column headed "Paradigm of original Detection." In this column, "↑" indicates that gene expression is higher (i.e., there is a greater steady state amount of detectable mRNA produced by a given gene) in the indicated cell type relative to the other cell type, while "↓" indicates that gene expression is lower (i.e., there is a lower steady state amount of detectable mRNA, produced by a given gene) in the indicated cell type relative to the other cell type. As indicated under this column, the 030 gene was initially identified via a differential screen between B16 F1 (low metastatic potential cells) and B16 F10 (high metastatic potential cells) in which 030 gene expression is lower in the high metastatic potential B16 F10 cell line than in the low metastatic potential B16 F1 cell line.

The Table 1 column headed "Paradigm Expression Pattern" lists the cell type in which gene expression was initially detected. In the case of the 030 gene, gene expression was first detected in melanoma (i.e., 16) cells. "Detectable" as used herein, refers to levels of mRNA which are detectable, via standard differential display, Northern, RT-coupled PCR and/or RNase protection techniques which are well known to those of skill in the art.

Cell types in which differential expression was detected are summarized in Table 1 under the column headed "Cell Type Detected in." In the case of the 030 gene, expression has additionally been detected within melanocyte cells.

Additionally, in instances wherein the genes contain nucleotide sequences similar or homologous to sequences found in nucleic acid databases, references to such similarities are listed. Because the 030 gene is a novel gene, i.e., no homologous gene sequences are present in the published databases, no such reference is listed.

Finally, nucleotide sequences contained within the differentially expressed genes are listed in the Figures indicated under the heading "Seq." In the case of the fomy030 gene, such sequences are listed in FIGS. 2 and 3A and 3C, and for fohy030, in FIGS. 5A–5G and 6A–6H.

The genes listed in Table 1 can be obtained using cloning methods well known to those skilled in the art, including, but not limited to, the use of appropriate probes to detect the genes within an appropriate cDNA or gDNA (genomic DNA) library. (See, for example, Sambrook et al., 1989, Molecular Cloning: A Laboratory Manual, Cold Spring Harbor Laboratories, which is incorporated by reference herein in its entirety). Probes for the novel sequences reported herein can be obtained directly from the isolated clones deposited with the NRRL, as indicated in Table 2, below. Alternatively, oligonucleotide probes for the novel genes can be synthesized, using techniques well known to those of skill in the art, based on the DNA sequences disclosed herein in FIGS. 2, 3A–3C, 5A–5G, and 6A–6H.

The probes can be used to screen cDNA libraries prepared from an appropriate cell or cell line in which the gene is transcribed. For example, the genes described herein that were detected in melanocyte cells can be cloned from a cDNA library prepared from melanocyte cells such as, for example, melan-c (Hodgkinson, C. A., et al., 1993, Cell 74:395–404), the cDNA libraries developed from the human melanoma cell line A2058 (Clontech, Palo Alto, Calif.) and cDNA libraries developed from the murine melanoma cell line K1735 (Stratagene, La Jolla, Calif.). Genomic DNA libraries can be prepared from any source.

Table 2, below, lists an *E. coli* strain as deposited with the NRRL, which contains an isolated plasmid fomy030 clone. The clone contains a fomy030 cDNA in a pBlueScript SK- (Stratagene, La Jolla, Calif.) vector which was isolated from a mouse melanocyte cDNA library screened with a romy030 probe, as described in Section 6.2, below.

TABLE 2

| GENE | STRAIN DEPOSITED WITH NRRL | PLASMID CLONE CONTAINED WITHIN DEPOSITED STRAIN |
|---|---|---|
| fomy030<br>fohy030 | FOMY030 | pFOMY030 |

As used herein, "differentially expressed gene" (i.e., target and fingerprint genes) or "pathway gene" refers to (a) a gene containing: at least one of the DNA sequences disclosed herein (as shown in FIGS. 2, 3A–3C, 5A–5G, and 6A–6H) or contained in the clones listed in Table 2, as deposited with the NRRL; (b) any DNA sequence that encodes the amino acid sequence encoded by: the DNA sequences disclosed herein (as shown in FIGS. 2, 3A–3C, 5A–5G, and 6A–6H), contained in the clones, listed in Table 2, as deposited with the NRRL or contained within the coding region of the gene to which the DNA sequences disclosed herein (as shown in FIGS. 2, 3A–3C, 5A–5G, and 6A–6H) or contained in the clones listed in Table 2, as deposited with the NRRL, belong; (c) any DNA sequence that hybridizes to the complement of: the coding sequences disclosed herein (as shown in FIGS. 2, 3A–3C, 5A–5G, and 6A–6H), contained in clones listed in Table 2, as deposited with the NRRL, or contained within the coding region of the gene to which the DNA sequences disclosed herein (as shown in FIGS. 2, 3A–3C, 5A–5G, and 6A–6H) or contained in the clones listed in Table 2, as deposited with the NRRL, belong under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 210.3) and encodes a gene product functionally equivalent to a gene product encoded by a gene of (a), above and/or (d) any DNA sequence that hybridizes to the complement of: the coding sequences disclosed herein, (as shown in FIGS. 2, 3A–3C, 5A–5G, and 6A–6H) contained in the clones listed in Table 2, as deposited with the NRRL or contained within the coding region of the gene to which DNA sequences disclosed herein (as shown in

TABLE 1

Differentially Expressed and Pathway Genes

| GENE | Sequence ID | Paradigm of Original Detection (↑/↓) | Paradigm Expression Pattern | Cell Type Detected in | Ref. | Seq. |
|---|---|---|---|---|---|---|
| fomy030 | 2 | B15 ↑ F1<br>B15 ↓ F10 | melanoma cells | melanocyte | | FIG. 2, 3A–3C, 5A–5G & 6A–6H |
| fohy030 | 6 & 8 | benign nevi ↑ malignant melanoma ↓ | biopsy samples | melanocyte | | |

FIGS. 2, 3A–3C, 5A–5G, and 6A–6H) or contained in the clones, listed in Table 2, as deposited with the NRRL, belong under less stringent conditions, such as moderately stringent conditions, e.g., washing in 0.2×SSC/0.1% SDS at 42° C. (Ausubel et al., 1989, supra), yet which still encodes a gene product functionally equivalent to a gene product encoded by a gene of (a), above.

The invention also includes nucleic acid molecules preferably DNA molecules, that hybridize to, and are therefore the complements of, the DNA sequences (a) through (d), in the preceding paragraph. Such hybridization conditions can be highly stringent or less highly stringent, as described above. In instances wherein the nucleic acid molecules are deoxyoligonucleotides ("oligos"), highly stringent conditions can refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules can act as target gene antisense molecules, useful, for example, in target gene regulation and/or as antisense primers in amplification reactions of target, fingerprint, and/or pathway gene nucleic acid sequences. Further, such sequences can be used as part of ribozyme and/or triple helix sequences, also useful for target gene regulation. Still further, such molecules can be used as components of diagnostic methods whereby tumor progression disorders can be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. The invention includes fragments of any of the DNA sequences disclosed herein.

In addition to the gene sequences described above, homologues of these gene sequences as can, for example be present in other species, preferably human in instances wherein the above described gene sequences are not human gene sequences, can be identified and can readily be isolated, without undue experimentation, by molecular biological techniques well known in the art. Further, there can exist genes at other genetic loci within the genome that encode proteins which have extensive homology to one or more domains of such gene products. These genes can also be identified via similar techniques.

For example, the isolated differentially expressed gene sequence can be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment can be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

Further, a previously unknown differentially expressed or pathway gene-type sequence can be isolated by performing PCR using two degenerate oligonucleotide primer pools designed on the basis of amino acid sequences within the gene of interest. The template for the reaction can be cDNA obtained by reverse transcription of mRNA prepared from human or non-human cell lines or tissue known or suspected to express a differentially expressed or pathway gene allele. The PCR product can be subcloned and sequenced to insure that the amplified sequences represent the sequences of a differentially expressed or pathway gene-like nucleic acid sequence.

The PCR fragment can then be used to isolate a full length cDNA clone by a variety of methods. For example, the amplified fragment can be labeled and used to screen a bacteriophage cDNA library. Alternatively, the labeled fragment can be used to screen a genomic library.

PCR technology can also be utilized to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNAase H, and second strand synthesis can then be primed with a poly-C primer. Thus, cDNA sequences upstream of the amplified fragment can easily be isolated. For a review of cloning strategies which can be used, see e.g., Sambrook et al., 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

In cases where the differentially expressed or pathway gene identified is the normal, or wild type, gene, this gene can be used to isolate mutant alleles of the gene. Such an isolation is preferable in processes and disorders which are known or suspected to have a genetic basis. Mutant alleles can be isolated from individuals either known or suspected to have a genotype which contributes to tumor progression symptoms. Mutant alleles and mutant allele products can then be utilized in the therapeutic and diagnostic assay systems described below.

A cDNA of a mutant gene can be isolated, for example, by using PCR, a technique which is well-known to one skilled in the art. In this case, the first cDNA strand can be synthesized by hybridizing a oligo-dT oligonucleotide to mRNA isolated from tissue known or suspected of being expressed in an individual putatively carrying the mutant allele, and by extending the new strand with reverse transcriptase. The second strand of the cDNA can then be synthesized using an oligonucleotide that hybridizes specifically to the 5'- end of the normal gene. Using these two primers, the product is then amplified via PCR, cloned into a suitable vector, and subjected to DNA sequence analysis through methods well-known to one skilled in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof can then be labeled and used as a probe to identify the corresponding mutant allele in the library. The clone containing this gene can then be purified through methods routinely practiced in the art, and subjected to sequence analysis as described, above, in this Section.

Additionally, an expression library can be constructed utilizing DNA isolated from or cDNA synthesized from a tissue known to or suspected of expressing the gene of interest in an individual suspected of or known to carry the mutant allele. In this manner, gene products made by the putatively mutant tissue can be expressed and screened using standard antibody screening techniques in conjunction with antibodies raised against the normal gene product, as described, below, in Section 5.2.3. (For screening techniques, see, for example, Harlow, E. and Lane, eds., 1988, "Antibodies: A Laboratory Manual," Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described in this Section, above.

Taking the fomy030 gene as an example, the fomy030 human homolog can be isolated by a variety of methods. First, sequences found in a murine fomy030 cDNA can be utilized as hybridization probes to detect human fohy030 sequences. This can be accomplished, for example, by probing Southern blots containing total human genomic DNA with a labelled fomy030 probe. Once it is verified that the probe being utilized detects the human 030 gene, one of skill in the art can employ any of several routine approaches to isolate the human gene without undue experimentation.

In one approach, appropriate human cDNA libraries can be screened. Such cDNA libraries can, for example, include human melanocyte, human retina and fetal human brain cDNA libraries. For example, panels of human melanoma cells (such as, for example, SK-MEL-2, ATCC 68-HTB; SK-MEL-5, ATCC 70-HTB; SK-MEL-28, ATCC 72-HTB; G-361, ATCC 1424-CRL,; and/or HT-144 [63-HTB] cells) can be screened for 030 expression by, for example, Northern blot analysis. Upon detection of 030 transcript, cDNA libraries can be constructed from RNA isolated from the appropriate cell line, utilizing standard techniques well known to those of skill in the art. The human cDNA library can then be screened with a 030 probe in order to isolate a human romy030 cDNA. As described below, this method was used to determine the human fohy030 cDNAs in FIGS. 5 and 6.

Alternatively, a human total genomic DNA library can be screened using 030 probes. 030-positive clones can then be sequenced and, further, the intron/exon structure of the human 030 gene may be elucidated. Once genomic sequence is obtained, oligonucleotide primers can be designed based on the sequence for use in the isolation, via, for example RT-coupled PCR, of human 030 cDNA.

The procedures described in these approaches are routine and have been described in detail in Sections 5.1.1.2, 5.3 and 5.7.2.

5.5. DIFFERENTIALLY EXPRESSED AND PATHWAY GENE PRODUCTS

Differentially expressed and pathway gene products include those proteins encoded by the differentially expressed and pathway gene sequences described in Section 5.2.1, above, as for example, the peptide listed in FIG. 3. Specifically, differentially expressed and pathway gene products can include differentially expressed and pathway gene polypeptides encoded by the differentially expressed and pathway gene sequences contained in the clones listed in Table 2, above, as deposited with the NRRL, or contained in the coding regions of the genes to which DNA sequences disclosed herein (in FIGS. 3A, 3B, 5, and 6) or contained in the clones, listed in Table 2, as deposited with the NRRL, belong, for example.

In addition, differentially expressed and pathway gene products can include proteins that represent functionally equivalent gene products. Such an equivalent differentially expressed or pathway gene product can contain deletions, additions or substitutions of amino acid residues within the amino acid sequence encoded by the differentially expressed or pathway gene sequences described, above, in Section 5.2.1, but which result in a silent change thus producing a functionally equivalent differentially expressed on pathway gene product. Amino acid substitutions can be made on the basis of similarity in polarity, charge, solubility, hydrophobicity, hydrophilicity, and/or the amphipatic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent," as utilized herein, refers to either a protein capable exhibiting a substantially similar in vivo activity as the endogenous differentially expressed or pathway gene products encoded by the differentially expressed or pathway gene sequences described in Section 5.2.1, above. Alternatively, when utilized as part of assays such as those described, below, in Section 5.3, "functionally equivalent" can refer to peptides capable of interacting with other cellular or extracellular molecules in a manner substantially similar to the way in which the corresponding portion of the endogenous differentially expressed or pathway gene product would.

The differentially expressed or pathway gene products can be produced by synthetic techniques or via recombinant DNA technology using techniques well known in the art. Methods for preparing the differentially expressed or pathway gene polypeptides and peptides of the invention by expressing nucleic acid encoding differentially expressed or pathway gene sequences are described herein. Methods which are well known to those skilled in the art can be used to construct expression vectors containing differentially expressed or pathway gene protein coding sequences and appropriate transcriptional/translational control signals. These methods include, for example, in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. which is incorporated by reference herein in their entirety, and Ausubel, 1989, supra. Alternatively, RNA capable of encoding differentially expressed or pathway gene protein sequences can be chemically synthesized using, for example, synthesizers. See, for example, the techniques described in "Oligonucleotide Synthesis," 1984, Gait, M. J. ed., IRL Press, Oxford, which is incorporated by reference herein in its entirety.

A variety of host-expression vector systems can be utilized to express the differentially expressed or pathway gene coding sequences of the invention. Such host-expression systems represent vehicles by which the coding sequences of interest can be produced and subsequently purified, but also represent cells which can, when transformed or transfected with the appropriate nucleotide coding sequences, exhibit the differentially expressed or pathway gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed or pathway gene protein coding sequences; yeast (e.g., Saccharomyrces, Pichia) transformed with recombinant yeast expression vectors containing the differentially expressed or pathway gene protein coding sequences; insect cell systems infected with recombinant virus expression vectors (e.g., baculovirus) containing the differentially expressed or pathway gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed or pathway gene protein coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the differentially expressed or pathway gene protein being expressed. For example, when a large quantity of such a protein is to be produced, for the generation of antibodies or to screen peptide libraries, for example, vectors which direct the expression of high levels of fusion protein products that are readily purified can be desirable. Such vectors include, but are not limited, to the *E. coli* expression vector pUR278 (Ruther et al., 1983, EMBO J. 2:1791), in which the differentially expressed or pathway gene protein coding sequence can be ligated individually into the vector in frame with the lacz coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In an insect system, Autographa californica nuclear polyhedrosis virus (AcNPV) is used as a vector to express foreign genes. The virus grows in Spodoptera frugiperda cells. The differentially expressed or pathway gene coding sequence can be cloned individually into non-essential regions (for example the polyhedrin gene) of the virus and placed under control of an AcNPV promoter (for example, the polyhedrin promoter). Successful insertion of differentially expressed or pathway gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Viol. 46:584; Smith, U.S. Pat. No. 4,215,051).

In mammalian host cells, a number of viral-based expression systems can be utilized. In cases where an adenovirus is used as an expression vector, the differentially expressed or pathway gene coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts (e.g., See Logan & Shenk, 1984, Proc. Natl. Acad. Sci. USA 81:3655–3659). Specific initiation signals can also be required for efficient translation of inserted differentially expressed or pathway gene coding sequences. These signals include the ATG initiation codon and adjacent sequences. In cases where an entire identified gene, including its own initiation codon and adjacent sequences, is inserted into the appropriate expression vector, no additional translational control signals can be needed. However, in cases where only a portion of the identified coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc., (see Bittner et al., 1987, Methods in Enzymol. 153:516–544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the differentially expressed or pathway gene protein can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the identified gene protein. Such engineered cell lines can be particularly useful in screening and evaluation of compounds that affect the endogenous activity of the differentially expressed or pathway gene protein.

A number of selection systems can be used, including, but not limited to, the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes in $tk^-$, $hgprt^-$ or $aprt^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 77:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto ni2+ nitriloacetic acid-agarose columns and histidine-tagged proteins are selectively eluted with imidazole-containing buffers.

When used as a component in assay systems such as that described herein, the differentially expressed or pathway gene protein can be labeled, either directly or indirectly, to facilitate detection of a complex formed between the differentially expressed or pathway gene protein and a test substance. Any of a variety of suitable labeling systems can be used including but not limited to radioisotopes such as $^{125}I$; enzyme labelling systems that generate a detectable colorimetric signal or light when exposed to substrate; and fluorescent labels.

Where recombinant DNA technology is used to produce the differentially expressed or pathway gene protein for such assay systems, it can be advantageous to engineer fusion proteins that can facilitate labeling, solubility, immobilization and/or detection.

Indirect labeling involves the use of a third protein, such as a labeled antibody, which specifically binds to either a differentially expressed or pathway gene product. Such antibodies include but are not limited to polyclonal, monoclonal, chimeric, single chain, Fab fragments and fragments produced by a Fab expression library.

5.6. ANTIBODIES SPECIFIC FOR DIFFERENTIALLY EXPRESSED OR PATHWAY GENE PRODUCTS

Described herein are methods for the production of antibodies capable of specifically recognizing one or more differentially expressed or pathway gene epitopes. Such antibodies can include, but are not limited to polyclonal antibodies, monoclonal antibodies (mAbs), humanized or chimeric antibodies, single chain antibodies, Fab fragments, $F(ab')_2$ fragments, fragments produced by a FAb expression library, anti-idiotypic (anti-Id) antibodies, and epitope-binding fragments of any of the above. Such antibodies can be used, for example, in the detection of a fingerprint, target, or pathway gene in a biological sample, or, alternatively, as a method for the inhibition of abnormal target gene activity. Thus, such antibodies can be utilized as tumor progression treatment methods, and/or can be used as part of diagnostic techniques whereby patients can be tested for abnormal levels of fingerprint, target, or pathway gene proteins, or for the presence of abnormal forms of the such proteins.

For the production of antibodies to a differentially expressed or pathway gene, various host animals can be immunized by injection with a differentially expressed or pathway gene protein, or a portion thereof. Such host animals can include but are not limited to rabbits, mice, and rats, to name but a few. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as target gene product (e.g., protein encoded by 030), or an antigenic functional derivative thereof. For the production of polyclonal antibodies, host animals such as those described above, can be immunized by injection with differentially expressed or pathway gene product (e.g., 030) supplemented with adjuvants as also described above.

Monoclonal antibodies, which are homogeneous populations of antibodies to a particular antigen, can be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the BV-hybridoma technique (Cole et al., 1985, Monoclonal Antibodies And Cancer Therapy, Alan R. Liss, Inc., pp. 77–96). Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 3:452–454; U.S. Pat. No. 4,816,567) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) and for making humanized monoclonal antibodies (U.S. Pat. No. 5,225,539, which is incorporated herein by reference in its entirety) can be utilized to produce anti-differentially expressed or anti-pathway gene product antibodies.

Antibody fragments which recognize specific epitopes can be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed (Huse et al., 1989, Science, 246:1275–1281) to allow rapid and easy identification of monoclonal Fab fragments with the desired specificity.

5.7. CELL- AND ANIMAL-BASED MODEL SYSTEMS

Described herein are cell- and animal-based systems which represent reliable models for tumor progression disorders. These systems can be used in a variety of applications. For example, the cell- and animal-based model systems can be used to identify differentially expressed genes via the paradigms described, above, in Section 5.1.1.1. Such systems can also be used to further characterize differentially expressed and pathway genes, as described, above, in Section 5.3. Such further characterization can, for example, indicate that a differentially expressed gene is a target gene, for example. Additionally, such assays can be utilized as part of screening strategies designed to identify compounds which are capable of preventing and/or ameliorating symptoms of tumor progression disorders, including those associated with metastatic diseases, as described, below. Thus, the animal- and cell-based models can be used to identify drugs, pharmaceuticals, therapies and interventions which can be effective in treating tumor progression disorders, such as, for example, metastatic diseases. In addition, as described in detail, below, in Section 5.10.1, such animal models can be used to determine the $LD_{50}$ and the $ED_{50}$ in animal subjects, and such data can be used to determine the if vivo efficacy of potential anti-tumor progression disorder treatments.

5.7.1. ANIMAL-BASED SYSTEMS

Animal-based model systems of tumor progression disorders can be both non-recombinant animals as well as recombinantly engineered transgenic animals.

Non-recombinant animal models for tumor progression can include, for example, murine models of melanoma, prostate cancer and colon cancer. Such models may be generated, for example, by introducing tumor cells into syngeneic mice using techniques such as subcutaneous injection, tail vein injection, spleen implantation, intraperitoneal implantation, implantation under the renal capsule or orthotopic implantation (e.g., colon cancer cells implanted in colonic tissue or prostatic cancer cells implanted in prostate gland). After an appropriate period of time, the tumors which result from these injections can be counted and analyzed.

Among the cells which may be used for the production of such animal models of tumor progression are cells derived from the cell lines listed, above, in Section 5.1.1.1. For example, B16 melanoma cells (Fidler, I. J., 1973, Nature New Biol. 242:148–149), including cell variants exhibiting high (e.g., B16 F10 cells) and low (e.g., B16 F1 cells) metastatic potential may be utilized. Post-injection, pulmonary tumors generally develop in the mouse models. Thus, these animal serve as models of not only melanoma tumor progression but also as models of pulmonary metastases.

For the generation of animal models of colorectal cancers, colon cancer cells such as, for example, KM12c (low metastatic potential) and KM12L4 (highly metastatic) cells (Morikawa, K. et al., 1988, Cancer Research 48:1943–1948) can be implanted into nude mice spleens. In these cases, the animals generally develop hepatic tumors. Thus, such animals serve as models of not only colorectal tumor progression but also as models of hepatic metastases.

For the generation of animal models of prostate cancer tumor progression, cells derived from, for example, the high metastatic potential prostatic cell line PC-3-M or the non-metastatic cell line DU 145 (Karmali, R. A. et al., 1987, Anticancer Res. 7:1173–1180; Koziowski, J. M. et al., 1984, Cancer Research 44:3522–3529) may be implanted into the prostates of animals and the resulting tumors may be analyzed and compared to, for example, normal tissue. In such a manner, genes which are differentially expressed in neoplastic versus normal cells as well as versus metastatic cells may be identified.

The role of identified gene products (e.g., 030 gene products) can be determined by transfecting cDNAs encoding such gene products into the appropriate cell line and analyzing its effect on the cells' ability to induce tumor progression in animal models such as these. The role of the identified gene products may be further analyzed by, for example, culturing calls derived from the tumors which develop in the animal models, introducing these cultured cells into animals, and subsequently measuring the level of identified gene product present in the resulting tumor cells. In this manner, cell line variants are developed which can be useful in analyzing the role of quantitative and/or qualitative differences in the expression of the identified genes on the cells' ability to induce tumor progression. For example, as demonstrated, below, in the Example presented in Section 6, 030 gene expression is inversely related to the metastatic potential of the tumor cell line used to generate such a tumor progression animal model.

Additionally, recombinant animal models exhibiting tumor progression characteristics and/or symptoms of tumor progression disorders, including metastatic diseases, can be utilized, for example, such well-known animal models as the transgenic mouse model for human melanoma and transgenic mice which carry specific mutations which result in multiple intestinal tumors (Mintz, M. and Silvers W. K., 1993, Proc. Natl. Acad. Sci. USA 90:8817–8821; and Fodde, R., et al., 1994, Proc. Natl. Acad. Sci. USA 91:8969–8973). Further, recombinant animal models for tumor progression can be engineered by utilizing, for example, target gene sequences such as those described, above, in Section 5.4, in conjunction with techniques for producing transgenic animals that are well known to those of skill in the art. For example, target gene sequences can be introduced into, and overexpressed in, the genome of the animal of interest, or, if endogenous target gene sequences are present, they can either be overexpressed or, alternatively, can be disrupted in order to underexpress or inactivate target gene expression.

In order to overexpress a target gene sequence, the coding portion of the target gene sequence can be ligated to a regulatory sequence which is capable of driving gene expression in the animal and cell type of interest. Such regulatory regions will be well known to those of skill in the art, and can be utilized in the absence of undue experimentation.

In order to obtain underexpression of an endogenous target gene sequence, such a sequence can be introduced into the genome of the animal of interest such that the endogenous target gene alleles will be inactivated. Preferably, an engineered sequence comprising at least part of the target gene sequence is utilized and is introduced, via gene targeting, such that the endogenous target sequence is disrupted upon integration of the engineered target gene sequence into the animal's genome. Gene targeting is discussed, below, in this Section.

Animals of any species, including, but not limited to, mice, rats, rabbits, guinea pigs, pigs, micro-pigs, goats, and non-human primates, e.g., baboons, monkeys, and chimpanzees can be used to generate animal models of tumor progression and tumor progression disorders, such as, for example, metastatic diseases.

Any technique known in the art can be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the transgene in all their cells, as well as animals which carry the transgene in some, but not all their cells, i.e., mosaic animals. The transgene can be integrated, either as a single transgene or in concatamers, e.g., head-to-head tandems or head-to-tail tandems. The transgene can also be selectively introduced into and activated in a particular cell type by following, for example, the teaching of Lasko et al. (Lasko, M., et al., 1992, Proc. Natl. Acad. Sci. USA 89:6232–6236). The regulatory sequences required for such a cell-type specific activation will depend upon the particular cell type of interest, and will be apparent to those of skill in the art.

When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of, the nucleotide sequence of the endogenous target gene. The transgene can also be selectively introduced into a particular cell type, thus inactivating the endogenous gene of interest in only that cell type, by following, for example, the teaching of Gu et al. (Gu, H., et al., 1994, Science 265:103–106). The regulatory sequences required for such a cell-type specific inactivation will depend upon the particular cell type of interest, and will be apparent to those of skill in the art.

Once transgenic animals have been generated, the expression of the recombinant target gene and protein can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and RT-coupled PCR. Samples of target gene-expressing tissue, can also be evaluated immunocytochemically using antibodies specific for the transgenic product of interest.

The target gene transgenic animals that express target gene mRNA or target gene transgene peptide (detected immunocytochemically, using antibodies directed against target gene product epitopes) at easily detectable levels should then be further evaluated to identify those animals which display tumor progression state characteristics, including tumor progression disorder symptoms. Such tumor progression disorder characteristics and/or symptoms can include, for example, those associated with such tumor cells as found in human melanoma, breast, gastrointestinal, such as esophageal, stomach, colon, bowel, colorectal and rectal cancers, prostate, bladder, testicular, ovarian, uterine, cervical, brain, lung, bronchial, larynx, pharynx, liver, pancreatic, thyroid, bone, leukemias, lymphomas and various types of skin cancers.

Additionally, specific cell types within the transgenic animals can be analyzed for cellular phenotypes characteristic of tumor progression. Such cellular phenotypes can include, for example, differential gene expression characteristic of cells within a given tumor progression state of interest. Further, such cellular phenotypes can include as assessment of a particular cell type fingerprint pattern of expression and its comparison to known fingerprint expression profiles of the particular cell type in animals exhibiting tumor progression. Such transgenic animals serve as suitable model systems for tumor progression disorders.

Once target gene transgenic founder animals are produced (i.e., those animals which express target gene proteins in cells or tissues of interest, and which, preferably, exhibit tumor progression characteristics), they can be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound target gene transgenics that express the target gene transgene of interest at higher levels because of the effects of additive expression of each target gene transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the target gene transgene and the development of symptoms for tumor progression disorders. One such approach is to cross the target gene transgenic founder animals with a wild type strain to produce an F1 generation that exhibits symptoms for tumor progression disorders. The F1 generation can then be inbred in order to develop a homozygous line, if it is found that homozygous target gene transgenic animals are viable.

5.7.2. CELL-BASED ASSAYS

Cells that contain and express target gene sequences which encode target gene protein, and, further, exhibit cellular phenotypes associated with tumor progression disorders, can be utilized to identify compounds that exhibit an ability to prevent and/or ameliorate tumor progression.

Cellular phenotypes which can indicate an ability to ameliorate symptoms of tumor progression disorders can include, for example, tumor cells with low or high metastatic potential.

Further, the fingerprint pattern of gene expression of cells of interest can be analyzed and compared to the normal fingerprint pattern. Those compounds which cause cells exhibiting cellular phenotypes of tumor progression disorders, including metastatic diseases, to produce a fingerprint pattern more closely resembling a normal fingerprint pattern for the cell of interest can be considered candidates for further testing regarding an ability to ameliorate the symptoms of such diseases.

Cells which will be utilized for such assays can, for example, include non-recombinant cell lines, such as, but not limited to, melanoma (e.g., B16 F1 and B16 F10 cell lines), human colon (e.g., KM12c and KM20L4 cell lines), prostate (e.g., DU 145 and PC-3-M cell lines) and breast cancer cell lines (e.g., MCF-7 and MDA-MB-435 cell lines). In addition, purified primary or secondary tumor cells derived from either transgenic or non-transgenic tumor cells can be used.

Further, cells which can be used for such assays can also include recombinant, transgenic cell lines. For example, the metastatic disease animal models of the invention, discussed, above, in Section 5.2.4.1, can be used to generate cell lines, containing one or more cell types involved in metastatic diseases, that can be used as cell culture models for these disorders. While primary cultures derived from the metastasis in transgenic animals of the invention can be utilized, the generation of continuous cell lines is preferred. For examples of techniques which can be used to derive a continuous cell line from the transgenic animals, see Small et al., 1985, Mol. Cell Biol. 5:642–648.

Alternatively, cells of a cell type known to be involved in metastatic diseases can be transfected with sequences capable of increasing or decreasing the amount of target gene expression within the cell. For example, target gene sequences can be introduced into, and over expressed in, the genome of the cell of interest, or, if endogenous target gene sequences are present, they can either be overexpressed or, alternatively, be disrupted in order to underexpress or inactivate target gene expression.

In order to overexpress a target gene sequence, the coding portion of the target gene sequence can be ligated to a regulatory sequence which is capable of driving gene expression in the cell type of interest. Such regulatory regions will be well known to those of skill in the art, and can be utilized in the absence of undue experimentation.

For under expression of an endogenous target gene sequence, such a sequence can be isolated and engineered such that when reintroduced into the genome of the cell type of interest, the endogenous target gene alleles will be inactivated. Preferably, the engineered target gene sequence is introduced via gene targeting such that the endogenous target sequence is disrupted upon integration of the engineered target gene sequence into the cell's genome. Gene targeting is discussed, above, in Section 5.7.1.

Transfection of target gene sequence nucleic acid can be accomplished by utilizing standard techniques. See, for example, Ausubel, 1989, supra. Transfected cells should be evaluated for the presence of the recombinant target gene sequences, for expression and accumulation of target gene mRNA, and for the presence of recombinant target gene protein production. In instances wherein a decrease in target gene expression is desired, standard techniques can be used to demonstrate whether a decrease in endogenous target gene expression and/or in target gene product production is achieved.

5.8. SCREENING ASSAYS FOR COMPOUNDS THAT INTERACT WITH THE TARGET GENE PRODUCT

The following assays are designed to identify compounds that bind to target gene products, bind to other cellular proteins that interact with a target gene product, and to compounds that interfere with the interaction of the target gene product with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of target gene product transmembrane receptors, and members of random peptide libraries (see, e.g., Lam, K. S. et al., 1991, Nature 354:82–84; Houghton, R. et al., 1991, Nature 35:84–86), made of D-and/or L-configuration amino acids, phosphopeptides (including, but not limited to, members of random or partially degenerate phosphopeptide libraries; see, e.g., Songyang, Z. et al., 1993, Call 72:767–778), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules.

Compounds identified via assays such as those described herein can be useful, for example, in elaborating the biological function of the target gene product, and for ameliorating symptoms of tumor progression. In instances, for example, whereby a tumor progression state or disorder results from a lower overall level of target gene expression, target gene product, and/or target gene product activity in a cell involved in the tumor progression state or disorder, compounds that interact with the target gene product can include ones which accentuate or amplify the activity of the bound target gene protein. Such compounds would bring about an effective increase in the level of target gene activity, thus ameliorating symptoms of the tumor progression disorder or state. In instances whereby mutations within the target gene cause aberrant target gene proteins to be made which have a deleterious effect that leads to tumor progression, compounds that bind target gene protein can be identified that inhibit the activity of the bound target gene protein. Assays for testing the effectiveness of compounds, identified by, for example, techniques such as those described in Section 5.8.1–5.8.3, are discussed, below, in Section 5.8.4.

5.8.1. IN VITRO SCREENING ASSAYS FOR COMPOUNDS THAT BIND TO A TARGET GENE PRODUCT

In vitro systems can be designed to identify compounds capable of binding the target gene products of the invention. Compounds identified can be useful, for example, in modulating the activity of wild type and/or mutant target gene products, preferably mutant target gene proteins, can be useful in elaborating the biological function of the target gene product, can be utilized in screens for identifying compounds that disrupt normal target gene interactions, or can in themselves disrupt such interactions.

The principle of the assays used to identify compounds that bind to the target gene product involves preparing a reaction mixture of the target gene protein and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring target gene product or the test substance onto a solid phase and detecting target gene product/test compound complexes anchored on the solid phase at the end of the reaction. In one embodiment of such a method, the target gene product can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene or the test compound to anchor any complexes formed in solution, and a labeled antibody specific for the other component of the possible complex to detect anchored complexes.

5.8.2. ASSAYS FOR CELLULAR PROTEINS THAT INTERACT WITH THE TARGET GENE PRODUCT

Any method suitable for detecting protein-protein interactions can be employed for identifying novel target product-cellular or extracellular protein interactions. These methods are outlined in Section 5.1.3., supra, for the identification of pathway genes, and can be utilized herein with respect to the identification of proteins which interact with identified target proteins. In such a case, the target gene serves as the known "bait" gene.

5.8.3. ASSAYS FOR COMPOUNDS THAT INTERFERE WITH TARGET GENE/CELLULAR PRODUCT INTERACTION

The target gene products of the invention can, in vivo interact with one or more cellular or extracellular macromolecules, such as proteins. Such macromolecules include, but are not limited to, nucleic acid molecules and those products identified via methods such as those described, above, in Section 5.8.2. For the purposes of this discussion, such cellular and extracellular macromolecules are referred to herein as "binding partners." Compounds that disrupt such interactions can be useful in regulating the activity of the target gene product, especially mutant target gene products. Such compounds can include, but are not limited to molecules such as antibodies, peptides, and the like described in Section 5.3.1. above.

The basic principle of the assay systems used to identify compounds that interfere with the interaction between the target gene product and its cellular or extracellular binding partner or partners involves preparing a reaction mixture containing the target gene product, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

The assay for compounds that interfere with the interaction of the target gene products and binding partners can be conducted in a heterogeneous or homogeneous format. Heterogeneous assays involve anchoring either the target gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance; i.e., by adding the test substance to the reaction mixture prior to or simultaneously with the target gene product and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the target gene product or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the target gene product or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene product and the interactive cellular or extracellular binding partner product is prepared in which either the target gene products or their binding partners are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt target gene product-cellular or extracellular binding partner interaction can be identified.

In a particular embodiment, the target gene product can be prepared for immobilization using recombinant DNA techniques described in Section 5.1.2, supra. For example, the target gene coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above, in Section 5.2.4. This antibody can be labeled with the radioactive isotope $^{125}I$, for example, by methods routinely practiced in the art. In a heterogeneous assay, e.g., the GST-Target gene fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the target gene product and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-target gene fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the target gene product and the interactive cellular or extracellular binding partner (in case where the binding partner is a product), in place of one or both of the full length products. Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

5.8.4. ASSAYS FOR AMELIORATION OF TUMOR PROGRESSION SYMPTOMS

Any of the binding compounds, including but not limited to, compounds such as those identified in the foregoing assay systems, can be tested for the ability to prevent and/or ameliorate symptoms of tumor progression and tumor progression disorders, including metastatic disease. Cell-based and animal model-based assays for the identification of compounds exhibiting an ability to prevent and/or ameliorate tumor progression symptoms are described below.

First, cell-based systems such as those described, above, in Section 5.7.2, can be used to identify compounds which can act to ameliorate symptoms of tumor progression For example, such cell systems can be exposed to a compound, suspected to exhibiting an ability to ameliorate tumor progression symptoms, at a sufficient concentration and for a time sufficient to elicit such an amelioration in the exposed cells. After exposure, the cells are examined to determine whether one or more tumor progression state or tumor progression disorder phenotypes has been altered to resemble a more normal or more wild-type, non-neoplastic disease phenotype.

Taking, as an example, tumor progression involving metastasis, cell-based systems such as the highly metastatic B16 F10 melanoma cell line can be utilized. Upon exposure to such cell systems, compounds can be assayed for their ability to reduce the metastatic potential of such cells. Further, the level of 030 gene expression within these cells may be assayed. Presumably, an increase in the observed level of 030 gene expression would indicate an amelioration of the metastatic tumor progression state.

In addition, animal-based systems, such as those described, above, in Section 5.7.1, can be used to identify compounds capable of ameliorating symptoms of tumor progression. Such animal models can be used as test substrates for the identification of drugs, pharmaceuticals, therapies, and interventions which can be effective in treating tumor progression disorders. For example, animal models can be exposed to a compound suspected to exhibit an ability to ameliorate tumor progression symptoms, at a sufficient concentration and for a time sufficient to elicit such an amelioration in the exposed animals. The response of the animals to the exposure can be monitored by assessing the reversal of disorders associated with tumor progression. With regard to intervention, any treatments which reverse any aspect of symptoms of tumor progression, such as, for example, those associated with metastatic disease, should be considered as candidates for human therapeutic intervention in the treatment of tumor progression. Dosages of test agents can be determined by deriving dose-response curves, as discussed in Section 5.10, below.

Further, gene expression patterns can be utilized to assess the ability of a compound to ameliorate symptoms of tumor progression and tumor progression disorders. For example, fingerprint gene expression or a fingerprint pattern can then be used in such an assessment. Fingerprint gene expression and fingerprint patterns are described, below, in Section 5.11.

Fingerprint patterns can be characterized for known states (e.g., normal or known pre-neoplastic, neoplastic or metastatic states) within the cell- and/or animal-based model systems. Subsequently, these known fingerprint patterns can be compared to ascertain the effect a test compound has to modify such fingerprint patterns, and to cause the pattern to more closely resemble that of a more desirable fingerprint pattern.

For example, administration of a compound can cause the fingerprint pattern of a metastatic disease model system to more closely resemble a control, normal system. Administration of a compound can, alternatively, cause the fingerprint pattern of a control system to begin to mimic tumor progression states, such as metastatic disease states.

5.8.5. MONITORING OF EFFECTS DURING CLINICAL TRIALS

Monitoring the influence of compounds on tumor progression can be applied not only in basic drug screening, but also in clinical trials. In such clinical trials, the expression of a panel of genes that have been discovered in any one of the paradigms discovered in Section 5.1.1.1 can be used as a "read out" of the tumor progression state of a particular cell.

For example, and not by way of limitation, the paradigm describing the B16 melanoma cells provides for the identification of fingerprint genes (e.g., 030) that are down-regulated in metastatic tumor cells. For example, in a clinical trial, tumor cells can be isolated from the primary tumors removed by surgery, and RNA prepared and analyzed by differential display as described in Section 6.1. The levels of expression of the fingerprint genes can be quantified by Northern blot analysis or RT-PCR, as described in Section 6.1, or alternatively by measuring the amount of protein produced, by one of the methods described in Section 5.7.2. In this way, the fingerprint profiles can serve as putative biomarkers indicative of the metastatic potential of the tumor cell. Thus, by monitoring the level of expression of romy030, a protocol for suitable chemotherapeutic anticancer drugs can be developed based on the metastatic potential of tumor cells in the primary. In cases of inoperable metastatic disease, patients can have biopsies removed for measurement of romy030 expression so that the drug's efficacy can be measured by monitoring the degree of restored expression of romy030.

5.9. COMPOUNDS AND METHODS FOR TREATMENT OF TUMOR PROGRESSION

Described herein are methods and compositions which can be used ameliorate symptoms of tumor progression and disorders involving tumor progression via, first, target gene modulation, and/or second, via a depletion of the cells involved in tumor progression. Target gene modulation can be of a positive or negative nature, depending on the specific situation involved, but each modulatory event yields a net result in which tumor progression symptoms are ameliorated.

"Negative modulation," as used herein, refers to a reduction in the level and/or activity of target gene product relative to the level and/or activity of the target gene product in the absence of the modulatory treatment.

"Positive modulation," as used herein, refers to an increase in the level and/or activity of target gene product relative to the level and/or activity of target gene product in the absence of modulatory treatment.

It is possible that tumor progression can be brought about, at least in part, by an abnormal level of gene product, or by the presence of a gene product exhibiting abnormal activity. As such, the reduction in the level and/or activity of such gene products would bring about the amelioration of tumor progression symptoms. Negative modulatory techniques for the reduction of target gene expression levels or target gene product activity levels are discussed in Section 5.9.1, below.

Alternatively, it is possible that tumor progression can be brought about, at least in part, by the absence or reduction of the level of gene expression, or a reduction in the level of a gene product's activity. As such, an increase in the level of gene expression and/or the activity of such gene products would bring about the amelioration of tumor progression symptoms.

For example, as demonstrated in the Example presented in Section 6, below, a reduction in the level of 030 gene expression correlates with a highly metastatic tumor progression state. A 030 positive modulatory technique which increased 030 gene expression in cells within a highly metastatic tumor progression state should, therefore, act to ameliorate the symptoms of such a state. Further, because the 030 gene product may exhibit general tumor suppressor features, it is possible that a 030 positive modulatory technique could ameliorate symptoms of many tumor progression events.

Positive modulatory techniques for increasing the target gene expression levels or target gene product activity levels are discussed in Section 5.9.2, below.

Additionally, tumor progression treatment techniques whereby the concentration of cells involved in tumor progression are depleted are described, below, in Section 5.9.3.

Among the tumor progression events which may be treated are those associated with human tumors. Such human tumors may include, for example, human melanomas, breast, gastrointestinal, such as esophageal, stomach, colon, bowel, colorectal and rectal cancers, prostate, bladder, testicular, ovarian, uterine, cervical, brain, lung, bronchial, larynx, pharynx, liver, pancreatic, thyroid, bone, leukemias, lymphomas and various types of skin cancers.

5.9.1. NEGATIVE MODULATORY TECHNIQUES

As discussed, above, successful treatment of tumor progression symptoms and of disorders involving tumor progression can be brought about by techniques which serve to inhibit the expression or activity of target gene products.

For example, compounds such as those identified through assays described, above, in Section 5.8, which exhibit negative modulatory activity, can be used in accordance with the invention to prevent and/or ameliorate symptoms of tumor progression, including tumor progression involving metastatic disorders. As discussed in Section 5.8., above, such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, $F(ab')_2$ and FAb expression library fragments, and epitope-binding fragments thereof). Negative modulatory techniques involving antibody administration are described, below, in Section 5.9.1.2. Techniques for the determination and administration of such compounds are described, below, in Section 5.10.

Further, antisense and ribozyme molecules which inhibit expression of the target gene can also be used in accordance with the invention to reduce the level of target gene expression, thus effectively reducing the level of target gene activity. Still further, triple helix molecules can be utilized in reducing the level of target gene activity. Such techniques are described, below, in Section 5.9.1.1.

5.9.1.1. NEGATIVE MODULATORY ANTISENSE, RIBOZYME AND TRIPLE HELIX APPROACHES

Among the compounds which can exhibit the ability to prevent and/or ameliorate symptoms of tumor progression are antisense, ribozyme, and triple helix molecules. Such molecules can be designed to reduce or inhibit either wild type, or if appropriate, mutant target gene activity. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the Target gene nucleotide sequence of interest, are preferred.

Ribozymes are enzymatic RNA molecules capable of catalyzing the specific cleavage of RNA. (For a review, see, for example, Rossi, J., 1994, Current Biology 4:469–471). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA and must include the well-known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding target gene proteins.

Specific ribazyme cleavage sites within any potential RNA target are initially identified by scanning the molecule of interest for ribozyme cleavage sites which include the following sequences, GUA, GUU, and GUC. Once identified, short RNA sequences of between 15 and 20 ribonucleotides corresponding to the region of the target gene containing the cleavage site can be evaluated for predicted structural features, such as secondary structure, that can render the oligonucleotide sequence unsuitable. The suitability of candidate sequences can also be evaluated by testing their accessibility to hybridization with complementary oligonucleotides, using ribonuclease protection assays.

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences can be pyrimidine-based, which will result in TAT and $CGC^+$triplets across the three associated strands of the resulting triple helix. The pyrimidine-rich molecules provide base complementarily to a purine-rich region of a single strand of the duplex in a parallel orientation to that strand. In addition, nucleic acid molecules can be chosen that are purine-rich, for example, contain a stretch of G residues. These molecules will form a triple helix with a DNA duplex that is rich in GC paris, in which the majority of the purine residues are located on a single strand of the targeted duplex, resulting in GGC triplets across the three strands in the triplex.

Alternatively, the potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to reduce or inhibit mutant gene expression, it is possible that the technique utilized can also efficiently reduce or inhibit the transcription (triple helix) and/or translation (antisense, ribozyme) of mRNA produced by normal target gene alleles such that the possibility can arise wherein the concentration of normal target gene product present can be lower than is necessary for a normal phenotype. In such cases, to ensure that substantially normal levels of target gene activity are maintained, nucleic acid molecules that encode and express target gene polypeptides exhibiting normal target gene activity can be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it can be preferable to coadminister normal target gene protein into the cell or tissue in order to maintain the requisite level of cellular or tissue target gene activity.

Anti-sense RNA and DNA, ribozyme and triple helix molecules of the invention can be prepared by any method known in the art for the synthesis of DNA and RNA molecules. These include techniques for chemically synthesizing oligodeoxyribonucleotides and oligoribonucleotides well known in the art such as, for example, solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phospho-diesterase linkages within the oligodeoxyribonucleotide backbone. 5.9.1.2. NEGATIVE MODULATORY ANTIBODY TECHNIQUES Antibodies can be generated which are both specific for target gene product and which reduce target gene product activity. Such antibodies may, therefore, by administered in instances whereby negative modulatory techniques are appropriate for the treatment of tumor progression. Antibodies can be generated using standard techniques described in Section 5.6, above, against the proteins themselves or against peptides corresponding to portions of the proteins. The antibodies include but are not limited to polyclonal, monoclonal, Fab fragments, single chain antibodies, chimeric antibodies, and the like.

In instances where the target gene protein to which the antibody is directed is intracellular and whole antibodies are used, internalizing antibodies can be preferred. However, lipofectin or liposomes can be used to deliver the antibody or a fragment of the Fab region which binds to the target gene epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein can be used. Such peptides can be synthesized chemically or produced via recombinant DNA technology using methods well known in the art (e.g., see Creighton, 1983, supra; and Sambrook et al., 1989, supra). Alternatively, single chain neutralizing antibodies which bind to intracellular target gene product epitopes can also be administered. Such single chain antibodies can be administered, for example, by expressing nucleotide sequences encoding single-chain antibodies within the target cell population by utilizing, for example, techniques such as those described in Marasco et al. (Marasco, W. et al., 1993, Proc. Natl. Acad. sci. USA 90:7889–7893).

In instances where the target gene protein is extracellular, or is a transmembrane protein, any of the administration techniques described, below in Section 5.10 which are appropriate for peptide administration can be utilized to effectively administer inhibitory target gene antibodies to their site of action.

5.9.2. POSITIVE MODULATORY TECHNIQUES

As discussed above, successful treatment of tumor progression symptoms and of disorders involving tumor progression can be brought about by techniques which serve to increase the level of target gene expression or to increase the activity of a target gene product.

For example, compounds such as those identified through assays described, above, in Section 5.8, which exhibit positive modulatory activity can be used in accordance with the invention to ameliorate tumor progression symptoms. As discussed in Section 5.8, above, such molecules can include, but are not limited to, peptides, phosphopeptides, small organic or inorganic molecules, or antibodies (including, for example, polyclonal, monoclonal, humanized, anti-idiotypic, chimeric or single chain antibodies, and FAb, $F(ab')_2$ and FAb expression library fragments, and epitope-binding fragments thereof). Positive modulatory techniques involving antibody administration are described, below, in Section 5.9.2.1.

For example, a target gene protein, at a level sufficient to ameliorate tumor progression symptoms can be administered to a patient exhibiting such symptoms. Any of the techniques discussed, below, in Section 5.10, can be utilized for such administration. One of skill in the art will readily know how to determine the concentration of effective, non-toxic doses of the normal target gene protein, utilizing techniques such as those described, below, in Section 5.10.1.

In instances wherein the compound to be administered is a peptide compound, DNA sequences encoding the peptide compound can, alternatively, be directly administered to a patient exhibiting tumor progression symptoms, at a concentration sufficient to generate the production of an amount of target gene product adequate to ameliorate tumor progression symptoms. Any of the techniques described, below, in Section 5.10, which achieve intracellular administration, can be utilized for the administration of such DNA molecules. The DNA molecules can be produced, for example, by well-known recombinant techniques.

In the case of peptide compounds which act extracellularly, the DNA molecules encoding such peptides can be taken up and expressed by any cell type, so long as a sufficient circulating concentration of peptide results for the elicitation of a reduction in tumor progression symptoms.

In the case of compounds which act intracellularly, the DNA molecules encoding such peptides must be taken up and expressed by cells involved in the tumor progression at a sufficient level to bring about the reduction of tumor progression symptoms.

Any technique which serves to selectively administer DNA molecules to a cell involved in tumor progression is, therefore, preferred for the DNA molecules encoding intracellularly acting peptides.

Further, patients can be treated for symptoms of tumor progression by gene replacement therapy. One or more copies of a normal target gene or a portion of the gene that directs the production of a normal target gene protein-with target gene function can be inserted into cells, using vectors which include, but are not limited to adenovirus, adeno-associated virus, and retrovirus vectors, in addition to other particles that introduce DNA into cells, such as liposomes. Techniques such as those described above can be utilized for the introduction of normal target gene sequences into human cells.

In instances wherein the target gene encodes an extracellular, secreted gene product, such gene replacement techniques may be accomplished either in vivo or in vitro. For such cases, the cell types expressing the target gene is less important than achieving a sufficient circulating concentration of the extracellular molecules for the amelioration of tumor progression symptoms to occur. In vitro, target gene sequences can be introduced into autologous cells. Those cells expressing the target gene sequence of interest can then be reintroduced, preferably by intravenous administration, into the patient such that there results an amelioration of tumor progression symptoms.

In instances wherein the gene replacement involves a gene which encodes a product which acts intracellularly, it is preferred that gene replacement be accomplished in vivo. Further, because the cell type in which the gene replacement must occur is the cell type involved in tumor progression, such techniques must successfully target such tumor progression cells.

Taking the 030 gene as an example, an increase in 030 expression can serve to ameliorate tumor progression symptoms, such as, for example, tumor progression symptoms involving metastatic processes. Therefore, any positive modulatory described herein which increases the 030 gene product or gene product activity to a level which is sufficient to ameliorate tumor progression symptoms represents a successful tumor progression therapeutic treatment.

5.9.3. METHODS FOR DEPLETING CELLS INVOLVED IN TUMOR PROGRESSION

Techniques described herein can be utilized to deplete the total number of cells involved in tumor progression, thus effectively decreasing the ratio of the tumor cells to non-cancerous cells. Specifically, separation techniques are described which can be used to deplete the total number of tumor cells present within a cell population, and, further, targeting techniques are described which can be utilized to deplete specific tumor cell subpopulations.

Depending on the particular application, changing the number of cells belonging to tumor cell population can yield inhibitory responses leading to the amelioration of cancerous disorders.

The separation techniques described herein are based on the presence or absence of specific cell surface, preferably transmembrane, markers. By way of example, and not by way of limitation, the techniques described herein utilize tumor specific cell surface markers or antigens and will describe procedures whereby tumor cells can be separated from other cells, thus allowing for selective depletion of tumor cells.

Separation techniques can be utilized which separate and purify cells, tumor cells, for example, in vitro from a population of cells, such as hematopoietic cells autologous to the patient being treated. For example, an initial tumor cell subpopulation-containing population of cells, such as hematopoietic cells, can be obtained from a leukemia patient using standard procedures well known to those of skill in the art. Peripheral blood can be utilized as one potential starting source for such techniques, and can, for example, be obtained via venipuncture and collection into heparinized tubes.

Once the starting source of autologous cells is obtained, tumor cells can be removed, and thus selectively separated and purified, by various methods which utilize antibodies which bind specific markers present on tumor cells while absent on other cells within the starting source. These techniques can include, for example, flow cytometry using a fluorescence activated cell sorter (FACS) and specific fluorochromes, biotin-avidin or biotin-streptavidin separations using biotin conjugated to cell surface marker-specific antibodies and avidin or streptavidin bound to a solid support such as affinity column matrix or plastic surfaces or magnetic separations using antibody-coated magnetic beads.

Separation via antibodies for specific markers can be by negative or positive selection procedures. In negative separation, antibodies are used which are specific for markers present on undesired cells, in this case tumor cells, which exhibit, for example, the tumor specific cell surface marker. Cells bound by an antibody to such a cell surface marker can be removed or lysed and the remaining desired mixture retained. In positive separation, antibodies specific for markers present on the desired cells of interest, in this case tumor-like cells, are used. Cells bound by the antibody are separated and retained. It will be understood that positive and negative separations can be used substantially simultaneously or in a sequential manner.

A common technique for antibody based separation is the use of flow cytometry such as by a florescence activated cell sorter (FACS). Typically, separation by flow cytometry is performed as follows. The suspended mixture of cells are centrifuged and resuspended in media. Antibodies which are conjugated to fluorochrome are added to allow the binding of the antibodies to specific cell surface markers. The cell mixture is then washed by one or more centrifugation and resuspension steps. The mixture is run through a FACS which separates the cells based on different fluorescence characteristics. FACS systems are available in varying levels of performance and ability, including multi-color analysis. The facilitating cell can be identified by a characteristic profile of forward and side scatter which is influenced by size and granularity, as well as by positive and/or negative expression of certain cell surface markers.

Other separation techniques besides flow cytometry can also provide fast separations. One such method is biotin-avidin based separation by affinity chromatography. Typically, such a technique is performed by incubating cells with biotin-coupled antibodies to specific markers, such as, for example, the transmembrane protein encoded by the tumor-specific marker, followed by passage through an avidin column. Biotin-antibody-cell complexes bind to the column via the biotin-avidin interaction, while other cells pass through the column. The specificity of the biotin-avidin system is well suited for rapid positive separation. Multiple passages can ensure separation of a sufficient level of the tumor cell subpopulation of interest.

In instances whereby the goal of the separation technique is to deplete the overall number of cells ant belonging to the tumor cell subpopulation, the cells derived from the starting source of cells which has now been effectively depleted of tumor cells can be reintroduced into the patient. Such a depletion of the tumor cell subpopulation results in the amelioration of cancerous disorders associated with tumor progression.

In instances whereby the goal of the separation technique is to augment or increase the overall number of cells belonging to a non-cancerous cell subpopulation, cells derived from the purified normal cell subpopulation can be reintroduced into the patient, thus resulting in the amelioration of cancerous disorders associated with an under activity of the normal cell subpopulation.

The cells to be reintroduced will be cultured and expanded ex vivo prior to reintroduction. Purified normal cell subpopulation cells can be washed, suspended in, for example, buffered saline, and reintroduced into the patient via intravenous administration.

Cells to be expanded can be cultured, using standard procedures, in the presence of an appropriate expansion agent which induces proliferation of the purified normal cell subpopulation. Such an expansion agent can, for example, be any appropriate cytokine, antigen, or antibody.

Prior to being reintroduced into a patient, the purified normal cells can be modified by, for example, transformation with gene sequences encoding gene products of interest. Such gene products should represent products which enhance the activity of the purified normal cell subpopulation or, alternatively, represent products which repress the activity of one or more of the other normal cell subpopulations. Cell transformation and gene expression procedures are well known to those of skill in the art, and can be as those described, above, in Section 5.2.

Well-known targeting methods can, additionally, be utilized in instances wherein the goal is to deplete the number of cells belonging to a specific tumor cell subpopulation. Such targeting methods can be in vivo or in vitro, and can involve the introduction of targeting agents into a population of cells such that the targeting agents selectively destroy a specific subset of the cells within the population. In vivo administration techniques which can be followed for such targeting agents are described, below, in Section 5.10.

Targeting agents generally comprise, first, a targeting moiety which, in the current instance, causes the targeting agent to selectively associate with a specific tumor cell subpopulation. The targeting agents generally comprise, second, a moiety capable of destroying a cell with which the targeting agent has become associated.

Targeting moieties can include, but are not limited to, antibodies directed to cell surface markers found specifically on the tumor cell subpopulation being targeted, or, alternatively, to ligands, such as growth factors, which bind receptor-type molecules found exclusively on the targeted tumor cell subpopulation.

Destructive moieties include any moiety capable of inactivating or destroying a cell to which the targeting agent has become bound. For example, a destructive moiety can include, but it is not limited to cytotoxins or radioactive agents. Cytotoxins include, for example, plant-, fungus-, or bacteria-derived toxins, with deglycosylated Ricin A chain toxins being generally preferred due to their potency and lengthy half-lives.

5.10. PHARMACEUTICAL PREPARATIONS AND METHODS OF ADMINISTRATION

The identified compounds that inhibit target gene expression, synthesis and/or activity can be administered to a patient at therapeutically effective doses to prevent, treat or ameliorate tumor progression. A therapeutically effective dose refers to that amount of the compound sufficient to result in amelioration of symptoms of tumor progression.

5.10.1. EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

5.10.2. FORMULATIONS AND USE

Pharmaceutical compositions for use in accordance with the present invention can be formulated in conventional manner using one or more physiologically acceptable carriers or excipients.

Thus, the compounds and their physiologically acceptable salts and solvates can be formulated for administration by inhalation or insufflation (either through the mouth or the nose) or oral, buccal, parent oral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

5.11. DIAGNOSIS OF TUMOR PROGRESSION

A variety of methods can be employed for the diagnosis of tumor progression and of disorders involving tumor progression, including metastatic diseases. Such methods can, for example, utilize reagents such as fingerprint gene nucleotide sequences described in Sections 5.2.1, and antibodies directed against differentially expressed and pathway gene peptides, as described, above, in Section 5.2.1 (peptides) and 5.2.3 (antibodies). Specifically, such reagents can be used, for example, for the detection of the presence of target gene mutations, or the detection of either over or under expression of target gene in RNA.

The methods described herein can be performed, for example, by utilizing pre-packaged diagnostic kits comprising at least one specific fingerprint gene nucleic acid or anti-fingerprint gene antibody reagent described herein, which can be conveniently used, e.g., in clinical settings, to diagnose patients exhibiting symptoms of metastatic diseases.

Any cell type or tissue, preferably T-cells, in which the fingerprint gene is expressed can be utilized in he diagnostics described below.

5.11.1. DETECTION OF FINGERPRINT GENE NUCLEIC ACIDS

DNA or RNA from the cell type or tissue to be analyzed can easily be isolated using procedures which are well known to those in the art. Diagnostic procedures can also be performed "in situ" directly upon tissue sections (fixed and/or frozen) of patient tissue obtained from biopsies or resections, such that no nucleic acid purification is necessary. Nucleic acid reagents such as those described in Section 5.1 can be used as probes and/or primers for such in situ procedures (see, for example, Nuovo, G. J., 1992, PCR in situ hybridization: Protocols and Applications, Raven Press, N.Y.).

Fingerprint gene nucleotide sequences, either RNA or DNA, can, for example, be used in hybridization or amplification assays of biological samples to detect gene structures and expression associated with metastasis. Such assays can include, but are not limited to, Southern or Northern analyses, single stranded conformational polymorphism analyses, in situ hybridization assays, and, polymerase chain reaction analyses. Such analyses can reveal both quantitative aspects of the expression pattern of the fingerprint gene, and qualitative aspects of the fingerprint gene expression and/or gene composition. That is, such techniques can include, for example, point mutations, insertions, deletions, chromosomal rearrangements, and/or activation or inactivation of gene expression.

Preferred diagnostic methods for the detection of fingerprint gene-specific nucleic acid molecules can involve for example, contacting and incubating nucleic acids, derived from the cell type or tissue being analyzed, with one or more labeled nucleic acid reagents as are described in Section 5.1, under conditions favorable for the specific annealing of these reagents to their complementary sequences within the nucleic acid molecule or interest. Preferably, the lengths of these nucleic acid reagents are at least 15 to 30 nucleotides. After incubation, all non-annealed nucleic acids are removed from the nucleic acid:fingerprint RNA molecule hybrid. The presence of nucleic acids from the target tissue which have hybridized, if any such molecules exist, is then detected. Using such a detection scheme, the nucleic acid from the tissue or cell type of interest can be immobilized, for example, to a solid support such as a membrane, or a plastic surface such as that on a microtitre plate or polystyrene beads. In this case, after incubation, non-annealed, labeled fingerprint nucleic acid reagents of the type described in Section 5.1 are easily removed. Detection of the remaining, annealed, labeled nucleic acid reagents is accomplished using standard techniques well-known to those in the art.

Alternative diagnostic methods for the detection of fingerprint gene specific nucleic acid molecules can involve their amplification, e.g., by PCR (the experimental embodiment set forth in Mullis, K. B., 1987, U.S. Pat. No. 4,683,202), ligase chain reaction (Barany, F., 1991, Proc. Natl. Acad. Sci. USA 88:189–193), self sustained sequence replication (Guatelli, J. C. et al., 1990, Proc. Natl. Acad. Sci. USA 87:1874–1878), transcriptional amplification system (Kwoh, D. Y et al., 1989, Proc. Natl. Acad. Sci. USA 86:1173–1177), Q-Beta Replicase (Lizardi, P. M. et al., 1988, Bi/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA can be isolated include any tissue in which wild type fingerprint gene is known to be expressed. A sequence within the cDNA is then used as the template for a nucleic acid amplification reaction, such as a PCR amplification reaction, or the like.

The nucleic acid reagents used as synthesis initiation reagents (e.g., primers) in the reverse transcription and nucleic acid amplification steps of this method are chosen from among the fingerprint gene nucleic acid reagents described in Section 5.1. The preferred lengths of such nucleic acid reagents are at least 19–30 nucleotides. For detection of the amplified product, the nucleic acid amplification can be performed using radioactively or non-radioactively labeled nucleotides. Alternatively, enough amplified product can be made such that the product can be visualized by standard ethidium bromide staining or by utilizing any other suitable nucleic acid staining method.

In addition to methods which focus primarily on the detection of one nucleic acid sequence, fingerprint profiles, as discussed in Section 5.3.4., can also be assessed in such detection schemes. Fingerprint profiles can be generated, for example, by utilizing a differential display procedure, as discussed above in 5.1.1.2, Northern analysis and/or RT-PCR. Any of the gene sequences described, above, in Section 5.2.1 can be used as probes and/or PCR primers for the generation and corroboration of such fingerprint profiles.

5.11.2. DETECTION OF TARGET GENE PEPTIDES

Antibodies directed against wild type or mutant fingerprint gene peptides, which are discussed, above, in Section 5.2.3, can also be used in tumor progression diagnostics and prognostics, as described, for example, herein. Such diagnostic methods, can be used to detect abnormalities in the level of fingerprint gene protein expression, or abnormalities in the structure and/or tissue, cellular, or subcellular location of fingerprinting gene protein. Structural differences can include, for example, differences in the size, electronegativity, or antigenicity of the mutant fingerprint gene protein relative to the normal fingerprint gene protein.

Protein from the tissue or cell type to be analyzed can easily be isolated using techniques which are well known to those of skill in the art. The protein isolation methods employed herein can, for example, be such as those described in Harlow and Lane (Harlow, E. and Lane, D., 1988, "Antibodies; A Laboratory Manual," Cold Spring Harbor Laboratory Press, Cold spring Harbor, New York), which is incorporated herein by reference in its entirety.

Preferred diagnostic methods for the detection of wild type or mutant fingerprint gene peptide molecules can involve, for example, immunoassays wherein fingerprint gene peptides are detected by their interaction with an anti-fingerprint gene specific peptide antibody.

For example, antibodies, or fragments of antibodies, such as those described, above, in Section 5.2.3, useful in the present invention can be used to quantitatively or qualitatively detect the presence of wild type or mutant fingerprint gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention can, additionally, be employed histologically, as in immunofluorescence or immunoelectron microscopy, for in situ detection of target gene peptides, in situ detection can be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well-known in the art.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene specific antibody. The solid phase support can then be washed with the buffer a second time to remove unbound antibody. The amount of bound label on solid support can then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant fingerprint gene peptide antibody can be determined according to well-known methods. Those skilled in the art will be able to determine operative and optimal assay conditions for each determination by employing routine experimentation.

One of the ways in which the fingerprint gene peptide-specific antibody can be detectably labeled is by linking the same to an enzyme and use in an enzyme immunoassay (EIA) (Voller, A., "The Enzyme Linked Immunosorbent Assay (ELISA)," *Diagnostic Horizons* 2:1–7, 1978) (Microbiological Associates Quarterly Publication, Walkersville, Md.); Voller, A. *et a., J. Clin. Pathol.* 31:507–520 (1978); Butler, J. E., *Meth. Enzymol.* 73:482–523 (1981); Maggio, E. (ed.), *ENZYME IMMUNOASSAY,* CRC Press, Boca Raton, Fla., 1980; Ishikawa, E. at al., (eds.) *ENZYME IMMUNOASSAY,* Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means.

Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays,* Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, O-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

6. EXAMPLE: IDENTIFICATION AND CHARACTERIZATION OF A NOVEL GENE THAT INHIBITS TUMOR PROGRESSION

In the Example presented in this Section, the in vitro paradigm, described, above, in Section 5.1.1.1, was utilized to identify a gene, designated herein as the 030 gene, which is differentially expressed in cells with a high metastatic potential relative to cells having a low metastatic potential. Specifically, the 030 gene is expressed in high metastatic potential cells at a rate which is many-fold lower than it is expressed in non-metastatic cells. Thus, as discussed below, the 030 gene can encode a product important to a number of neoplastic processes, including, for example, the progression of a cell to a metastatic state, the aggressiveness of a cell's metastatic state, and the ability of a primary tumor cell to invade surrounding tissue. Given the differential 030 gene expression pattern revealed in this Section, the 030 gene product can represent a protein having tumor suppressor or inhibitor function.

6.1. MATERIALS AND METHODS

6.1.1. CELL CULTURE

B16 F1 and B16 F10 melanoma cell lines were maintained in culture in Eagle's minimal essential medium (MEM) supplemented with 10% fetal calf serum. Cells were harvested from nonconfluent monolayers by a two minute treatment with 0.25% trypsin and 2 mM EDTA.

For further characterization of in vivo activity, each cell line was injected into mice. Cells were washed two times in MEM, and the final cell suspension adjusted to $5\times10^5$ cells per ml in MEM. Two hundred microliters of this cell suspension ($1\times10^5$ cells) was injected i.v. into the lateral tail vein of C57BL/6J mice. After three weeks, the mice were sacrificed and their lungs autopsied. The number of pulmonary tumors was determined by counting surface nodules using a dissecting microscope.

The differential expression of the 030 gene in B16 F1 relative to B16 F10 cell lines was compared with the extent of pulmonary metastases which developed in B16 F1-injected mice relative to B16 F10-injected mice.

6.1.2. Differential Display

Differential mRNA display was carried out as described, above, in Section 5.1.1.2. Details of the differential display are given, below.

RNA Isolation

RNA was isolated, using RNAzol, from nonconfluent monolayers of B16 F1 and B16 F10 cell lines.

Isolated RNA was resuspended in DEPC $H_2O$ and quantitated by spectrophotometry at $OD_{260}$. Approximately half of the RNA samples were then treated with DNAse I to remove contaminating chromosomal DNA. Each 50 $\mu$l RNA sample (50 $\mu$g), 5.7 $\mu$l 10× PCR buffer (Perkin-ElmeriCetus) and 1 $\mu$l RNAse inhibitor (40 units/$\mu$l; Boehringer Mannheim, Germany) were mixed together. Two microliters of DNAse I (10 units/$\mu$l; Boehringer Mannheim) was added to the reaction which was incubated for 30 min. at 37° C. The total volume was brought to 200 $\mu$l with DEPC $H_2O$, extracted once with phenol/chloroform and precipitated by adding 20 $\mu$l 3M NaOAc, pH 4.8, (DEPC-treated), 500 $\mu$l absolute ETOH and incubated for 1 hour on dry ice. The precipitated sample was centrifuged for 15 min., and the pellet was washed with 70% ETOH. The sample was re-centrifuged, the remaining liquid was aspirated, and the pellet was resuspended in 50 ml $H_2O$. The concentration of RNA was measured by reading the $OD_{260}$.

First Strand cDNA Synthesis

For each RNA sample, duplicate reverse transcription reactions were carried out in parallel. Four hundred ng RNA plus DEPC $H_2O$ in a total volume of 10 $\mu$l were added to 4 $\mu$l $T_{11}CC$ 3' primer (10 $\mu$M; operon). The mixture was incubated at 70° C. for 5 min. to denature the RNA and then placed at room temperature. Twenty-six $\mu$l of reaction mix containing the following components was added to each denatured RNA/primer sample: 8 $\mu$l 5× First Strand Buffer (Gibco/BRL, Gaithersburg, Md.), 4 $\mu$l 0.1M DTT (Gibcol/

BRL), 2 μl RNAse inhibitor (40 units/μl) (Boehringer Mannheim), 4 μl 200 μM dNTP mix, 6 μl $H_2O$, 2 μl Superscript reverse transcriptase (200 units/μl; Gibcol/BRL). The reactions were mixed gently and incubated for 30 min. at 42° C. Sixty μl of $H_2O$, for a final volume of 100 μl, was then added and the samples were denatured for 5 min. at 85° C. and stored at −20° C.

PCR Reactions

The resulting single stranded cDNA molecules were then amplified by PCR. Specifically, 13 μl of reaction mix was added to each tube of a 96 well plate on ice. The reaction mix contained 6.4 μl $H_2O$, 2 μl 10× PCR Buffer (Perkin-Elmer), 2 μl 20 μM dNTPs, 0.4 μl $^{35}S$ dATP (12.5 μCi/μl; 50 μCi total; Dupont/NEN), 2 μl 5' primer OPE4 (5'GTGACATGCC-3'; 10 μM; Operon), and 0.2 μl AmpliTaq™ Polymerase (5 units/μl; Perkin-Elmer). Next, 2 μl of 3' primer ($T_{11}CC$, 10 μM) were added to the side of each tube, followed by 5 μl of cDNA, also to the sides of the tubes, which were still on ice. Tubes were capped and mixed, and brought up to 1000 rpm in a centrifuge, then immediately returned to ice. A Perkin-Elmer 9600 thermal cycler was used, and programmed as follows:

| | |
|---|---|
| 94° C. | 2 min. |
| *94° C. | 15 sec. |
| *40° C. | 2 min. |
| *ramp 72° C. | 1 min. |
| *72° C. | 30 sec. |
| 72° C. | 5 min. |
| 4° C. | hold |

*= x 40

When the thermal cycler initially reached 94° C., the 96 well plate was removed from ice and placed directly into the cycler. Following the amplification reaction, 15 μl of loading dye, containing 80% formamide, 10 mM EDTA, 1 mg/ml xylene cyanole, 1 mg/ml bromphenol blue were added. The loading dye and reaction were mixed, incubated at 85° C. for 5 min., cooled on ice, centrifuged, and placed on ice. Approximately 4 μl from each tube was loaded onto a pre-run (60V) 6% denaturing acrylamide gel. The gel was run at approximately 80V until top dye front was about 1 inch from bottom. The gel was transferred to 3 MM paper (Whatman Paper, England) and dried under vacuum. Bands were visualized by autoradiography.

6.1.3. OTHER TECHNIQUES

Amplified cDNA Band Isolation and Amplification

PCR bands determined to be of interest in the differential display analysis were recovered from the gel and reamplified.

Briefly, differentially expressed bands were excised from the dried gel with a razor blade and placed into a microfuge tube with 100 μl $H_2O$ and heated at 100° C. for 5 min., vortexed, heated again to 100° C. for 5 min., and vortexed again. After cooling, 100 μl $H_2O$, 20 μl 3M NaOAc, 1 μl glycogen (20 mg/ml), and 500 μl ethanol were added and the sample was precipitated on dry ice. After centrifugation, the pellet was washed and resuspended in 10 μl $H_2O$.

DNA isolated from the excised differentially expressed bands were then reamplified by PCR using the following reaction conditions:

| | |
|---|---|
| 58 μl | $H_2O$ |
| 10 μl | 10× PCR Buffer (see above) |
| 10 μl | 200 μM dNTPs |
| 10 μl | 10 μM 3' primer (see above) |
| 10 μl | 10 μM 5' primer (see above) |
| 1.5 μl | amplified band |
| 0.5 μl | AMPLITAQ ® polymerase (5 units/μl; (Perkin Elmer) |

PCR conditions were the same as the initial conditions used to generate the original amplified band, as described, above. After reamplification, glycerol loading dyes were added and samples were loaded onto a 2% preparative TAE/Biogel (Bio101, La Jolla, Calif.) agarose gel and eluted. Bands were then excised from the gel with a razor blade and vortexed for 15 min. at r.t., and purified using the MERMAID™ kit from Bio101 by adding 3 volumes of MERMAID™ high salt binding solution and 8 μl of resuspended glassfog in a microfuge tube. Glassfog was then pelleted, washed 3 times with ethanol wash solution, and then DNA was eluted twice in 10 μl at 50° C.

Subcloning and Sequencing

The TA cloning kit (Invitrogen, San Diego, Calif.) was used to subclone the amplified bands. The ligation reaction typically consisted of 4 μl sterile $H_2O$, 1 μl ligation buffer, 2 μl TA cloning vector, 2 μl PCR product, and 1 μl T4 DNA ligase. The volume of PCR product can vary, but the total volume of PCR product plus $H_2O$ was always 6 μl. Ligations (including vector alone) were incubated overnight at 12° C. before bacterial transformation. TA cloning kit competent bacteria (INVαF': endal, recAl, hsdRl7(r−k, m+k), supE44, λ-, thi-1, gyrA, relal, φ80lacZαΔM15Δ(lacZYA-argF), deoR+, F') were thawed on ice and 2 μl of 0.5 M β-mercaptoethanol were added to each tube. Two μl from each ligation were added to each tube of competent cells (50 μl), mixed without vortexing, and incubated on ice for 30 min. Tubes were then placed in 42° C. bath for exactly 30 sec., before being returned to ice for 2 min. Four hundred-fifty μl of SOC media (Sambrook et al., 1989, supra) were then added to each tube which were then shaken at 37° C. for 1 hr. Bacteria were then pelleted, resuspended in approximately 200 μl SOC and plated on Luria broth agar plates containing X-gal and 60 μg/ml ampicillin and incubated overnight at 37° C. White colonies were then picked and screened for inserts using PCR.

A master mix containing 2 μl 10× PCR buffer, 1.6 μl 2.5 mM dNTP's, 0.1 μl 25 mM $MgCl_2$, 0.2 μl M13 reverse primer (100 ng/μl), 0.2 μl M13 forward primer (100 ng/μl), 0.1 μl AmpliTaq® (Perkin-Elmer)., and 15.8 μl $H_2O$ was made. Forty μl of the master mix were aliquoted into tubes of a 96 well plate, and whole bacteria were added with a pipette tip prior to PCR. The thermal cycler was programmed for insert screening as follows:

| | |
|---|---|
| 94° C. | 2 min. |
| *94° C. | 15 sec. |
| *47° C. | 2 min. |
| *ramp 72° C. | 30 sec. |
| *72° C. | 30 sec. |
| 72° C. | 10 min. |
| 4° C. | hold |

*= x 35

Reaction products were eluted on a 2% agarose gel and compared to vector control. Colonies with vectors containing inserts were purified by streaking onto LB/Amp plates. Vectors were isolated from such strains and subjected to sequence analysis, using an Applied Biosystems Automated Sequencer (Applied Biosystems, Inc. Seattle, Wash.).

Cloning of Human Gene

A human retina cDNA library obtained from Clontech was screened using the entire mouse fomy030 cDNA (FIGS. 3A and 3B) as a probe. During this screen, one million library phage were screened, 53 of which were found to hybridize with the mouse fomy030 probe. The cDNA inserts for eight of these positives were isolated, subcloned, and sequenced.

Comparison of the murine fomy030 and human fohy030 sequences demonstrated a high degree of sequence similarity (86% identical at the nucleotide level and 94.4% identical at the amino acid level) within the 5', 1813 base pairs of their cDNAs. However, beyond this point the sequences diverge and share no significant similarity. The sequence of fomy030 at the point of divergence is GTAG, which corresponds to a consensus splice donor site.

Three independent library isolated cDNAs, as well as a cDNA isolated as a 3' RACE product were found to contain the fomy030 sequence. Thus, the most probable explanation for the divergence of the human and murine sequences is the existence of alternate splice forms of the fomy030 and fohy030 transcripts. The fomy030 splice version results in a protein product of 542 amino acids in length, while the fohy030 splice variant is predicted to encode a protein of 1497 amino acids in length (FIGS. 5A–5G).

Another splice variant is shown in FIGS. 6A–6H (SEQ ID NO:8), and encodes a protein of 1533 amino acids in length (SEQ ID NO:9). The cDNA of FIGS. 5A–5G (SEQ ID NO:6) is missing 34 nucleotides beginning after 2879 in SEQ ID NO:8, and is missing 74 nucleotides beginning after 2926 in SEQ ID NO:8. Thus, nucleotides 2880–2892 in SEQ ID NO:6 are identical to nucleotides 2914–2926 in SEQ ID NO:8, and the sequences are essentially identical starting at 2893 in SEQ ID NO:6 and 3001 in SEQ ID NO:8. The difference in the respective amino acid sequences is that the amino acids are identical from 1 to 844, and then again from 850 to 1497 in SEQ ID NO:7 and from 886 to 1533 in SEQ ID NO:9.

Within their common 5' sequences, fohy030 was also found to have an additional three base pairs (GGA) inserted after position 1394 in the mouse cDNA (at positions 1066–1068 in FIGS. 5A–5G and 6A–6H). These additional three base pairs fall within the open reading frames of both fohy030 and fomy030, and result in an additional Glycine residue at position 356 within the open reading frame of fohy030 relative to fomy030.

Northern Analysis

Northern analysis was performed to confirm the differential expression of the genes corresponding to the amplified bands, as described below.

Twelve micrograms of total RNA sample, 1.5× RNA loading dyes (60% formamide, 9% formaldehyde, 1.5× MOPS, 0.075% × C/BPB dyes) at a final concentration of 1× and $H_2O$ to a final volume of 40 μl were mixed. The tubes were heated at 65° C. for 5 min. and then cooled on ice. The RNA samples analyzed were loaded onto a denaturing 1% agarose gel. The gel was run overnight at 32V in 1×MOPS buffer.

A 300 ml denaturing 1% agarose gel was made as follows. Three grams of agarose (SeaKem™ LE, FMC BioProducts, Rockland, Me.) and 60 ml of 5×MOPS buffer (0.1M MOPS [pH 7.0], 40 mM NaOAc, 5 mM EDTA [pH 8.0]) were added to 210 ml sterile $H_2O$. The mixture was heated until melted, then cooled to 50° C., at which time 5 μl ethidium bromide (5 mg/ml) and 30 ml of 37% formaldehyde were added to the melted gel mixture. The gel was swirled quickly to mix, and then poured immediately.

After electrophoresis, the gel was photographed with a fluorescent ruler, then was washed three times in DEPC $H_2O$, for 20 minutes per wash, at room temperature, with shaking. The RNA was then transferred from the gel to Hybond-N® membrane (Amersham), according to the methods of Sambrook et al., 1989, supra, in 20×SSC overnight.

The probes used to detect mRNA were typically synthesized as follows: 2 μl amplified cDNA band (~30 ng), 7 μl $H_2O$, and 2 μl 10×Hexanucleotide mix (Boehringer-Mannheim) were mixed and heated to 95° C. for 5 min., and then allowed to cool on ice. The volume of the amplified band can vary, but the total volume of the band plus $H_2O$ was always 9 μl. 3 μl dATP/dGTP/dTTP mix (1:1:1 of 0.5 mM each), 5 μl $\alpha^{32}$p dCTP 3000 Ci/mM (50 μCi total; Amersham, Arlington Heights, Ill.), and 1 μl Klenow (2 units; Boehringer-Mannheim) were mixed and incubated at 37° C. After 1 hr., 30 μl TE were added and the reaction was loaded onto a Biospin-6™ column (Biorad, Hercules, Calif.), and centrifuged. A 1 μl aliquot of eluate was used to measure incorporation in a scintillation counter with scintillant to ensure that $10^6$ cpm/μl of incorporation was achieved.

For pre-hybridization, the blot was placed into a roller bottle containing 10 ml of rapid-hyb solution (Amersham), and placed into 65° C. incubator for at least 1 hr. For hybridization, $1\times10^7$ cpm of the probe was then heated to 95° C., chilled on ice, and added to 10 ml of rapid-hyb solution. The prehybridization solution was then replaced with probe solution and incubated for 16 hours at 65° C. The following day, the blot was washed once for 20 min. at room temperature in 2×SSC/0.1% SDS and twice for 15 min. at 65° C. in 0.1×SSC/0.1% SDS before being covered in plastic wrap and put down for exposure.

In Situ Hybridization

10 μm sections of formalin fixed/paraffin embedded benign nevi (non-metastic growths of melanocytes) and malignant melanoma were post-fixed with 4% PFA/PBS for 15 minutes. After washing with PBS, sections were digested with 21 μg/ml proteinase K at 37° C. for 15 minutes, and again incubated with 4% PFA/PBS for 10 minutes. Sections were then washed with PBS, incubated with 0.2 N HCl for 10 minutes, washed with PBS, incubated with 0.25% acetic anhydride/1 M triethanolamine for 10 minutes, washed with PBS, and dehydrated with 70% ethanol and 100% ethanol.

Hybridizations were performed with $^{35}$S-radiolabeled ($5\times10^7$ cpm/ml) cRNA probes encoding a 1.1 kB segment of the coding region of the human cDNA (clone fohy030), and a 1 kB segment of the coding region of the human H4 histone gene in the presence of 50% formamide, 10% dextran sulfate, 1×Denhardt's solution, 600 mM NaCl, 10 mM DTT, 0.25% SDS, and 100 μg/ml tRNA for 18 hours at 55° C. The H4 histone gene was used as a control to show proper transcription of RNA.

After hybridization, slides were washed with 5×SSC at 55° C., 50% formamide/2×SSC at 55° C. for 30 minutes, 10 mM Tris-HCl(pH 7.6)/500 mM NaCl/1 mM EDTA (TNE) at 37° C. for 10 minutes, washed in TNE at 37° C. for 10 minutes, incubated once in 2×SSC at 50° C. for 30 minutes, twice in 0.2×SSC at 50° C. for 30 minutes, and dehydrated with 70% ethanol and 100% ethanol. Localization of mRNA transcripts was detected by dipping slides in Kodak NBT-2 photo-emulsion and exposing for 4 days at 4° C. Controls for the in situ hybridization experiments included the use of a sense probe which showed no signal above backgrounds levels.

6.2. RESULTS

An in vitro paradigm, as described, above, in Section 5.1.1.1, was carried out using the melanoma cell lines, B16 F1 and B16 F10. The B16 F1 cell line exhibits a low metastatic potential, while the B16 F10 cell line exhibits a high metastatic potential. Thus, the two cell lines were grown in vitro as described in Section 6.1.1, RNA was isolated from these cells and differential display carried out as described in Section 6.1.

The differential display analysis identified a band, designated romy030, which represents a cDNA derived from RNA produced by a gene which was expressed at a much higher level in the B16 F1 cells, i, the low metastatic potential cells, relative to the gene's expression in B16 F10 cells, i.e., high metastatic potential cells. The gene corresponding to the romy030 band is referred to herein as the fomy030 or 030 gene.

The amplified romy030 band was isolated, reamplified, subcloned, and sequenced, as described, above, in Section 6.1.3. The romy030 nucleotide sequence (SEQ ID NO:1) is shown in FIG. 2.

A BLAST (Altschul, S. F. et al., 1990, J. Mol. Biol. 215:403–410) database search with the romy030 nucleotide sequence revealed no sequences within the database which are similar to that of romy030. Thus, 030, the gene corresponding to romy030, appears to represent a novel, previously unknown gene which is differentially expressed in cells exhibiting a low metastatic potential relative to those cells exhibiting a high metastatic potential.

To confirm this putative differential regulation, amplified romy030 cDNA was used to probe Northern RNA blots containing RNA from B16 F1 and B16 F10 cells. FIG. 1 shows the results of one such Northern blot analysis, in which it is demonstrated that the steady state levels of fomy030 mRNA are significantly higher in the low metastatic potential cells (i.e., the B16 F1 cells) relative to the high metastatic potential cells (i.e., B16 F10 cells). Lanes 1 and 3 represent F1 cells and Lanes 2 and 4 represent F10 cells respectively. Thus, this Northern analysis confirmed the putative differential fomy030 regulation which had been suggested by the differential display results.

Two specific oligonucleotides were generated based on the sequence of romy030, romy030U 5'-GGGGAAGCACATCAAGGAAC-3' (SEQ ID NO:4) and romy030L 5'-GCAACTACACTCGGAAAAGC-3' (SEQ ID NO:5), for use in PCR reactions. cDNA libraries prepared from mRNA isolated from normal melanocytes and a mouse melanoma cell line were analyzed for the presence of fomy030 by PCR, utilizing the above romy030 probes. Fomy030 was detected in the melanocyte library but not in the melanoma library. The melanoma library was generated from a highly metastatic mouse melanoma K-1735 m2. This result is consistent the observation that fomy030 is present at reduced levels in the metastatic B16 F10 melanoma cell line. A radioactive DNA probe was generated from the subcloned romy030 DNA. This probe was used to screen the normal mouse melanocyte cDNA library. Three independent positive clones were identified and isolated during this screening. These clones were designated fomy030a, fomy030b, and fomy030c. These cDNAs were sequenced and the overlapping portions were found to be identical. The nucleotide sequence of all three fomy030 cDNAs, designated as the fomy030 sequence (SEQ ID NO:2) is depicted in FIGS. 3A–3C, and contains the sequence of romy030. The findings described herein suggest a novel role for fomy030 in tumor progression. A down-regulation of 030 can be used as a diagnostic marker for tumor progression, especially for the progression to metastasis. Further, 030 gene products can be used in the prevention and treatment of tumor progression disorders.

Fohy030 Expression in Human Tissue Samples

To determine whether the fohy030 gene product is differentially expressed in clinically relevant human disease, fohy030 gene expression was analyzed in biopsy sections of human benign nevi (non-metastic growths of melanocytes) and malignant melanoma using in situ hybridization. Fohy030 expression was detected in small intermittent cells in the basal layer of the epidermis (likely, melanocytes) and in the majority of nevus cells in patients diagnosed with benign nevi. No expression of fohy030 was detected in the majority of melanoma cells in patients diagnosed with metastatic melanoma, though expression was detected in normal melanocytic cells in the same tissue section. These results show that the fohy030 gene product is associated with metastasis suppression.

6.3. 030 GENE EXPRESSION IS INVERSELY CORRELATED WITH METASTATIC POTENTIAL

6.3.1. EXPERIMENTAL PROTOCOLS AND RESULTS

The relationship between 030 gene expression and tumor progression was confirmed as described herein. Specifically, the metastatic potentials of six variants of the B16 cell line were tested in animals and the metastatic potential was compared to the level of 030 gene expression observed within the cell variants.

A single cell suspension of B16 F1 cells (low metastatic potential) was injected intravenously into syngeneic C57BL/6 mice. After three weeks, lung tumors were excised and seeded into tissue culture. The following six cell lines were grown in culture: B16 G1, B16 G2, B16 G3, B16 G4, B16 G9 and B16 G12.

To test the metastatic ability of the above listed six tumor cell lines, the same number of cells for each of the six cell lines intravenously into different groups of syngeneic C57BL/6 mice. Three weeks later, the mice were killed and the lungs were removed aseptically. Significantly more number of tumors were observed in mice injected with the following three cell lines: B16 G4, B16 G9 and B16 G12. These results demonstrate that the B16 G4, B16 G9 and B16 G12 cell lines have high metastatic potential and the B16 G1, B16 G2 and B16 G3 cell lines have low metastatic potential.

The lung tumors produced from these three highly metastatic cell lines (B16 G4, B16 G9 and B16 G12) were then excised and seeded into tissue culture to produce the following four cell lines: B16 H5, B16,H6, B16 H7 and B16 H8.

Figure 4:
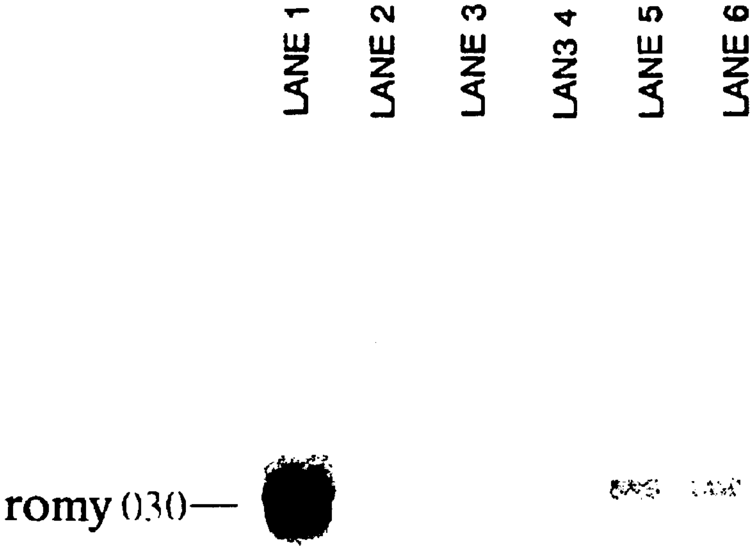
FIG. 4 is a Northern blot analysis confirming differential regulation of the fomy030 gene. Lane 1 is B16 F1, lane 2 is B16 F10, and lanes 3–6 are B16 H5, B16 H6, B16 H7 and B16 H8.

Northern analysis was performed to determine the expression of 030 gene in the above listed cell lines (i.e., B16 H5, B16H6, B16 H7 and B16 H8) using procedures described above in Section 6.1.3. FIG. 4 shows the results of one such Northern blot analysis, in which it is demonstrated that the steady state levels of 030 mRNA are significantly lower in the highly metastatic cells (i.e., B16 H5, B16,H6, B16 H7 and B16 H8) relative to the B16 F1 low metastatic potential cells. Lane 1 represents the B16 F1 cells, lane 2 is B16 F10 metastatic cells and lanes 3–6 represent B16 H5, B16,H6, B16 H7 and B16 H8.

Thus, this Northern analysis confirmed the initial finding in this invention that 030 expression is inversely related to the metastatic potential of tumor cells and supports the theory that the 030 gene product plays a role in inhibiting tumor progression, including the progression to a high metastatic potential state. In this regard, it is important to note that the tumor cell number and homogeneity, and the syngeneic recipient did not change from one cell line to another in the above protocols. Therefore, the differences in metastatic incidence can only be attributed to properties intrinsic to the various cell lines used. The clonal selection of tumors from successive metastases results in cells better capable of survivol, formation and progression of tumor foci in the lung. This indicates that the decrease in expression of 030 observed in the highly metastatic four cell lines (i.e., B16 H5, B16,H6, B16 H7 and B16 H8) is an intrinsic property of these cell lines and is related to the development, progression and metastatic potential of the tumor cells.

7. EXAMPLE: USE OF FINGERPRINT GENES AS SURROGATE MARKERS IN CLINICAL TRIALS

The expression pattern of the fingerprint genes of the invention may be utilized as surrogate markers to monitor clinical human trials of drugs being tested for their efficacy as tumor progression treatments, or may, additionally, be used to monitor patients undergoing clinical evaluation for the treatment of tumor progression. "Fingerprint gene," as used herein is defined as in Section 3, above. Individual fingerprint gene expression patterns may be analyzed or, alternatively, fingerprint patterns may be analyzed. "Fingerprint pattern," as used herein is defined as in Section 3, above.

The effect of the compound on the fingerprint gene expression normally displayed in connection with a disorder involving tumor progression can be used to evaluate the efficacy of the compound as a treatment for such a disorder. Additionally, fingerprint gene expression can be used to monitor patients undergoing clinical evaluation for the treatment of the disorder.

According to the invention, the fingerprint gene expression and fingerprint pattern derived from any of the paradigms described in Section 5.1.1.1 can be used to monitor clinical trials of drugs in human patients. The paradigms described in Section 5.1.1.1, and illustrated in the Example presented in Section 6, above, for example, provide the fingerprint pattern of B16 melanoma cells. This profile gives an indicative reading, therefor, of the metastatic and non-metastatic states of melanoma cells. Accordingly, the influence of anticancer chemotherapeutic agents on the melanoma cells can be measured by performing differential display on melanoma cells of patients undergoing clinical tests.

7.1. TREATMENT OF PATIENTS AND PROCUREMENT OF TUMOR CELLS OR BIOPSIES

Test patients can be administered compounds suspected of antimetastatic activity. Control patients can be given a placebo.

Tumor cells or biopsies can be drawn from each patient after a determined period of treatment and RNA can be isolated as described in Section 6.6.1, above.

7.2. ANALYSIS OF SAMPLES

RNA can be subjected to differential display analysis as described in Section 6.6.1, above. A decrease in the metastatic potential of tumor cells is indicated by an increase in the intensity of the romy030 band, as described in Section 6.2, above.

8. DEPOSIT OF MICROORGANISMS

The following microorganism was deposited with the Agricultural Research Service Culture Collection (NRRL), Peoria, Ill., on Mar. 3, 1995 and assigned the indicated accession number:

| Microorganism | NRRL Accession No. |
|---|---|
| *E. coli* | B-21416 |

The following clones were deposited with the American Type Culture Collection (ATCC), 10801 University Boulevard, Manassas, Va. 20110-2209 on Feb. 11, 1997 and assigned the Indicated accession numbers:

| Clone | ATCC Accession No. |
|---|---|
| Tfohy030<br>(1497 amino acid fohy030 clone; SEQ ID NO:6) | 97880 |
| Nfohy030<br>(1533 amino acid fohy030 clone; SEQ ID NO:8) | 97881 |

OTHER EMBODIMENTS

The present invention is not to be limited in scope by the specific embodiments described which are intended as single illustrations of individual aspects of the invention and functionally equivalent methods and components are within the scope of the invention, in addition to those shown and described herein will become apparent to those skilled in the art from the foregoing description and accompanying drawings. Such modifications are intended to fall within the scope of the appended claims.

What is claimed is:

1. An isolated polypeptide selected from the group consisting of:

a) a polypeptide comprising the amino acid sequence of SEQ ID NO:3;

b) a polypeptide comprising the amino acid sequence of SEQ ID NO:7;

c) a polypeptide comprising the amino acid sequence of SEQ ID NO:9;

d) a polypeptide comprising the amino acid sequence encoded by the cDNA of the clone contained in ATCC Accession No. 97880;

e) a polypeptide comprising the amino acid sequence encoded by the cDNA of the clone contained in ATCC Accession No. 97881;

f) a polypeptide comprising the amino acid sequence encoded by the cDNA of the clone contained in NRRL Deposit No. B-21416;

g) a polypeptide comprising amino acids 1 to 844 of SEQ ID NO:7; and h) a polypeptide comprising amino acids 850 to 1497 of SEQ ID NO:7.

2. The isolated polypeptide of claim 1 wherein the polypeptide comprises the amino acid sequence of SEQ ID NO:3.

3. The isolated polypeptide of claim 1 wherein the polypeptide comprises the amino acid sequence of SEQ ID NO:7.

4. The isolated polypeptide of claim 1 wherein the polypeptide comprises the amino acid sequence of SEQ ID NO:9.

5. The isolated polypeptide of claim 1 wherein the polypeptide comprises the amino acid sequence encoded by the cDNA of the clone contained in NRRL Deposit No. B-21416.

6. The isolated polypeptide of claim 1 wherein the polypeptide comprises the amino acid sequence encoded by the cDNA of the clone contained in ATCC Accession No. 97880.

7. The isolated polypeptide of claim 1 wherein the polypeptide comprises the amino acid sequence encoded by the cDNA of the clone contained in ATCC Accession No. 97881.

8. The isolated polypeptide of claim 1 wherein the polypeptide comprises amino acids 1 to 844 of SEQ ID NO:7.

9. The isolated polypeptide of claim 1 wherein the polypeptide comprises amino acids 850 to 1497 of SEQ ID NO:7.

10. An isolated polypeptide selected from the group consisting of:

a) a polypeptide consisting of 542 amino acids and encoded by a nucleic acid molecule that hybridizes to the complement of the nucleic acid molecule of SEQ ID NO:2 at 68° C. in 0.1×SSC, 0.1% SDS;

b) a polypeptide consisting of 1497 amino acids and encoded by a nucleic acid molecule that hybridizes to the complement of the nucleic acid molecule of SEQ ID NO:6 at 68° C. in 0.1×SSC, 0.1% SDS;

c) a polypeptide consisting of 1533 amino acids and encoded by a nucleic acid molecule that hybridizes to the complement of the nucleic acid molecule of SEQ ID NO:8 at 68° C. in 0.1×SSC, 0.1% SDS;

d) a polypeptide consisting of 542 amino acids and encoded by a nucleic acid molecule that hybridizes to a nucleic acid molecule having the sequence of the complement of the cDNA of the clone contained in NRRL Deposit No. B-21426 at 68° C. in 0.1×SSC, 0.1% SDS;

e) a polypeptide consisting of 1497 amino acids and encoded by a nucleic acid molecule that hybridizes to a nucleic acid molecule having the sequence of the complement of the cDNA of the clone contained in ATCC Accession No. 97880 at 68° C. in 0.1×SSC, 0.1% SDS; and f) a polypeptide consisting of 1533 amino acids and encoded by a nucleic acid molecule that hybridizes to a nucleic acid molecule having the sequence of the complement of the cDNA of the clone contained in ATCC Accession No. 97881 at 68° C. in 0.1×SSC, 0.1% SDS, wherein the presence of the polypeptide in a melanoma cell is associated with decreased metastatic potential of the melanoma cell compared to an otherwise identical melanoma cell that does not express the polypeptide.

11. The isolated polypeptide of claim 10 wherein the polypeptide consists of 542 amino acids and is encoded by a nucleic acid molecule that hybridizes to the complement of the nucleic acid molecule of SEQ ID NO:2 at 68° C. in 0.1×SSC, 0.1% SDS.

12. The isolated polypeptide of claim 10 wherein the polypeptide consists of 1497 amino acids and is encoded by an nucleic acid molecule that hybridizes to the complement of the nucleic acid molecule of SEQ ID NO:6 at 68° C. in 0.1×SSC, 0.1% SDS.

13. The isolated polypeptide of claim 10 wherein the polypeptide consists of 1533 amino acids and is encoded by a nucleic acid molecule that hybridizes to the complement of the nucleic acid molecule of SEQ ID NO:8 at 68° C. in 0.1×SSC, 0.1% SDS.

14. The isolated polypeptide of claim 10 wherein the polypeptide consists of 542 amino acids and is encoded by a nucleic acid molecule that hybridizes to a nucleic acid molecule having the sequence of the complement of the cDNA of the clone contained in NRRL Deposit No. B-21416 at 68° C. in 0.1×SSC, 0.1% SDS.

15. The isolated polypeptide of claim 10 wherein the polypeptide consists of 1497 amino acids and is encoded by a nucleic acid molecule that hybridizes to a nucleic acid molecule having the sequence of the complement of the cDNA of the clone contained in ATCC Accession No. 97880 at 68° C. in 0.1×SSC, 0.1% SDS.

16. The isolated polypeptide of claim 10 wherein the polypeptide consists of 1533 amino acids and is encoded by a nucleic acid molecule that hybridizes to a nucleic acid molecule having the sequence of the complement of the cDNA of the clone contained in ATCC Accession No. 97881 at 68° C. in 0.1×SSC, 0.1% SDS.

* * * * *

SEQUENCE LISTING

```
<160> NUMBER OF SEQ ID NOS: 9

<210> SEQ ID NO 1
<211> LENGTH: 186
```

-continued

```
<212> TYPE: DNA
<213> ORGANISM: Mus musculus

<400> SEQUENCE: 1

ggtgctggag tacctcatgg gcggtgccta ccgctgcaac tacactcgga aaagcttccg     60

gactctctac aacaacttgt ttggccctaa gagggtagag ctcagcagac acacagtgtc    120

ctgtgcctcc cagagtaaca tgtggttcct tgatgtgctt ccccaaaagc ccacctgtgc    180

agaatg                                                               186


<210> SEQ ID NO 2
<211> LENGTH: 2729
<212> TYPE: DNA
<213> ORGANISM: Mus musculus
<220> FEATURE:
<221> NAME/KEY: CDS
<222> LOCATION: (321)...(1946)

<400> SEQUENCE: 2

aaggaggcta ggctgcaccc ttcccgcttg ctcagcagct gaggcagggt cagaaagcat     60

ggatagagaa gacattttgc aaaagggaat gcatctttgt aattcccagt acaaaagacc    120

ctaacagatg ttgctgtggt cagctcacta accagcacat ccccccttttg ccgagtgggg    180

ctcccagcac aacaggagag gacaccaagc aggcagacac gcagtccggg aaatggtctg    240

tcagcaaaca cacccagagc tacccaacag actcctatgg gattcttgaa ttccagggtg    300

ggggttactc caataaagcc atg tac atc cga gtc tcc tac gac acc aag cca    353
                      Met Tyr Ile Arg Val Ser Tyr Asp Thr Lys Pro
                        1               5                  10

gat tcc ctg ctc cac ctc atg gtg aag gac tgg cag ctg gag ctc ccg      401
Asp Ser Leu Leu His Leu Met Val Lys Asp Trp Gln Leu Glu Leu Pro
             15                  20                  25

aag ctc ttg ata tct gtg cac gga ggc ctc caa agc ttc gag atg cag      449
Lys Leu Leu Ile Ser Val His Gly Gly Leu Gln Ser Phe Glu Met Gln
         30                  35                  40

tcc aaa ctg aag cag gtg ttt ggg aaa ggt ctg atc aag gct gcc atg      497
Ser Lys Leu Lys Gln Val Phe Gly Lys Gly Leu Ile Lys Ala Ala Met
     45                  50                  55

acc acg ggg gcg tgg atc ttc acc ggg ggt gtg agc act ggt gtc gtc      545
Thr Thr Gly Ala Trp Ile Phe Thr Gly Gly Val Ser Thr Gly Val Val
 60                  65                  70                  75

agc cat gtg ggg gat gcc ttg aaa gac cac tcc tcc aag tcc aga ggc      593
Ser His Val Gly Asp Ala Leu Lys Asp His Ser Ser Lys Ser Arg Gly
                 80                  85                  90

cgg ctc tgt gct ata gga att gct ccc tgg ggc atg gtg gag aac aag      641
Arg Leu Cys Ala Ile Gly Ile Ala Pro Trp Gly Met Val Glu Asn Lys
             95                 100                 105

gaa gac ctg att gga aaa gat gta aca aga gtc tat cag acc atg tcc      689
Glu Asp Leu Ile Gly Lys Asp Val Thr Arg Val Tyr Gln Thr Met Ser
        110                 115                 120

aac cct ctg agc aag ctc tct gtg ctc aac aat tcc cac act cac ttc      737
Asn Pro Leu Ser Lys Leu Ser Val Leu Asn Asn Ser His Thr His Phe
    125                 130                 135

atc ttg gct gac aac ggc acc ctg ggc aag tat ggt gct gag gtg aag      785
Ile Leu Ala Asp Asn Gly Thr Leu Gly Lys Tyr Gly Ala Glu Val Lys
140                 145                 150                 155

ctt cga aga cag ctg gaa aaa cac atc tcc ctg cag aag atc aac aca      833
Leu Arg Arg Gln Leu Glu Lys His Ile Ser Leu Gln Lys Ile Asn Thr
                160                 165                 170

agg ctg ggc cag ggt gta cct gtc gtg ggc cta gtg gta gaa ggt ggt      881
```

-continued

```
Arg Leu Gly Gln Gly Val Pro Val Val Gly Leu Val Val Glu Gly Gly
            175                 180                 185

cct aac gtg gtt tct atc gtc ctg gag tat ctc aaa gaa gac cct cct      929
Pro Asn Val Val Ser Ile Val Leu Glu Tyr Leu Lys Glu Asp Pro Pro
        190                 195                 200

gtc cct gtg gtg gtt tgc gat ggc agt gga cgt gcc tct gac att ttg      977
Val Pro Val Val Val Cys Asp Gly Ser Gly Arg Ala Ser Asp Ile Leu
    205                 210                 215

tcc ttc gca cac aaa tac tgc gac gaa gga gga gtc ata aac gag tcc     1025
Ser Phe Ala His Lys Tyr Cys Asp Glu Gly Gly Val Ile Asn Glu Ser
220                 225                 230                 235

ctg cgg gac cag ctt cta gtt acc att cag aaa aca ttt aat tac agc     1073
Leu Arg Asp Gln Leu Leu Val Thr Ile Gln Lys Thr Phe Asn Tyr Ser
                240                 245                 250

aag tcc cag tcg tat cag ctg ttt gca att atc atg gag tgc atg aag     1121
Lys Ser Gln Ser Tyr Gln Leu Phe Ala Ile Ile Met Glu Cys Met Lys
            255                 260                 265

aag aaa gaa ctc gtc act gtg ttt cgg atg ggt tcc gag ggt cag caa     1169
Lys Lys Glu Leu Val Thr Val Phe Arg Met Gly Ser Glu Gly Gln Gln
        270                 275                 280

gat gtc gag atg gca att tta act gcc ttg ctc aaa gga acc aac gca     1217
Asp Val Glu Met Ala Ile Leu Thr Ala Leu Leu Lys Gly Thr Asn Ala
    285                 290                 295

tca gct cca gat cag ctg agc ttg gcc ctg gct tgg aac cgg gtc gac     1265
Ser Ala Pro Asp Gln Leu Ser Leu Ala Leu Ala Trp Asn Arg Val Asp
300                 305                 310                 315

ata gcg cga agc cag atc ttc gtc ttt ggc cca cac tgg ccg cca ctg     1313
Ile Ala Arg Ser Gln Ile Phe Val Phe Gly Pro His Trp Pro Pro Leu
                320                 325                 330

gga agc ctg gcc cct cct gtg gac acc aaa gcc gca gag aag gaa aag     1361
Gly Ser Leu Ala Pro Pro Val Asp Thr Lys Ala Ala Glu Lys Glu Lys
            335                 340                 345

aag cca ccc aca gcc acc acc aag ggg aga gga aaa gga aaa ggc aag     1409
Lys Pro Pro Thr Ala Thr Thr Lys Gly Arg Gly Lys Gly Lys Gly Lys
        350                 355                 360

aag aaa ggc aaa gtg aaa gag gaa gtg gag gaa gag acg gac ccc cgg     1457
Lys Lys Gly Lys Val Lys Glu Glu Val Glu Glu Glu Thr Asp Pro Arg
    365                 370                 375

aag ctt gag ctg ctc aac tgg gtg aat gcc ctg gag caa gcc atg ctg     1505
Lys Leu Glu Leu Leu Asn Trp Val Asn Ala Leu Glu Gln Ala Met Leu
380                 385                 390                 395

gat gct ctt gtc cta gat cgg gtg gac ttt gta aag ctc ctg att gaa     1553
Asp Ala Leu Val Leu Asp Arg Val Asp Phe Val Lys Leu Leu Ile Glu
                400                 405                 410

aac gga gtg aac atg cag cat ttc ctc acc atc ccg agg ctg gag gag     1601
Asn Gly Val Asn Met Gln His Phe Leu Thr Ile Pro Arg Leu Glu Glu
            415                 420                 425

cta tac aac acc aga ctg ggc cca cca aac acc ctt cat ctg ctg gtg     1649
Leu Tyr Asn Thr Arg Leu Gly Pro Pro Asn Thr Leu His Leu Leu Val
        430                 435                 440

cgg gat gta aag aag agc aac ctt cca cct gat tac cac atc agc ctc     1697
Arg Asp Val Lys Lys Ser Asn Leu Pro Pro Asp Tyr His Ile Ser Leu
    445                 450                 455

att gat ata gga ctg gtg ctg gag tac ctc atg ggc ggt gcc tac cgc     1745
Ile Asp Ile Gly Leu Val Leu Glu Tyr Leu Met Gly Gly Ala Tyr Arg
460                 465                 470                 475

tgc aac tac act cgg aaa agc ttc cgg act ctc tac aac aac ttg ttt     1793
Cys Asn Tyr Thr Arg Lys Ser Phe Arg Thr Leu Tyr Asn Asn Leu Phe
                480                 485                 490
```

-continued

```
ggc cct aag agg gta gag ctc agc aga cac aca gtg tcc tgt gcc tcc     1841
Gly Pro Lys Arg Val Glu Leu Ser Arg His Thr Val Ser Cys Ala Ser
            495                 500                 505

cag agt aac atg tgg ttc ctt gat gtg ctt ccc caa aag ccc acc tgt     1889
Gln Ser Asn Met Trp Phe Leu Asp Val Leu Pro Gln Lys Pro Thr Cys
        510                 515                 520

gca gaa tgc aac tct tca cct cac ctg tcc caa act gac atc acc cca     1937
Ala Glu Cys Asn Ser Ser Pro His Leu Ser Gln Thr Asp Ile Thr Pro
    525                 530                 535

cct ctg ccc tgacacccag tgcagggcct cctagctttc acatgcagcc             1986
Pro Leu Pro
540

attcacatcg cctctcaaga ctgggccagg cagtgcaacc tgtcaagcat gtctgtcctc   2046

ccctccttcc tacaatagcc ccccctctgg gccccatgcc tctgctctct cagcccgttc   2106

tcctccccac tgatcactgg cgctcctgtt gtcttccaag gcaaggaaca aggaaaagca   2166

tctttttgcc cacaaaagtt tagggctccc cgctgttcaa ccatagccaa cctcactgta   2226

catcggagtc atccaggcca gctgccacac acaagccttc cccaccctat cccaatagac   2286

cctattcctc catcaaaatc aaagctaact cctggcctgc cacattgctt cttcttgctc   2346

cagcctgtta aacctccaat aaatgtcaga tctgtgggaa gccttcctca ctctcactcc   2406

acagtttgta cagagagcga gagcctcgtt tggttctact tacaaggaag gctttgtgtc   2466

tgtctgtcct tcccaactga cttctgttga cagaagcagt ttccacatga aagcgttgac   2526

tcacctggat gttgtcatta attaatagtg atacaaaata ttgacacttc ttttcctgct   2586

tctttgttat gcagccgaaa gcacttaagc ttctgggaat ggaagtaagt aggacatgtt   2646

tgtggcagtt tatttactat atataccttt gtcattctgt ggaagcaaaa attgcaatgt   2706

tttccatgaa taaagctcgt gcc                                           2729


<210> SEQ ID NO 3
<211> LENGTH: 542
<212> TYPE: PRT
<213> ORGANISM: Mus musculus

<400> SEQUENCE: 3

Met Tyr Ile Arg Val Ser Tyr Asp Thr Lys Pro Asp Ser Leu Leu His
  1               5                  10                  15

Leu Met Val Lys Asp Trp Gln Leu Glu Leu Pro Lys Leu Leu Ile Ser
             20                  25                  30

Val His Gly Gly Leu Gln Ser Phe Glu Met Gln Ser Lys Leu Lys Gln
         35                  40                  45

Val Phe Gly Lys Gly Leu Ile Lys Ala Ala Met Thr Thr Gly Ala Trp
     50                  55                  60

Ile Phe Thr Gly Gly Val Ser Thr Gly Val Val Ser His Val Gly Asp
 65                  70                  75                  80

Ala Leu Lys Asp His Ser Ser Lys Ser Arg Gly Arg Leu Cys Ala Ile
                 85                  90                  95

Gly Ile Ala Pro Trp Gly Met Val Glu Asn Lys Glu Asp Leu Ile Gly
            100                 105                 110

Lys Asp Val Thr Arg Val Tyr Gln Thr Met Ser Asn Pro Leu Ser Lys
        115                 120                 125

Leu Ser Val Leu Asn Asn Ser His Thr His Phe Ile Leu Ala Asp Asn
    130                 135                 140

Gly Thr Leu Gly Lys Tyr Gly Ala Glu Val Lys Leu Arg Arg Gln Leu
145                 150                 155                 160
```

-continued

```
Glu Lys His Ile Ser Leu Gln Lys Ile Asn Thr Arg Leu Gly Gln Gly
                165                 170                 175

Val Pro Val Val Gly Leu Val Val Glu Gly Gly Pro Asn Val Val Ser
            180                 185                 190

Ile Val Leu Glu Tyr Leu Lys Glu Asp Pro Pro Val Pro Val Val Val
        195                 200                 205

Cys Asp Gly Ser Gly Arg Ala Ser Asp Ile Leu Ser Phe Ala His Lys
    210                 215                 220

Tyr Cys Asp Glu Gly Gly Val Ile Asn Glu Ser Leu Arg Asp Gln Leu
225                 230                 235                 240

Leu Val Thr Ile Gln Lys Thr Phe Asn Tyr Ser Lys Ser Gln Ser Tyr
                245                 250                 255

Gln Leu Phe Ala Ile Ile Met Glu Cys Met Lys Lys Lys Glu Leu Val
            260                 265                 270

Thr Val Phe Arg Met Gly Ser Glu Gly Gln Gln Asp Val Glu Met Ala
        275                 280                 285

Ile Leu Thr Ala Leu Leu Lys Gly Thr Asn Ala Ser Ala Pro Asp Gln
    290                 295                 300

Leu Ser Leu Ala Leu Ala Trp Asn Arg Val Asp Ile Ala Arg Ser Gln
305                 310                 315                 320

Ile Phe Val Phe Gly Pro His Trp Pro Pro Leu Gly Ser Leu Ala Pro
                325                 330                 335

Pro Val Asp Thr Lys Ala Ala Glu Lys Glu Lys Lys Pro Pro Thr Ala
            340                 345                 350

Thr Thr Lys Gly Arg Gly Lys Gly Lys Gly Lys Lys Lys Gly Lys Val
        355                 360                 365

Lys Glu Glu Val Glu Glu Glu Thr Asp Pro Arg Lys Leu Glu Leu Leu
    370                 375                 380

Asn Trp Val Asn Ala Leu Glu Gln Ala Met Leu Asp Ala Leu Val Leu
385                 390                 395                 400

Asp Arg Val Asp Phe Val Lys Leu Leu Ile Glu Asn Gly Val Asn Met
                405                 410                 415

Gln His Phe Leu Thr Ile Pro Arg Leu Glu Glu Leu Tyr Asn Thr Arg
            420                 425                 430

Leu Gly Pro Pro Asn Thr Leu His Leu Leu Val Arg Asp Val Lys Lys
        435                 440                 445

Ser Asn Leu Pro Pro Asp Tyr His Ile Ser Leu Ile Asp Ile Gly Leu
    450                 455                 460

Val Leu Glu Tyr Leu Met Gly Gly Ala Tyr Arg Cys Asn Tyr Thr Arg
465                 470                 475                 480

Lys Ser Phe Arg Thr Leu Tyr Asn Asn Leu Phe Gly Pro Lys Arg Val
                485                 490                 495

Glu Leu Ser Arg His Thr Val Ser Cys Ala Ser Gln Ser Asn Met Trp
            500                 505                 510

Phe Leu Asp Val Leu Pro Gln Lys Pro Thr Cys Ala Glu Cys Asn Ser
        515                 520                 525

Ser Pro His Leu Ser Gln Thr Asp Ile Thr Pro Pro Leu Pro
    530                 535                 540
```

<210> SEQ ID NO 4
<211> LENGTH: 20
<212> TYPE: DNA
<213> ORGANISM: Artificial Sequence
<220> FEATURE:

-continued

<223> OTHER INFORMATION: primer

<400> SEQUENCE: 4
ggggaagcac atcaaggaac 20

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gcaactacta cactcggaaa agc 23

<210> SEQ ID NO 6
<211> LENGTH: 4944
<212> TYPE: DNA
<213> ORGANISM: Homo sapiens
<220> FEATURE:
<221> NAME/KEY: CDS
<222> LOCATION: (346)...(4836)

<400> SEQUENCE: 6

```
actcattata gggntcgagc ggccgcccgg gcaggtttga gctgtgccct ctccattcca     60

ctgctgtggc agggtcagaa atcttggata gagaaaacct tttgcaaacg ggaatgtatc    120

tttgtaattc ctagcacgaa agactctaac aggtgttgct gtggccagtt caccaaccag    180

catatccccc ctctgccaag tgcaacaccc agcaaaaatg aagaggaaag caaacaggtg    240

gagactcagc ctgagaaatg gtctgttgcc aagcacaccc agagctaccc aacagattcc    300

tatggagttc ttgaattcca gggtggcgga tattccaata aagcc atg tat atc cgt    357
                                                  Met Tyr Ile Arg
                                                    1

gta tcc tat gac acc aag cca gac tca ctg ctc cat ctc atg gtg aaa      405
Val Ser Tyr Asp Thr Lys Pro Asp Ser Leu Leu His Leu Met Val Lys
  5                  10                  15                  20

gat tgg cag ctg gaa ctc ccc aag ctc tta ata tct gtg cat gga ggc      453
Asp Trp Gln Leu Glu Leu Pro Lys Leu Leu Ile Ser Val His Gly Gly
                 25                  30                  35

ctc cag aac ttt gag atg cag ccc aag ctg aaa caa gtc ttt ggg aaa      501
Leu Gln Asn Phe Glu Met Gln Pro Lys Leu Lys Gln Val Phe Gly Lys
             40                  45                  50

ggc ctg atc aag gct gct atg acc acc ggg gcc tgg atc ttc acc ggg      549
Gly Leu Ile Lys Ala Ala Met Thr Thr Gly Ala Trp Ile Phe Thr Gly
         55                  60                  65

ggt gtc agc aca ggt gtt atc agc cac gta ggg gat gcc ttg aaa gac      597
Gly Val Ser Thr Gly Val Ile Ser His Val Gly Asp Ala Leu Lys Asp
     70                  75                  80

cac tcc tcc aag tcc aga ggc cgg gtt tgt gct ata gga att gct cca      645
His Ser Ser Lys Ser Arg Gly Arg Val Cys Ala Ile Gly Ile Ala Pro
 85                  90                  95                 100

tgg ggc atc gtg gag aat aag gaa gac ctg gtt gga aag gat gta aca      693
Trp Gly Ile Val Glu Asn Lys Glu Asp Leu Val Gly Lys Asp Val Thr
                105                 110                 115

aga gtg tac cag acc atg tcc aac cct cta agt aag ctc tct gtg ctc      741
Arg Val Tyr Gln Thr Met Ser Asn Pro Leu Ser Lys Leu Ser Val Leu
            120                 125                 130

aac aac tcc cac acc cac ttc atc ctg gct gac aat ggc acc ctg ggc      789
Asn Asn Ser His Thr His Phe Ile Leu Ala Asp Asn Gly Thr Leu Gly
        135                 140                 145
```

-continued

```
aag tat ggc gcc gag gtg aag ctg cga agg ctg ctg gaa aag cac atc      837
Lys Tyr Gly Ala Glu Val Lys Leu Arg Arg Leu Leu Glu Lys His Ile
    150                 155                 160

tcc ctc cag aag atc aac aca aga ctg ggg cag ggc gtg ccc ctc gtg      885
Ser Leu Gln Lys Ile Asn Thr Arg Leu Gly Gln Gly Val Pro Leu Val
165                 170                 175                 180

ggt ctc gtg gtg gag ggg ggc cct aac gtg gtg tcc atc gtc ttg gaa      933
Gly Leu Val Val Glu Gly Gly Pro Asn Val Val Ser Ile Val Leu Glu
                185                 190                 195

tac ctg caa gaa gag cct ccc atc cct gtg gtg att tgt gat ggc agc      981
Tyr Leu Gln Glu Glu Pro Pro Ile Pro Val Val Ile Cys Asp Gly Ser
            200                 205                 210

gga cgt gcc tcg gac atc ctg tcc ttt gcg cac aag tac tgt gaa gaa     1029
Gly Arg Ala Ser Asp Ile Leu Ser Phe Ala His Lys Tyr Cys Glu Glu
        215                 220                 225

ggc gga ata ata aat gag tcc ctc agg gag cag ctt cta gtt acc att     1077
Gly Gly Ile Ile Asn Glu Ser Leu Arg Glu Gln Leu Leu Val Thr Ile
    230                 235                 240

cag aaa aca ttt aat tat aat aag gca caa tca cat cag ctg ttt gca     1125
Gln Lys Thr Phe Asn Tyr Asn Lys Ala Gln Ser His Gln Leu Phe Ala
245                 250                 255                 260

att ata atg gag tgc atg aag aag aaa gaa ctc gtc act gtg ttc aga     1173
Ile Ile Met Glu Cys Met Lys Lys Lys Glu Leu Val Thr Val Phe Arg
                265                 270                 275

atg ggt tct gag ggc cag cag gac atc gag atg gca att tta act gcc     1221
Met Gly Ser Glu Gly Gln Gln Asp Ile Glu Met Ala Ile Leu Thr Ala
            280                 285                 290

ctg ctg aaa gga aca aac gta tct gct cca gat cag ctg agc ttg gca     1269
Leu Leu Lys Gly Thr Asn Val Ser Ala Pro Asp Gln Leu Ser Leu Ala
        295                 300                 305

ctg gct tgg aac cgc gtg gac ata gca cga agc cag atc ttt gtc ttt     1317
Leu Ala Trp Asn Arg Val Asp Ile Ala Arg Ser Gln Ile Phe Val Phe
    310                 315                 320

ggg ccc cac tgg acg ccc ctg gga agc ctg gca ccc ccg acg gac agc     1365
Gly Pro His Trp Thr Pro Leu Gly Ser Leu Ala Pro Pro Thr Asp Ser
325                 330                 335                 340

aaa gcc acg gag aag gag aag aag cca ccc atg gcc acc acc aag gga     1413
Lys Ala Thr Glu Lys Glu Lys Lys Pro Pro Met Ala Thr Thr Lys Gly
                345                 350                 355

gga aga gga aaa ggg aaa ggc aag aag aaa ggg aaa gtg aaa gag gaa     1461
Gly Arg Gly Lys Gly Lys Gly Lys Lys Lys Gly Lys Val Lys Glu Glu
            360                 365                 370

gtg gag gaa gaa act gac ccc cgg aag ata gag ctg ctg aac tgg gtg     1509
Val Glu Glu Glu Thr Asp Pro Arg Lys Ile Glu Leu Leu Asn Trp Val
        375                 380                 385

aat gct ttg gag caa gcg atg cta gat gct tta gtc tta gat cgt gtc     1557
Asn Ala Leu Glu Gln Ala Met Leu Asp Ala Leu Val Leu Asp Arg Val
    390                 395                 400

gac ttt gtg aag ctc ctg att gaa aac gga gtg aac atg caa cac ttt     1605
Asp Phe Val Lys Leu Leu Ile Glu Asn Gly Val Asn Met Gln His Phe
405                 410                 415                 420

ctg acc att ccg agg ctg gag gag ctt tat aac aca aga ctg ggt cca     1653
Leu Thr Ile Pro Arg Leu Glu Glu Leu Tyr Asn Thr Arg Leu Gly Pro
                425                 430                 435

cca aac aca ctt cat ctg ctg gtg agg gat gtg aaa aag agc aac ctt     1701
Pro Asn Thr Leu His Leu Leu Val Arg Asp Val Lys Lys Ser Asn Leu
            440                 445                 450

ccg cct gat tac cac atc agc ctc ata gac atc ggg ctc gtg ctg gag     1749
Pro Pro Asp Tyr His Ile Ser Leu Ile Asp Ile Gly Leu Val Leu Glu
        455                 460                 465
```

-continued

```
tac ctc atg gga gga gcc tac cgc tgc aac tac act cgg aaa aac ttt      1797
Tyr Leu Met Gly Gly Ala Tyr Arg Cys Asn Tyr Thr Arg Lys Asn Phe
    470                 475                 480

cgg acc ctt tac aac aac ttg ttt gga cca aag agg cct aaa gct ctt      1845
Arg Thr Leu Tyr Asn Asn Leu Phe Gly Pro Lys Arg Pro Lys Ala Leu
485                 490                 495                 500

aaa ctt ctg gga atg gaa gat gat gag cct cca gct aaa ggg aag aaa      1893
Lys Leu Leu Gly Met Glu Asp Asp Glu Pro Pro Ala Lys Gly Lys Lys
                505                 510                 515

aaa aaa aaa aag aaa aag gag gaa gag atc gac att gat gtg gac gac      1941
Lys Lys Lys Lys Lys Lys Glu Glu Glu Ile Asp Ile Asp Val Asp Asp
            520                 525                 530

cct gcc gtg agt cgg ttc cag tat ccc ttc cac gag ctg atg gtg tgg      1989
Pro Ala Val Ser Arg Phe Gln Tyr Pro Phe His Glu Leu Met Val Trp
        535                 540                 545

gca gtg ctg atg aaa cgc cag aaa atg gca gtg ttc ctc tgg cag cga      2037
Ala Val Leu Met Lys Arg Gln Lys Met Ala Val Phe Leu Trp Gln Arg
    550                 555                 560

ggg gaa gag agc atg gcc aag gcc ctg gtg gcc tgc aag ctc tac aag      2085
Gly Glu Glu Ser Met Ala Lys Ala Leu Val Ala Cys Lys Leu Tyr Lys
565                 570                 575                 580

gcc atg gcc cac gag tcc tcc gag agt gat ctg gtg gat gac atc tcc      2133
Ala Met Ala His Glu Ser Ser Glu Ser Asp Leu Val Asp Asp Ile Ser
                585                 590                 595

cag gac ttg gat aac aat tcc aaa gac ttc ggc cag ctt gct ttg gag      2181
Gln Asp Leu Asp Asn Asn Ser Lys Asp Phe Gly Gln Leu Ala Leu Glu
            600                 605                 610

tta tta gac cag tcc tat aag cat gac gag cag atc gct atg aaa ctc      2229
Leu Leu Asp Gln Ser Tyr Lys His Asp Glu Gln Ile Ala Met Lys Leu
        615                 620                 625

ctg acc tac gag ctg aaa aac tgg agc aac tcg acc tgc ctc aaa ctg      2277
Leu Thr Tyr Glu Leu Lys Asn Trp Ser Asn Ser Thr Cys Leu Lys Leu
    630                 635                 640

gcc gtg gca gcc aaa cac cgg gac ttc att gct cac acc tgc agc cag      2325
Ala Val Ala Ala Lys His Arg Asp Phe Ile Ala His Thr Cys Ser Gln
645                 650                 655                 660

atg ctg ctg acc gat atg tgg atg gga aga ctg cgg atg cgg aag aac      2373
Met Leu Leu Thr Asp Met Trp Met Gly Arg Leu Arg Met Arg Lys Asn
                665                 670                 675

ccc ggc ctg aag gtt atc atg ggg att ctt cta ccc ccc acc atc ttg      2421
Pro Gly Leu Lys Val Ile Met Gly Ile Leu Leu Pro Pro Thr Ile Leu
            680                 685                 690

ttt ttg gaa ttt cgc aca tat gat gat ttc tcg tat caa aca tcc aag      2469
Phe Leu Glu Phe Arg Thr Tyr Asp Asp Phe Ser Tyr Gln Thr Ser Lys
        695                 700                 705

gaa aac gag gat ggc aaa gaa aaa gaa gag gaa aat acg gat gca aat      2517
Glu Asn Glu Asp Gly Lys Glu Lys Glu Glu Glu Asn Thr Asp Ala Asn
    710                 715                 720

gca gat gct ggc tca aga aag ggg gat gag gag aac gag cat aaa aaa      2565
Ala Asp Ala Gly Ser Arg Lys Gly Asp Glu Glu Asn Glu His Lys Lys
725                 730                 735                 740

cag aga att atc ccc atc gga aca aaa atc tgt aaa ttc tat aac gcg      2613
Gln Arg Ile Ile Pro Ile Gly Thr Lys Ile Cys Lys Phe Tyr Asn Ala
                745                 750                 755

ccc att gtc aag ttc tgg ttt tac aca ata tca tac ttg ggc tac ctg      2661
Pro Ile Val Lys Phe Trp Phe Tyr Thr Ile Ser Tyr Leu Gly Tyr Leu
            760                 765                 770

ctg ctg ttt aac tac gtc atc ctg gtg cgg atg gat ggc tgg ccg tcc      2709
Leu Leu Phe Asn Tyr Val Ile Leu Val Arg Met Asp Gly Trp Pro Ser
```

-continued 775 780 785 ctc cag gag tgg atc gtc atc tcc tac atc gtg agc ctg gcg tta gag 2757
Leu Gln Glu Trp Ile Val Ile Ser Tyr Ile Val Ser Leu Ala Leu Glu
790 795 800 aag ata cga gag atc ctc atg tca gaa cca ggc aaa ctc agc cag aaa 2805
Lys Ile Arg Glu Ile Leu Met Ser Glu Pro Gly Lys Leu Ser Gln Lys
805 810 815 820 atc aaa gtt tgg ctt cag gag tac tgg aac atc aca gat ctc gtg gcc 2853
Ile Lys Val Trp Leu Gln Glu Tyr Trp Asn Ile Thr Asp Leu Val Ala
825 830 835 att tcc aca ttc atg att gga gca atg gcc acg aga tct gtg atg atg 2901
Ile Ser Thr Phe Met Ile Gly Ala Met Ala Thr Arg Ser Val Met Met
840 845 850 att gga aag atg atg atc gac atg ctg tac ttt gtg gtc atc atg ctg 2949
Ile Gly Lys Met Met Ile Asp Met Leu Tyr Phe Val Val Ile Met Leu
855 860 865 gtc gtg ctc atg agt ttc gga gta gcc cgt caa gcc att ctg cat cca 2997
Val Val Leu Met Ser Phe Gly Val Ala Arg Gln Ala Ile Leu His Pro
870 875 880 gag gag aag ccc tct tgg aaa ctg gcc cga aac atc ttc tac atg ccc 3045
Glu Glu Lys Pro Ser Trp Lys Leu Ala Arg Asn Ile Phe Tyr Met Pro
885 890 895 900 tac tgg atg atc tat gga gag gtg ttt gca gac cag ata gac ctc tac 3093
Tyr Trp Met Ile Tyr Gly Glu Val Phe Ala Asp Gln Ile Asp Leu Tyr
905 910 915 gcc atg gaa att aat cct cct tgt ggt gag aac cta tat gat gag gag 3141
Ala Met Glu Ile Asn Pro Pro Cys Gly Glu Asn Leu Tyr Asp Glu Glu
920 925 930 ggc aag cgg ctt cct ccc tgt atc ccc ggc gcc tgg ctc act cca gca 3189
Gly Lys Arg Leu Pro Pro Cys Ile Pro Gly Ala Trp Leu Thr Pro Ala
935 940 945 ctc atg gcg tgc tat cta ctg gtc gcc aac atc ctg ctg gtg aac ctg 3237
Leu Met Ala Cys Tyr Leu Leu Val Ala Asn Ile Leu Leu Val Asn Leu
950 955 960 ctg att gct gtg ttc aac aat acc ttc ttt gaa gta aaa tca ata tcc 3285
Leu Ile Ala Val Phe Asn Asn Thr Phe Phe Glu Val Lys Ser Ile Ser
965 970 975 980 aac cag gtg tgg aag ttc cag cga tat cag ctg att atg aca ttt cat 3333
Asn Gln Val Trp Lys Phe Gln Arg Tyr Gln Leu Ile Met Thr Phe His
985 990 995 gac agg cca gtc ctg ccc cca ccg atg atc att tta agc cac atc tac 3381
Asp Arg Pro Val Leu Pro Pro Pro Met Ile Ile Leu Ser His Ile Tyr
1000 1005 1010 atc atc att atg cgt ctc agc ggc cgc tgc agg aaa aag aga gaa ggg 3429
Ile Ile Ile Met Arg Leu Ser Gly Arg Cys Arg Lys Lys Arg Glu Gly
1015 1020 1025 gac caa gag gaa cgg gat cgt gga ttg aag ctc ttc ctt agc gac gag 3477
Asp Gln Glu Glu Arg Asp Arg Gly Leu Lys Leu Phe Leu Ser Asp Glu
1030 1035 1040 gag cta aag agg ctg cat gag ttc gag gag cag tgc gtg cag gag cac 3525
Glu Leu Lys Arg Leu His Glu Phe Glu Glu Gln Cys Val Gln Glu His
1045 1050 1055 1060 ttc cgg gag aag gag gat gag cag cag tcg tcc agc gac gag cgc atc 3573
Phe Arg Glu Lys Glu Asp Glu Gln Gln Ser Ser Ser Asp Glu Arg Ile
1065 1070 1075 cgg gtc act tct gaa aga gtt gaa aat atg tca atg agg ttg gaa gaa 3621
Arg Val Thr Ser Glu Arg Val Glu Asn Met Ser Met Arg Leu Glu Glu
1080 1085 1090 atc aat gaa aga gaa act ttt atg aaa act tcc ctg cag act gtt gac 3669

-continued

```
Ile Asn Glu Arg Glu Thr Phe Met Lys Thr Ser Leu Gln Thr Val Asp
       1095                1100                1105

ctt cga ctt gct cag cta gaa gaa tta tct aac aga atg gtg aat gct     3717
Leu Arg Leu Ala Gln Leu Glu Glu Leu Ser Asn Arg Met Val Asn Ala
   1110                1115                1120

ctt gaa aat ctt gcg gga atc gac agg tct gac ctg atc cag gca cgg     3765
Leu Glu Asn Leu Ala Gly Ile Asp Arg Ser Asp Leu Ile Gln Ala Arg
1125                1130                1135                1140

tcc cgg gct tct tct gaa tgt gag gca acg tat ctt ctc cgg caa agc     3813
Ser Arg Ala Ser Ser Glu Cys Glu Ala Thr Tyr Leu Leu Arg Gln Ser
               1145                1150                1155

agc atc aat agc gct gat ggc tac agc ttg tat cga tat cat ttt aac     3861
Ser Ile Asn Ser Ala Asp Gly Tyr Ser Leu Tyr Arg Tyr His Phe Asn
           1160                1165                1170

gga gaa gag tta tta ttt gag gat aca tct ctc tcc acg tca cca ggg     3909
Gly Glu Glu Leu Leu Phe Glu Asp Thr Ser Leu Ser Thr Ser Pro Gly
       1175                1180                1185

aca gga gtc agg aaa aaa acc tgt tcc ttc cgt ata aag gaa gag aag     3957
Thr Gly Val Arg Lys Lys Thr Cys Ser Phe Arg Ile Lys Glu Glu Lys
   1190                1195                1200

gac gtg aaa acg cac cta gtc cca gaa tgt cag aac agt ctt cac ctt     4005
Asp Val Lys Thr His Leu Val Pro Glu Cys Gln Asn Ser Leu His Leu
1205                1210                1215                1220

tca ctg ggc aca agc aca tca gca acc cca gat ggc agt cac ctt gca     4053
Ser Leu Gly Thr Ser Thr Ser Ala Thr Pro Asp Gly Ser His Leu Ala
               1225                1230                1235

gta gat gac tta aag aac gct gaa gag tca aaa tta ggt cca gat att     4101
Val Asp Asp Leu Lys Asn Ala Glu Glu Ser Lys Leu Gly Pro Asp Ile
           1240                1245                1250

ggg att tca aag gaa gat gat gaa aga cag aca gac tct aaa aaa gaa     4149
Gly Ile Ser Lys Glu Asp Asp Glu Arg Gln Thr Asp Ser Lys Lys Glu
       1255                1260                1265

gaa act att tcc cca agt tta aat aaa aca gat gtg ata cat gga cag     4197
Glu Thr Ile Ser Pro Ser Leu Asn Lys Thr Asp Val Ile His Gly Gln
   1270                1275                1280

gac aaa tca gat gtt caa aac act cag cta aca gtg gaa acg aca aat     4245
Asp Lys Ser Asp Val Gln Asn Thr Gln Leu Thr Val Glu Thr Thr Asn
1285                1290                1295                1300

ata gaa ggc act att tcc tat ccc ctg gaa gaa acc aaa att aca cgc     4293
Ile Glu Gly Thr Ile Ser Tyr Pro Leu Glu Glu Thr Lys Ile Thr Arg
               1305                1310                1315

tat ttc ccc gat gaa acg atc aat gct tgt aaa aca atg aag tcc aga     4341
Tyr Phe Pro Asp Glu Thr Ile Asn Ala Cys Lys Thr Met Lys Ser Arg
           1320                1325                1330

agc ttc gtc tat tcc cgg gga aga aag ctg gtc ggt ggg gtt aac cag     4389
Ser Phe Val Tyr Ser Arg Gly Arg Lys Leu Val Gly Gly Val Asn Gln
       1335                1340                1345

gat gta gag tac agt tca atc acg gac cag caa ttg acg acg gaa tgg     4437
Asp Val Glu Tyr Ser Ser Ile Thr Asp Gln Gln Leu Thr Thr Glu Trp
   1350                1355                1360

caa tgc caa gtt caa aag atc acg cgc tct cat agc aca gat att cct     4485
Gln Cys Gln Val Gln Lys Ile Thr Arg Ser His Ser Thr Asp Ile Pro
1365                1370                1375                1380

tac att gtg tcg gaa gct gca gtg caa gct gag caa aaa gag cag ttt     4533
Tyr Ile Val Ser Glu Ala Ala Val Gln Ala Glu Gln Lys Glu Gln Phe
               1385                1390                1395

gca gat atg caa gat gaa cac cat gtc gct gaa gca att cct cga atc     4581
Ala Asp Met Gln Asp Glu His His Val Ala Glu Ala Ile Pro Arg Ile
           1400                1405                1410
```

-continued

```
cct cgc ttg tcc cta acc att act gac aga aat ggg atg gaa aac tta     4629
Pro Arg Leu Ser Leu Thr Ile Thr Asp Arg Asn Gly Met Glu Asn Leu
       1415                1420                1425

ctg tct gtg aag cca gat caa act ttg gga ttc cca tct ctc agg tca     4677
Leu Ser Val Lys Pro Asp Gln Thr Leu Gly Phe Pro Ser Leu Arg Ser
   1430                1435                1440

aaa agt tta cat gga cat cct agg aat gtg aaa tcc att cag gga aag     4725
Lys Ser Leu His Gly His Pro Arg Asn Val Lys Ser Ile Gln Gly Lys
1445                1450                1455                1460

tta gac aga tct gga cat gcc agt agt gta agc agc tta gta att gtg     4773
Leu Asp Arg Ser Gly His Ala Ser Ser Val Ser Ser Leu Val Ile Val
               1465                1470                1475

tct gga atg aca gca gaa gaa aaa aag gtt aag aaa gag aaa gct tcc     4821
Ser Gly Met Thr Ala Glu Glu Lys Lys Val Lys Lys Glu Lys Ala Ser
           1480                1485                1490

aca gaa act gaa tgc tagtctgttt tgtttcttta attttttttt ttaacagtca     4876
Thr Glu Thr Glu Cys
       1495

gaaccactaa tgggtgtcat cttggccatc ctaaacatcc atccaatttc ctaaaaacat   4936

tttccctt                                                            4944


<210> SEQ ID NO 7
<211> LENGTH: 1497
<212> TYPE: PRT
<213> ORGANISM: Homo sapiens

<400> SEQUENCE: 7

Met Tyr Ile Arg Val Ser Tyr Asp Thr Lys Pro Asp Ser Leu Leu His
  1               5                  10                  15

Leu Met Val Lys Asp Trp Gln Leu Glu Leu Pro Lys Leu Leu Ile Ser
             20                  25                  30

Val His Gly Gly Leu Gln Asn Phe Glu Met Gln Pro Lys Leu Lys Gln
        35                  40                  45

Val Phe Gly Lys Gly Leu Ile Lys Ala Ala Met Thr Thr Gly Ala Trp
     50                  55                  60

Ile Phe Thr Gly Gly Val Ser Thr Gly Val Ile Ser His Val Gly Asp
 65                  70                  75                  80

Ala Leu Lys Asp His Ser Ser Lys Ser Arg Gly Arg Val Cys Ala Ile
                 85                  90                  95

Gly Ile Ala Pro Trp Gly Ile Val Glu Asn Lys Glu Asp Leu Val Gly
            100                 105                 110

Lys Asp Val Thr Arg Val Tyr Gln Thr Met Ser Asn Pro Leu Ser Lys
        115                 120                 125

Leu Ser Val Leu Asn Asn Ser His Thr His Phe Ile Leu Ala Asp Asn
    130                 135                 140

Gly Thr Leu Gly Lys Tyr Gly Ala Glu Val Lys Leu Arg Arg Leu Leu
145                 150                 155                 160

Glu Lys His Ile Ser Leu Gln Lys Ile Asn Thr Arg Leu Gly Gln Gly
                165                 170                 175

Val Pro Leu Val Gly Leu Val Val Glu Gly Gly Pro Asn Val Val Ser
            180                 185                 190

Ile Val Leu Glu Tyr Leu Gln Glu Glu Pro Pro Ile Pro Val Val Ile
        195                 200                 205

Cys Asp Gly Ser Gly Arg Ala Ser Asp Ile Leu Ser Phe Ala His Lys
    210                 215                 220

Tyr Cys Glu Glu Gly Gly Ile Ile Asn Glu Ser Leu Arg Glu Gln Leu
```

-continued

```
225                 230                 235                 240

Leu Val Thr Ile Gln Lys Thr Phe Asn Tyr Asn Lys Ala Gln Ser His
                245                 250                 255

Gln Leu Phe Ala Ile Ile Met Glu Cys Met Lys Lys Lys Glu Leu Val
            260                 265                 270

Thr Val Phe Arg Met Gly Ser Glu Gly Gln Gln Asp Ile Glu Met Ala
        275                 280                 285

Ile Leu Thr Ala Leu Leu Lys Gly Thr Asn Val Ser Ala Pro Asp Gln
    290                 295                 300

Leu Ser Leu Ala Leu Ala Trp Asn Arg Val Asp Ile Ala Arg Ser Gln
305                 310                 315                 320

Ile Phe Val Phe Gly Pro His Trp Thr Pro Leu Gly Ser Leu Ala Pro
                325                 330                 335

Pro Thr Asp Ser Lys Ala Thr Glu Lys Glu Lys Lys Pro Pro Met Ala
            340                 345                 350

Thr Thr Lys Gly Gly Arg Gly Lys Gly Lys Gly Lys Lys Lys Gly Lys
        355                 360                 365

Val Lys Glu Glu Val Glu Glu Glu Thr Asp Pro Arg Lys Ile Glu Leu
    370                 375                 380

Leu Asn Trp Val Asn Ala Leu Glu Gln Ala Met Leu Asp Ala Leu Val
385                 390                 395                 400

Leu Asp Arg Val Asp Phe Val Lys Leu Leu Ile Glu Asn Gly Val Asn
                405                 410                 415

Met Gln His Phe Leu Thr Ile Pro Arg Leu Glu Glu Leu Tyr Asn Thr
            420                 425                 430

Arg Leu Gly Pro Pro Asn Thr Leu His Leu Leu Val Arg Asp Val Lys
        435                 440                 445

Lys Ser Asn Leu Pro Pro Asp Tyr His Ile Ser Leu Ile Asp Ile Gly
    450                 455                 460

Leu Val Leu Glu Tyr Leu Met Gly Gly Ala Tyr Arg Cys Asn Tyr Thr
465                 470                 475                 480

Arg Lys Asn Phe Arg Thr Leu Tyr Asn Asn Leu Phe Gly Pro Lys Arg
                485                 490                 495

Pro Lys Ala Leu Lys Leu Leu Gly Met Glu Asp Asp Glu Pro Pro Ala
            500                 505                 510

Lys Gly Lys Lys Lys Lys Lys Lys Lys Lys Glu Glu Glu Ile Asp Ile
        515                 520                 525

Asp Val Asp Asp Pro Ala Val Ser Arg Phe Gln Tyr Pro Phe His Glu
    530                 535                 540

Leu Met Val Trp Ala Val Leu Met Lys Arg Gln Lys Met Ala Val Phe
545                 550                 555                 560

Leu Trp Gln Arg Gly Glu Glu Ser Met Ala Lys Ala Leu Val Ala Cys
                565                 570                 575

Lys Leu Tyr Lys Ala Met Ala His Glu Ser Ser Glu Ser Asp Leu Val
            580                 585                 590

Asp Asp Ile Ser Gln Asp Leu Asp Asn Asn Ser Lys Asp Phe Gly Gln
        595                 600                 605

Leu Ala Leu Glu Leu Leu Asp Gln Ser Tyr Lys His Asp Glu Gln Ile
    610                 615                 620

Ala Met Lys Leu Leu Thr Tyr Glu Leu Lys Asn Trp Ser Asn Ser Thr
625                 630                 635                 640

Cys Leu Lys Leu Ala Val Ala Ala Lys His Arg Asp Phe Ile Ala His
                645                 650                 655
```

-continued

```
Thr Cys Ser Gln Met Leu Leu Thr Asp Met Trp Met Gly Arg Leu Arg
            660                 665                 670

Met Arg Lys Asn Pro Gly Leu Lys Val Ile Met Gly Ile Leu Leu Pro
        675                 680                 685

Pro Thr Ile Leu Phe Leu Glu Phe Arg Thr Tyr Asp Asp Phe Ser Tyr
    690                 695                 700

Gln Thr Ser Lys Glu Asn Glu Asp Gly Lys Glu Lys Glu Glu Glu Asn
705                 710                 715                 720

Thr Asp Ala Asn Ala Asp Ala Gly Ser Arg Lys Gly Asp Glu Glu Asn
                725                 730                 735

Glu His Lys Lys Gln Arg Ile Ile Pro Ile Gly Thr Lys Ile Cys Lys
            740                 745                 750

Phe Tyr Asn Ala Pro Ile Val Lys Phe Trp Phe Tyr Thr Ile Ser Tyr
        755                 760                 765

Leu Gly Tyr Leu Leu Leu Phe Asn Tyr Val Ile Leu Val Arg Met Asp
    770                 775                 780

Gly Trp Pro Ser Leu Gln Glu Trp Ile Val Ile Ser Tyr Ile Val Ser
785                 790                 795                 800

Leu Ala Leu Glu Lys Ile Arg Glu Ile Leu Met Ser Glu Pro Gly Lys
                805                 810                 815

Leu Ser Gln Lys Ile Lys Val Trp Leu Gln Glu Tyr Trp Asn Ile Thr
            820                 825                 830

Asp Leu Val Ala Ile Ser Thr Phe Met Ile Gly Ala Met Ala Thr Arg
        835                 840                 845

Ser Val Met Met Ile Gly Lys Met Met Ile Asp Met Leu Tyr Phe Val
    850                 855                 860

Val Ile Met Leu Val Val Leu Met Ser Phe Gly Val Ala Arg Gln Ala
865                 870                 875                 880

Ile Leu His Pro Glu Glu Lys Pro Ser Trp Lys Leu Ala Arg Asn Ile
                885                 890                 895

Phe Tyr Met Pro Tyr Trp Met Ile Tyr Gly Glu Val Phe Ala Asp Gln
            900                 905                 910

Ile Asp Leu Tyr Ala Met Glu Ile Asn Pro Pro Cys Gly Glu Asn Leu
        915                 920                 925

Tyr Asp Glu Glu Gly Lys Arg Leu Pro Pro Cys Ile Pro Gly Ala Trp
    930                 935                 940

Leu Thr Pro Ala Leu Met Ala Cys Tyr Leu Leu Val Ala Asn Ile Leu
945                 950                 955                 960

Leu Val Asn Leu Leu Ile Ala Val Phe Asn Asn Thr Phe Phe Glu Val
                965                 970                 975

Lys Ser Ile Ser Asn Gln Val Trp Lys Phe Gln Arg Tyr Gln Leu Ile
            980                 985                 990

Met Thr Phe His Asp Arg Pro Val Leu Pro Pro Pro Met Ile Ile Leu
        995                1000                1005

Ser His Ile Tyr Ile Ile Ile Met Arg Leu Ser Gly Arg Cys Arg Lys
   1010                1015                1020

Lys Arg Glu Gly Asp Gln Glu Glu Arg Asp Arg Gly Leu Lys Leu Phe
1025                1030                1035                104

Leu Ser Asp Glu Glu Leu Lys Arg Leu His Glu Phe Glu Glu Gln Cys
               1045                1050                1055

Val Gln Glu His Phe Arg Glu Lys Glu Asp Glu Gln Gln Ser Ser Ser
           1060                1065                1070
```

-continued

```
Asp Glu Arg Ile Arg Val Thr Ser Glu Arg Val Glu Asn Met Ser Met
       1075                1080                1085

Arg Leu Glu Glu Ile Asn Glu Arg Glu Thr Phe Met Lys Thr Ser Leu
   1090                1095                1100

Gln Thr Val Asp Leu Arg Leu Ala Gln Leu Glu Glu Leu Ser Asn Arg
1105                1110                1115                112

Met Val Asn Ala Leu Glu Asn Leu Ala Gly Ile Asp Arg Ser Asp Leu
               1125                1130                1135

Ile Gln Ala Arg Ser Arg Ala Ser Ser Glu Cys Glu Ala Thr Tyr Leu
           1140                1145                1150

Leu Arg Gln Ser Ser Ile Asn Ser Ala Asp Gly Tyr Ser Leu Tyr Arg
       1155                1160                1165

Tyr His Phe Asn Gly Glu Glu Leu Leu Phe Glu Asp Thr Ser Leu Ser
   1170                1175                1180

Thr Ser Pro Gly Thr Gly Val Arg Lys Lys Thr Cys Ser Phe Arg Ile
1185                1190                1195                120

Lys Glu Glu Lys Asp Val Lys Thr His Leu Val Pro Glu Cys Gln Asn
               1205                1210                1215

Ser Leu His Leu Ser Leu Gly Thr Ser Thr Ser Ala Thr Pro Asp Gly
           1220                1225                1230

Ser His Leu Ala Val Asp Asp Leu Lys Asn Ala Glu Glu Ser Lys Leu
       1235                1240                1245

Gly Pro Asp Ile Gly Ile Ser Lys Glu Asp Asp Glu Arg Gln Thr Asp
   1250                1255                1260

Ser Lys Lys Glu Glu Thr Ile Ser Pro Ser Leu Asn Lys Thr Asp Val
1265                1270                1275                128

Ile His Gly Gln Asp Lys Ser Asp Val Gln Asn Thr Gln Leu Thr Val
               1285                1290                1295

Glu Thr Thr Asn Ile Glu Gly Thr Ile Ser Tyr Pro Leu Glu Glu Thr
           1300                1305                1310

Lys Ile Thr Arg Tyr Phe Pro Asp Glu Thr Ile Asn Ala Cys Lys Thr
       1315                1320                1325

Met Lys Ser Arg Ser Phe Val Tyr Ser Arg Gly Arg Lys Leu Val Gly
   1330                1335                1340

Gly Val Asn Gln Asp Val Glu Tyr Ser Ser Ile Thr Asp Gln Gln Leu
1345                1350                1355                136

Thr Thr Glu Trp Gln Cys Gln Val Gln Lys Ile Thr Arg Ser His Ser
               1365                1370                1375

Thr Asp Ile Pro Tyr Ile Val Ser Glu Ala Ala Val Gln Ala Glu Gln
           1380                1385                1390

Lys Glu Gln Phe Ala Asp Met Gln Asp Glu His His Val Ala Glu Ala
       1395                1400                1405

Ile Pro Arg Ile Pro Arg Leu Ser Leu Thr Ile Thr Asp Arg Asn Gly
   1410                1415                1420

Met Glu Asn Leu Leu Ser Val Lys Pro Asp Gln Thr Leu Gly Phe Pro
1425                1430                1435                144

Ser Leu Arg Ser Lys Ser Leu His Gly His Pro Arg Asn Val Lys Ser
               1445                1450                1455

Ile Gln Gly Lys Leu Asp Arg Ser Gly His Ala Ser Ser Val Ser Ser
           1460                1465                1470

Leu Val Ile Val Ser Gly Met Thr Ala Glu Glu Lys Lys Val Lys Lys
       1475                1480                1485

Glu Lys Ala Ser Thr Glu Thr Glu Cys
```

-continued

```
1490                1495

<210> SEQ ID NO 8
<211> LENGTH: 5055
<212> TYPE: DNA
<213> ORGANISM: Homo sapiens
<220> FEATURE:
<221> NAME/KEY: CDS
<222> LOCATION: (346)...(4944)

<400> SEQUENCE: 8

actcattata gggntcgagc ggccgcccgg gcaggtttga gctgtgccct ctccattcca      60

ctgctgtggc agggtcagaa atcttggata gagaaaacct tttgcaaacg ggaatgtatc     120

tttgtaattc ctagcacgaa agactctaac aggtgttgct gtggccagtt caccaaccag     180

catatccccc ctctgccaag tgcaacaccc agcaaaaatg aagaggaaag caaacaggtg     240

gagactcagc ctgagaaatg gtctgttgcc aagcacaccc agagctaccc aacagattcc     300

tatggagttc ttgaattcca gggtggcgga tattccaata aagcc atg tat atc cgt     357
                                                  Met Tyr Ile Arg
                                                    1

gta tcc tat gac acc aag cca gac tca ctg ctc cat ctc atg gtg aaa      405
Val Ser Tyr Asp Thr Lys Pro Asp Ser Leu Leu His Leu Met Val Lys
  5                  10                  15                  20

gat tgg cag ctg gaa ctc ccc aag ctc tta ata tct gtg cat gga ggc      453
Asp Trp Gln Leu Glu Leu Pro Lys Leu Leu Ile Ser Val His Gly Gly
                 25                  30                  35

ctc cag aac ttt gag atg cag ccc aag ctg aaa caa gtc ttt ggg aaa      501
Leu Gln Asn Phe Glu Met Gln Pro Lys Leu Lys Gln Val Phe Gly Lys
             40                  45                  50

ggc ctg atc aag gct gct atg acc acc ggg gcc tgg atc ttc acc ggg      549
Gly Leu Ile Lys Ala Ala Met Thr Thr Gly Ala Trp Ile Phe Thr Gly
         55                  60                  65

ggt gtc agc aca ggt gtt atc agc cac gta ggg gat gcc ttg aaa gac      597
Gly Val Ser Thr Gly Val Ile Ser His Val Gly Asp Ala Leu Lys Asp
     70                  75                  80

cac tcc tcc aag tcc aga ggc cgg gtt tgt gct ata gga att gct cca      645
His Ser Ser Lys Ser Arg Gly Arg Val Cys Ala Ile Gly Ile Ala Pro
 85                  90                  95                 100

tgg ggc atc gtg gag aat aag gaa gac ctg gtt gga aag gat gta aca      693
Trp Gly Ile Val Glu Asn Lys Glu Asp Leu Val Gly Lys Asp Val Thr
                105                 110                 115

aga gtg tac cag acc atg tcc aac cct cta agt aag ctc tct gtg ctc      741
Arg Val Tyr Gln Thr Met Ser Asn Pro Leu Ser Lys Leu Ser Val Leu
            120                 125                 130

aac aac tcc cac acc cac ttc atc ctg gct gac aat ggc acc ctg ggc      789
Asn Asn Ser His Thr His Phe Ile Leu Ala Asp Asn Gly Thr Leu Gly
        135                 140                 145

aag tat ggc gcc gag gtg aag ctg cga agg ctg ctg gaa aag cac atc      837
Lys Tyr Gly Ala Glu Val Lys Leu Arg Arg Leu Leu Glu Lys His Ile
    150                 155                 160

tcc ctc cag aag atc aac aca aga ctg ggg cag ggc gtg ccc ctc gtg      885
Ser Leu Gln Lys Ile Asn Thr Arg Leu Gly Gln Gly Val Pro Leu Val
165                 170                 175                 180

ggt ctc gtg gtg gag ggg ggc cct aac gtg gtg tcc atc gtc ttg gaa      933
Gly Leu Val Val Glu Gly Gly Pro Asn Val Val Ser Ile Val Leu Glu
                185                 190                 195

tac ctg caa gaa gag cct ccc atc cct gtg gtg att tgt gat ggc agc      981
Tyr Leu Gln Glu Glu Pro Pro Ile Pro Val Val Ile Cys Asp Gly Ser
            200                 205                 210
```

-continued

```
gga cgt gcc tcg gac atc ctg tcc ttt gcg cac aag tac tgt gaa gaa      1029
Gly Arg Ala Ser Asp Ile Leu Ser Phe Ala His Lys Tyr Cys Glu Glu
        215                 220                 225

ggc gga ata ata aat gag tcc ctc agg gag cag ctt cta gtt acc att      1077
Gly Gly Ile Ile Asn Glu Ser Leu Arg Glu Gln Leu Leu Val Thr Ile
    230                 235                 240

cag aaa aca ttt aat tat aat aag gca caa tca cat cag ctg ttt gca      1125
Gln Lys Thr Phe Asn Tyr Asn Lys Ala Gln Ser His Gln Leu Phe Ala
245                 250                 255                 260

att ata atg gag tgc atg aag aag aaa gaa ctc gtc act gtg ttc aga      1173
Ile Ile Met Glu Cys Met Lys Lys Lys Glu Leu Val Thr Val Phe Arg
                265                 270                 275

atg ggt tct gag ggc cag cag gac atc gag atg gca att tta act gcc      1221
Met Gly Ser Glu Gly Gln Gln Asp Ile Glu Met Ala Ile Leu Thr Ala
            280                 285                 290

ctg ctg aaa gga aca aac gta tct gct cca gat cag ctg agc ttg gca      1269
Leu Leu Lys Gly Thr Asn Val Ser Ala Pro Asp Gln Leu Ser Leu Ala
        295                 300                 305

ctg gct tgg aac cgc gtg gac ata gca cga agc cag atc ttt gtc ttt      1317
Leu Ala Trp Asn Arg Val Asp Ile Ala Arg Ser Gln Ile Phe Val Phe
    310                 315                 320

ggg ccc cac tgg acg ccc ctg gga agc ctg gca ccc ccg acg gac agc      1365
Gly Pro His Trp Thr Pro Leu Gly Ser Leu Ala Pro Pro Thr Asp Ser
325                 330                 335                 340

aaa gcc acg gag aag gag aag aag cca ccc atg gcc acc acc aag gga      1413
Lys Ala Thr Glu Lys Glu Lys Lys Pro Pro Met Ala Thr Thr Lys Gly
                345                 350                 355

gga aga gga aaa ggg aaa ggc aag aag aaa ggg aaa gtg aaa gag gaa      1461
Gly Arg Gly Lys Gly Lys Gly Lys Lys Lys Gly Lys Val Lys Glu Glu
            360                 365                 370

gtg gag gaa gaa act gac ccc cgg aag ata gag ctg ctg aac tgg gtg      1509
Val Glu Glu Glu Thr Asp Pro Arg Lys Ile Glu Leu Leu Asn Trp Val
        375                 380                 385

aat gct ttg gag caa gcg atg cta gat gct tta gtc tta gat cgt gtc      1557
Asn Ala Leu Glu Gln Ala Met Leu Asp Ala Leu Val Leu Asp Arg Val
    390                 395                 400

gac ttt gtg aag ctc ctg att gaa aac gga gtg aac atg caa cac ttt      1605
Asp Phe Val Lys Leu Leu Ile Glu Asn Gly Val Asn Met Gln His Phe
405                 410                 415                 420

ctg acc att ccg agg ctg gag gag ctt tat aac aca aga ctg ggt cca      1653
Leu Thr Ile Pro Arg Leu Glu Glu Leu Tyr Asn Thr Arg Leu Gly Pro
                425                 430                 435

cca aac aca ctt cat ctg ctg gtg agg gat gtg aaa aag agc aac ctt      1701
Pro Asn Thr Leu His Leu Leu Val Arg Asp Val Lys Lys Ser Asn Leu
            440                 445                 450

ccg cct gat tac cac atc agc ctc ata gac atc ggg ctc gtg ctg gag      1749
Pro Pro Asp Tyr His Ile Ser Leu Ile Asp Ile Gly Leu Val Leu Glu
        455                 460                 465

tac ctc atg gga gga gcc tac cgc tgc aac tac act cgg aaa aac ttt      1797
Tyr Leu Met Gly Gly Ala Tyr Arg Cys Asn Tyr Thr Arg Lys Asn Phe
    470                 475                 480

cgg acc ctt tac aac aac ttg ttt gga cca aag agg cct aaa gct ctt      1845
Arg Thr Leu Tyr Asn Asn Leu Phe Gly Pro Lys Arg Pro Lys Ala Leu
485                 490                 495                 500

aaa ctt ctg gga atg gaa gat gat gag cct cca gct aaa ggg aag aaa      1893
Lys Leu Leu Gly Met Glu Asp Asp Glu Pro Pro Ala Lys Gly Lys Lys
                505                 510                 515

aaa aaa aaa aag aaa aag gag gaa gag atc gac att gat gtg gac gac      1941
Lys Lys Lys Lys Lys Lys Glu Glu Glu Ile Asp Ile Asp Val Asp Asp
```

-continued

```
        520                 525                 530

cct gcc gtg agt cgg ttc cag tat ccc ttc cac gag ctg atg gtg tgg      1989
Pro Ala Val Ser Arg Phe Gln Tyr Pro Phe His Glu Leu Met Val Trp
    535                 540                 545

gca gtg ctg atg aaa cgc cag aaa atg gca gtg ttc ctc tgg cag cga      2037
Ala Val Leu Met Lys Arg Gln Lys Met Ala Val Phe Leu Trp Gln Arg
550                 555                 560

ggg gaa gag agc atg gcc aag gcc ctg gtg gcc tgc aag ctc tac aag      2085
Gly Glu Glu Ser Met Ala Lys Ala Leu Val Ala Cys Lys Leu Tyr Lys
565                 570                 575                 580

gcc atg gcc cac gag tcc tcc gag agt gat ctg gtg gat gac atc tcc      2133
Ala Met Ala His Glu Ser Ser Glu Ser Asp Leu Val Asp Asp Ile Ser
                585                 590                 595

cag gac ttg gat aac aat tcc aaa gac ttc ggc cag ctt gct ttg gag      2181
Gln Asp Leu Asp Asn Asn Ser Lys Asp Phe Gly Gln Leu Ala Leu Glu
            600                 605                 610

tta tta gac cag tcc tat aag cat gac gag cag atc gct atg aaa ctc      2229
Leu Leu Asp Gln Ser Tyr Lys His Asp Glu Gln Ile Ala Met Lys Leu
        615                 620                 625

ctg acc tac gag ctg aaa aac tgg agc aac tcg acc tgc ctc aaa ctg      2277
Leu Thr Tyr Glu Leu Lys Asn Trp Ser Asn Ser Thr Cys Leu Lys Leu
    630                 635                 640

gcc gtg gca gcc aaa cac cgg gac ttc att gct cac acc tgc agc cag      2325
Ala Val Ala Ala Lys His Arg Asp Phe Ile Ala His Thr Cys Ser Gln
645                 650                 655                 660

atg ctg ctg acc gat atg tgg atg gga aga ctg cgg atg cgg aag aac      2373
Met Leu Leu Thr Asp Met Trp Met Gly Arg Leu Arg Met Arg Lys Asn
                665                 670                 675

ccc ggc ctg aag gtt atc atg ggg att ctt cta ccc ccc acc atc ttg      2421
Pro Gly Leu Lys Val Ile Met Gly Ile Leu Leu Pro Pro Thr Ile Leu
            680                 685                 690

ttt ttg gaa ttt cgc aca tat gat gat ttc tcg tat caa aca tcc aag      2469
Phe Leu Glu Phe Arg Thr Tyr Asp Asp Phe Ser Tyr Gln Thr Ser Lys
        695                 700                 705

gaa aac gag gat ggc aaa gaa aaa gaa gag gaa aat acg gat gca aat      2517
Glu Asn Glu Asp Gly Lys Glu Lys Glu Glu Glu Asn Thr Asp Ala Asn
    710                 715                 720

gca gat gct ggc tca aga aag ggg gat gag gag aac gag cat aaa aaa      2565
Ala Asp Ala Gly Ser Arg Lys Gly Asp Glu Glu Asn Glu His Lys Lys
725                 730                 735                 740

cag aga agt att ccc atc gga aca aag atc tgt gaa ttc tat aac gcg      2613
Gln Arg Ser Ile Pro Ile Gly Thr Lys Ile Cys Glu Phe Tyr Asn Ala
                745                 750                 755

ccc att gtc aag ttc tgg ttt tac aca ata tca tac ttg ggc tac ctg      2661
Pro Ile Val Lys Phe Trp Phe Tyr Thr Ile Ser Tyr Leu Gly Tyr Leu
            760                 765                 770

ctg ctg ttt aac tac gtc atc ctg gtg cgg atg gat ggc tgg ccg tcc      2709
Leu Leu Phe Asn Tyr Val Ile Leu Val Arg Met Asp Gly Trp Pro Ser
        775                 780                 785

ctc cag gag tgg atc gtc atc tcc tac atc gtg agc ctg gcg tta gag      2757
Leu Gln Glu Trp Ile Val Ile Ser Tyr Ile Val Ser Leu Ala Leu Glu
    790                 795                 800

aag ata cga gag atc ctc atg tca gaa cca ggc aaa ctc agc cag aaa      2805
Lys Ile Arg Glu Ile Leu Met Ser Glu Pro Gly Lys Leu Ser Gln Lys
805                 810                 815                 820

atc aaa gtt tgg ctt cag gag tac tgg aac atc aca gat ctc gtg gcc      2853
Ile Lys Val Trp Leu Gln Glu Tyr Trp Asn Ile Thr Asp Leu Val Ala
                825                 830                 835

att tcc aca ttc atg att gga gca att ctt cgc cta cag aac cag ccc      2901
```

-continued

```
Ile Ser Thr Phe Met Ile Gly Ala Ile Leu Arg Leu Gln Asn Gln Pro
            840                 845                 850

tac atg ggc tat ggc cgg gtg atc tac tgt gtg gat atc atc ttc tgg     2949
Tyr Met Gly Tyr Gly Arg Val Ile Tyr Cys Val Asp Ile Ile Phe Trp
        855                 860                 865

tac atc cgt gtc ctg gac atc ttt ggt gtc aac aag tat ctg ggg cca     2997
Tyr Ile Arg Val Leu Asp Ile Phe Gly Val Asn Lys Tyr Leu Gly Pro
    870                 875                 880

tac gtg atg atg att gga aag atg atg atc gac atg ctg tac ttt gtg     3045
Tyr Val Met Met Ile Gly Lys Met Met Ile Asp Met Leu Tyr Phe Val
885                 890                 895                 900

gtc atc atg ctg gtc gtg ctc atg agt ttc gga gta gcc cgt caa gcc     3093
Val Ile Met Leu Val Val Leu Met Ser Phe Gly Val Ala Arg Gln Ala
                905                 910                 915

att ctg cat cca gag gag aag ccc tct tgg aaa ctg gcc cga aac atc     3141
Ile Leu His Pro Glu Glu Lys Pro Ser Trp Lys Leu Ala Arg Asn Ile
            920                 925                 930

ttc tac atg ccc tac tgg atg atc tat gga gag gtg ttt gca gac cag     3189
Phe Tyr Met Pro Tyr Trp Met Ile Tyr Gly Glu Val Phe Ala Asp Gln
        935                 940                 945

ata gac ctc tac gcc atg gaa att aat cct cct tgt ggt gag aac cta     3237
Ile Asp Leu Tyr Ala Met Glu Ile Asn Pro Pro Cys Gly Glu Asn Leu
    950                 955                 960

tat gat gag gag ggc aag cgg ctt cct ccc tgt atc ccc ggc gcc tgg     3285
Tyr Asp Glu Glu Gly Lys Arg Leu Pro Pro Cys Ile Pro Gly Ala Trp
965                 970                 975                 980

ctc act cca gca ctc atg gcg tgc tat cta ctg gtc gcc aac atc ctg     3333
Leu Thr Pro Ala Leu Met Ala Cys Tyr Leu Leu Val Ala Asn Ile Leu
                985                 990                 995

ctg gtg aac ctg ctg att gct gtg ttc aac aat act ttc ttt gaa gta     3381
Leu Val Asn Leu Leu Ile Ala Val Phe Asn Asn Thr Phe Phe Glu Val
           1000                1005                1010

aaa tca ata tcc aac cag gtg tgg aag ttc cag cga tat cag ctg att     3429
Lys Ser Ile Ser Asn Gln Val Trp Lys Phe Gln Arg Tyr Gln Leu Ile
       1015                1020                1025

atg aca ttt cat gac agg cca gtc ctg ccc cca ccg atg atc att tta     3477
Met Thr Phe His Asp Arg Pro Val Leu Pro Pro Pro Met Ile Ile Leu
   1030                1035                1040

agc cac atc tac atc atc att atg cgt ctc agc ggc cgc tgc agg aaa     3525
Ser His Ile Tyr Ile Ile Ile Met Arg Leu Ser Gly Arg Cys Arg Lys
1045                1050                1055                1060

aag aga gaa ggg gac caa gag gaa cgg gat cgt gga ttg aag ctc ttc     3573
Lys Arg Glu Gly Asp Gln Glu Glu Arg Asp Arg Gly Leu Lys Leu Phe
               1065                1070                1075

ctt agc gac gag gag cta aag agg ctg cat gag ttc gag gag cag tgc     3621
Leu Ser Asp Glu Glu Leu Lys Arg Leu His Glu Phe Glu Glu Gln Cys
           1080                1085                1090

gtg cag gag cac ttc cgg gag aag gag gat gag cag cag tcg tcc agc     3669
Val Gln Glu His Phe Arg Glu Lys Glu Asp Glu Gln Gln Ser Ser Ser
       1095                1100                1105

gac gag cgc atc cgg gtc act tct gaa aga gtt gaa aat atg tca atg     3717
Asp Glu Arg Ile Arg Val Thr Ser Glu Arg Val Glu Asn Met Ser Met
   1110                1115                1120

agg ttg gaa gaa atc aat gaa aga gaa act ttt atg aaa act tcc ctg     3765
Arg Leu Glu Glu Ile Asn Glu Arg Glu Thr Phe Met Lys Thr Ser Leu
1125                1130                1135                1140

cag act gtt gac ctt cga ctt gct cag cta gaa gaa tta tct aac aga     3813
Gln Thr Val Asp Leu Arg Leu Ala Gln Leu Glu Glu Leu Ser Asn Arg
               1145                1150                1155
```

-continued

```
atg gtg aat gct ctt gaa aat ctt gcg gga atc gac agg tct gac ctg      3861
Met Val Asn Ala Leu Glu Asn Leu Ala Gly Ile Asp Arg Ser Asp Leu
            1160                1165                1170

atc cag gca cgg tcc cgg gct tct tct gaa tgt gag gca acg tat ctt      3909
Ile Gln Ala Arg Ser Arg Ala Ser Ser Glu Cys Glu Ala Thr Tyr Leu
        1175                1180                1185

ctc cgg caa agc agc atc aat agc gct gat ggc tac agc ttg tat cga      3957
Leu Arg Gln Ser Ser Ile Asn Ser Ala Asp Gly Tyr Ser Leu Tyr Arg
    1190                1195                1200

tat cat ttt aac gga gaa gag tta tta ttt gag gat aca tct ctc tcc      4005
Tyr His Phe Asn Gly Glu Glu Leu Leu Phe Glu Asp Thr Ser Leu Ser
1205                1210                1215                1220

acg tca cca ggg aca gga gtc agg aaa aaa acc tgt tcc ttc cgt ata      4053
Thr Ser Pro Gly Thr Gly Val Arg Lys Lys Thr Cys Ser Phe Arg Ile
                1225                1230                1235

aag gaa gag aag gac gtg aaa acg cac cta gtc cca gaa tgt cag aac      4101
Lys Glu Glu Lys Asp Val Lys Thr His Leu Val Pro Glu Cys Gln Asn
            1240                1245                1250

agt ctt cac ctt tca ctg ggc aca agc aca tca gca acc cca gat ggc      4149
Ser Leu His Leu Ser Leu Gly Thr Ser Thr Ser Ala Thr Pro Asp Gly
        1255                1260                1265

agt cac ctt gca gta gat gac tta aag aac gct gaa gag tca aaa tta      4197
Ser His Leu Ala Val Asp Asp Leu Lys Asn Ala Glu Glu Ser Lys Leu
    1270                1275                1280

ggt cca gat att ggg att tca aag gaa gat gat gaa aga cag aca gac      4245
Gly Pro Asp Ile Gly Ile Ser Lys Glu Asp Asp Glu Arg Gln Thr Asp
1285                1290                1295                1300

tct aaa aaa gaa gaa act att tcc cca agt tta aat aaa aca gat gtg      4293
Ser Lys Lys Glu Glu Thr Ile Ser Pro Ser Leu Asn Lys Thr Asp Val
                1305                1310                1315

ata cat gga cag gac aaa tca gat gtt caa aac act cag cta aca gtg      4341
Ile His Gly Gln Asp Lys Ser Asp Val Gln Asn Thr Gln Leu Thr Val
            1320                1325                1330

gaa acg aca aat ata gaa ggc act att tcc tat ccc ctg gaa gaa acc      4389
Glu Thr Thr Asn Ile Glu Gly Thr Ile Ser Tyr Pro Leu Glu Glu Thr
        1335                1340                1345

aaa att aca cgc tat ttc ccc gat gaa acg atc aat gct tgt aaa aca      4437
Lys Ile Thr Arg Tyr Phe Pro Asp Glu Thr Ile Asn Ala Cys Lys Thr
    1350                1355                1360

atg aag tcc aga agc ttc gtc tat tcc cgg gga aga aag ctg gtc ggt      4485
Met Lys Ser Arg Ser Phe Val Tyr Ser Arg Gly Arg Lys Leu Val Gly
1365                1370                1375                1380

ggg gtt aac cag gat gta gag tac agt tca atc acg gac cag caa ttg      4533
Gly Val Asn Gln Asp Val Glu Tyr Ser Ser Ile Thr Asp Gln Gln Leu
                1385                1390                1395

acg acg gaa tgg caa tgc caa gtt caa aag atc acg cgc tct cat agc      4581
Thr Thr Glu Trp Gln Cys Gln Val Gln Lys Ile Thr Arg Ser His Ser
            1400                1405                1410

aca gat att cct tac att gtg tcg gaa gct gca gtg caa gct gag caa      4629
Thr Asp Ile Pro Tyr Ile Val Ser Glu Ala Ala Val Gln Ala Glu Gln
        1415                1420                1425

aaa gag cag ttt gca gat atg caa gat gaa cac cat gtc gct gaa gca      4677
Lys Glu Gln Phe Ala Asp Met Gln Asp Glu His His Val Ala Glu Ala
    1430                1435                1440

att cct cga atc cct cgc ttg tcc cta acc att act gac aga aat ggg      4725
Ile Pro Arg Ile Pro Arg Leu Ser Leu Thr Ile Thr Asp Arg Asn Gly
1445                1450                1455                1460

atg gaa aac tta ctg tct gtg aag cca gat caa act ttg gga ttc cca      4773
Met Glu Asn Leu Leu Ser Val Lys Pro Asp Gln Thr Leu Gly Phe Pro
                1465                1470                1475
```

-continued

```
tct ctc agg tca aaa agt tta cat gga cat cct agg aat gtg aaa tcc     4821
Ser Leu Arg Ser Lys Ser Leu His Gly His Pro Arg Asn Val Lys Ser
           1480                1485                1490

att cag gga aag tta gac aga tct gga cat gcc agt agt gta agc agc     4869
Ile Gln Gly Lys Leu Asp Arg Ser Gly His Ala Ser Ser Val Ser Ser
       1495                1500                1505

tta gta att gtg tct gga atg aca gca gaa gaa aaa aag gtt aag aaa     4917
Leu Val Ile Val Ser Gly Met Thr Ala Glu Glu Lys Lys Val Lys Lys
   1510                1515                1520

gag aaa gct tcc aca gaa act gaa tgc tagtctgttt tgtttcttta           4964
Glu Lys Ala Ser Thr Glu Thr Glu Cys
1525                1530

attttttttt ttaacagtca gaaacccact aatgggtgtc atcttggccc atcctaaaca   5024

catmtccaat ttcctaaaaa cattttccct t                                  5055


<210> SEQ ID NO 9
<211> LENGTH: 1533
<212> TYPE: PRT
<213> ORGANISM: Homo sapiens

<400> SEQUENCE: 9

Met Tyr Ile Arg Val Ser Tyr Asp Thr Lys Pro Asp Ser Leu Leu His
  1               5                  10                  15

Leu Met Val Lys Asp Trp Gln Leu Glu Leu Pro Lys Leu Leu Ile Ser
             20                  25                  30

Val His Gly Gly Leu Gln Asn Phe Glu Met Gln Pro Lys Leu Lys Gln
         35                  40                  45

Val Phe Gly Lys Gly Leu Ile Lys Ala Ala Met Thr Thr Gly Ala Trp
     50                  55                  60

Ile Phe Thr Gly Gly Val Ser Thr Gly Val Ile Ser His Val Gly Asp
 65                  70                  75                  80

Ala Leu Lys Asp His Ser Ser Lys Ser Arg Gly Arg Val Cys Ala Ile
                 85                  90                  95

Gly Ile Ala Pro Trp Gly Ile Val Glu Asn Lys Glu Asp Leu Val Gly
            100                 105                 110

Lys Asp Val Thr Arg Val Tyr Gln Thr Met Ser Asn Pro Leu Ser Lys
        115                 120                 125

Leu Ser Val Leu Asn Asn Ser His Thr His Phe Ile Leu Ala Asp Asn
    130                 135                 140

Gly Thr Leu Gly Lys Tyr Gly Ala Glu Val Lys Leu Arg Arg Leu Leu
145                 150                 155                 160

Glu Lys His Ile Ser Leu Gln Lys Ile Asn Thr Arg Leu Gly Gln Gly
                165                 170                 175

Val Pro Leu Val Gly Leu Val Val Glu Gly Gly Pro Asn Val Val Ser
            180                 185                 190

Ile Val Leu Glu Tyr Leu Gln Glu Glu Pro Pro Ile Pro Val Val Ile
        195                 200                 205

Cys Asp Gly Ser Gly Arg Ala Ser Asp Ile Leu Ser Phe Ala His Lys
    210                 215                 220

Tyr Cys Glu Glu Gly Gly Ile Ile Asn Glu Ser Leu Arg Glu Gln Leu
225                 230                 235                 240

Leu Val Thr Ile Gln Lys Thr Phe Asn Tyr Asn Lys Ala Gln Ser His
                245                 250                 255

Gln Leu Phe Ala Ile Ile Met Glu Cys Met Lys Lys Lys Glu Leu Val
            260                 265                 270
```

-continued

```
Thr Val Phe Arg Met Gly Ser Glu Gly Gln Gln Asp Ile Glu Met Ala
        275                 280                 285

Ile Leu Thr Ala Leu Leu Lys Gly Thr Asn Val Ser Ala Pro Asp Gln
    290                 295                 300

Leu Ser Leu Ala Leu Ala Trp Asn Arg Val Asp Ile Ala Arg Ser Gln
305                 310                 315                 320

Ile Phe Val Phe Gly Pro His Trp Thr Pro Leu Gly Ser Leu Ala Pro
                325                 330                 335

Pro Thr Asp Ser Lys Ala Thr Glu Lys Glu Lys Lys Pro Pro Met Ala
            340                 345                 350

Thr Thr Lys Gly Gly Arg Gly Lys Gly Lys Gly Lys Lys Lys Gly Lys
        355                 360                 365

Val Lys Glu Glu Val Glu Glu Glu Thr Asp Pro Arg Lys Ile Glu Leu
    370                 375                 380

Leu Asn Trp Val Asn Ala Leu Glu Gln Ala Met Leu Asp Ala Leu Val
385                 390                 395                 400

Leu Asp Arg Val Asp Phe Val Lys Leu Leu Ile Glu Asn Gly Val Asn
                405                 410                 415

Met Gln His Phe Leu Thr Ile Pro Arg Leu Glu Glu Leu Tyr Asn Thr
            420                 425                 430

Arg Leu Gly Pro Pro Asn Thr Leu His Leu Leu Val Arg Asp Val Lys
        435                 440                 445

Lys Ser Asn Leu Pro Pro Asp Tyr His Ile Ser Leu Ile Asp Ile Gly
    450                 455                 460

Leu Val Leu Glu Tyr Leu Met Gly Gly Ala Tyr Arg Cys Asn Tyr Thr
465                 470                 475                 480

Arg Lys Asn Phe Arg Thr Leu Tyr Asn Asn Leu Phe Gly Pro Lys Arg
                485                 490                 495

Pro Lys Ala Leu Lys Leu Leu Gly Met Glu Asp Asp Glu Pro Pro Ala
            500                 505                 510

Lys Gly Lys Lys Lys Lys Lys Lys Lys Lys Glu Glu Glu Ile Asp Ile
        515                 520                 525

Asp Val Asp Asp Pro Ala Val Ser Arg Phe Gln Tyr Pro Phe His Glu
    530                 535                 540

Leu Met Val Trp Ala Val Leu Met Lys Arg Gln Lys Met Ala Val Phe
545                 550                 555                 560

Leu Trp Gln Arg Gly Glu Glu Ser Met Ala Lys Ala Leu Val Ala Cys
                565                 570                 575

Lys Leu Tyr Lys Ala Met Ala His Glu Ser Ser Glu Ser Asp Leu Val
            580                 585                 590

Asp Asp Ile Ser Gln Asp Leu Asp Asn Asn Ser Lys Asp Phe Gly Gln
        595                 600                 605

Leu Ala Leu Glu Leu Leu Asp Gln Ser Tyr Lys His Asp Glu Gln Ile
    610                 615                 620

Ala Met Lys Leu Leu Thr Tyr Glu Leu Lys Asn Trp Ser Asn Ser Thr
625                 630                 635                 640

Cys Leu Lys Leu Ala Val Ala Ala Lys His Arg Asp Phe Ile Ala His
                645                 650                 655

Thr Cys Ser Gln Met Leu Leu Thr Asp Met Trp Met Gly Arg Leu Arg
            660                 665                 670

Met Arg Lys Asn Pro Gly Leu Lys Val Ile Met Gly Ile Leu Leu Pro
        675                 680                 685
```

-continued

```
Pro Thr Ile Leu Phe Leu Glu Phe Arg Thr Tyr Asp Asp Phe Ser Tyr
    690                 695                 700

Gln Thr Ser Lys Glu Asn Glu Asp Gly Lys Glu Lys Glu Glu Glu Asn
705                 710                 715                 720

Thr Asp Ala Asn Ala Asp Ala Gly Ser Arg Lys Gly Asp Glu Glu Asn
                725                 730                 735

Glu His Lys Lys Gln Arg Ser Ile Pro Ile Gly Thr Lys Ile Cys Glu
            740                 745                 750

Phe Tyr Asn Ala Pro Ile Val Lys Phe Trp Phe Tyr Thr Ile Ser Tyr
        755                 760                 765

Leu Gly Tyr Leu Leu Leu Phe Asn Tyr Val Ile Leu Val Arg Met Asp
    770                 775                 780

Gly Trp Pro Ser Leu Gln Glu Trp Ile Val Ile Ser Tyr Ile Val Ser
785                 790                 795                 800

Leu Ala Leu Glu Lys Ile Arg Glu Ile Leu Met Ser Glu Pro Gly Lys
                805                 810                 815

Leu Ser Gln Lys Ile Lys Val Trp Leu Gln Glu Tyr Trp Asn Ile Thr
            820                 825                 830

Asp Leu Val Ala Ile Ser Thr Phe Met Ile Gly Ala Ile Leu Arg Leu
        835                 840                 845

Gln Asn Gln Pro Tyr Met Gly Tyr Gly Arg Val Ile Tyr Cys Val Asp
    850                 855                 860

Ile Ile Phe Trp Tyr Ile Arg Val Leu Asp Ile Phe Gly Val Asn Lys
865                 870                 875                 880

Tyr Leu Gly Pro Tyr Val Met Met Ile Gly Lys Met Met Ile Asp Met
                885                 890                 895

Leu Tyr Phe Val Val Ile Met Leu Val Val Leu Met Ser Phe Gly Val
            900                 905                 910

Ala Arg Gln Ala Ile Leu His Pro Glu Glu Lys Pro Ser Trp Lys Leu
        915                 920                 925

Ala Arg Asn Ile Phe Tyr Met Pro Tyr Trp Met Ile Tyr Gly Glu Val
    930                 935                 940

Phe Ala Asp Gln Ile Asp Leu Tyr Ala Met Glu Ile Asn Pro Pro Cys
945                 950                 955                 960

Gly Glu Asn Leu Tyr Asp Glu Glu Gly Lys Arg Leu Pro Pro Cys Ile
                965                 970                 975

Pro Gly Ala Trp Leu Thr Pro Ala Leu Met Ala Cys Tyr Leu Leu Val
            980                 985                 990

Ala Asn Ile Leu Leu Val Asn Leu Leu Ile Ala Val Phe Asn Asn Thr
        995                 1000                1005

Phe Phe Glu Val Lys Ser Ile Ser Asn Gln Val Trp Lys Phe Gln Arg
    1010                1015                1020

Tyr Gln Leu Ile Met Thr Phe His Asp Arg Pro Val Leu Pro Pro Pro
1025                1030                1035                104

Met Ile Ile Leu Ser His Ile Tyr Ile Ile Ile Met Arg Leu Ser Gly
                1045                1050                1055

Arg Cys Arg Lys Lys Arg Glu Gly Asp Gln Glu Glu Arg Asp Arg Gly
            1060                1065                1070

Leu Lys Leu Phe Leu Ser Asp Glu Glu Leu Lys Arg Leu His Glu Phe
        1075                1080                1085

Glu Glu Gln Cys Val Gln Glu His Phe Arg Glu Lys Glu Asp Glu Gln
    1090                1095                1100

Gln Ser Ser Ser Asp Glu Arg Ile Arg Val Thr Ser Glu Arg Val Glu
```

-continued

```
1105                1110                1115                112

Asn Met Ser Met Arg Leu Glu Glu Ile Asn Glu Arg Glu Thr Phe Met
                1125                1130                1135

Lys Thr Ser Leu Gln Thr Val Asp Leu Arg Leu Ala Gln Leu Glu Glu
            1140                1145                1150

Leu Ser Asn Arg Met Val Asn Ala Leu Glu Asn Leu Ala Gly Ile Asp
        1155                1160                1165

Arg Ser Asp Leu Ile Gln Ala Arg Ser Arg Ala Ser Ser Glu Cys Glu
    1170                1175                1180

Ala Thr Tyr Leu Leu Arg Gln Ser Ser Ile Asn Ser Ala Asp Gly Tyr
1185                1190                1195                120

Ser Leu Tyr Arg Tyr His Phe Asn Gly Glu Glu Leu Leu Phe Glu Asp
                1205                1210                1215

Thr Ser Leu Ser Thr Ser Pro Gly Thr Gly Val Arg Lys Lys Thr Cys
            1220                1225                1230

Ser Phe Arg Ile Lys Glu Glu Lys Asp Val Lys Thr His Leu Val Pro
        1235                1240                1245

Glu Cys Gln Asn Ser Leu His Leu Ser Leu Gly Thr Ser Thr Ser Ala
    1250                1255                1260

Thr Pro Asp Gly Ser His Leu Ala Val Asp Asp Leu Lys Asn Ala Glu
1265                1270                1275                128

Glu Ser Lys Leu Gly Pro Asp Ile Gly Ile Ser Lys Glu Asp Asp Glu
                1285                1290                1295

Arg Gln Thr Asp Ser Lys Lys Glu Glu Thr Ile Ser Pro Ser Leu Asn
            1300                1305                1310

Lys Thr Asp Val Ile His Gly Gln Asp Lys Ser Asp Val Gln Asn Thr
        1315                1320                1325

Gln Leu Thr Val Glu Thr Thr Asn Ile Glu Gly Thr Ile Ser Tyr Pro
    1330                1335                1340

Leu Glu Glu Thr Lys Ile Thr Arg Tyr Phe Pro Asp Glu Thr Ile Asn
1345                1350                1355                136

Ala Cys Lys Thr Met Lys Ser Arg Ser Phe Val Tyr Ser Arg Gly Arg
                1365                1370                1375

Lys Leu Val Gly Gly Val Asn Gln Asp Val Glu Tyr Ser Ser Ile Thr
            1380                1385                1390

Asp Gln Gln Leu Thr Thr Glu Trp Gln Cys Gln Val Gln Lys Ile Thr
        1395                1400                1405

Arg Ser His Ser Thr Asp Ile Pro Tyr Ile Val Ser Glu Ala Ala Val
    1410                1415                1420

Gln Ala Glu Gln Lys Glu Gln Phe Ala Asp Met Gln Asp Glu His His
1425                1430                1435                144

Val Ala Glu Ala Ile Pro Arg Ile Pro Arg Leu Ser Leu Thr Ile Thr
                1445                1450                1455

Asp Arg Asn Gly Met Glu Asn Leu Leu Ser Val Lys Pro Asp Gln Thr
            1460                1465                1470

Leu Gly Phe Pro Ser Leu Arg Ser Lys Ser Leu His Gly His Pro Arg
        1475                1480                1485

Asn Val Lys Ser Ile Gln Gly Lys Leu Asp Arg Ser Gly His Ala Ser
    1490                1495                1500
```

-continued

```
Ser Val Ser Ser Leu Val Ile Val Ser Gly Met Thr Ala Glu Glu Lys
1505                1510                1515                152

Lys Val Lys Lys Glu Lys Ala Ser Thr Glu Thr Glu Cys
                1525                1530
```